(12) United States Patent
Sabry et al.

(10) Patent No.: US 12,385,892 B2
(45) Date of Patent: Aug. 12, 2025

(54) SELF-CALIBRATED SPECTROSCOPIC AND AI-BASED GAS ANALYZER

(71) Applicant: Si-Ware Systems, Cairo (EG)

(72) Inventors: Yasser M. Sabry, Cairo (EG); Bassem Mortada, Cairo (EG); Mohamed H. Al Haron, Cairo (EG); Momen Anwar, Cairo (EG); Mohamed Metwally Youssef, Cairo (EG); Mazen Erfan, Cairo (EG); Erik R. Deutsch, Brookline, MA (US)

(73) Assignee: SI-WARE SYSTEMS, Cairo (EG)

( * ) Notice: Subject to any disclaimer, the term of this patent is extended or adjusted under 35 U.S.C. 154(b) by 359 days.

(21) Appl. No.: 17/857,964

(22) Filed: Jul. 5, 2022

(65) Prior Publication Data

US 2023/0014558 A1 Jan. 19, 2023

Related U.S. Application Data

(60) Provisional application No. 63/218,885, filed on Jul. 6, 2021.

(51) Int. Cl.
| | |
|---|---|
| *G01N 33/00* | (2006.01) |
| *B81B 7/02* | (2006.01) |
| *G01J 3/10* | (2006.01) |
| *G01N 21/3504* | (2014.01) |
| *G06N 3/02* | (2006.01) |

(52) U.S. Cl.
CPC ........... *G01N 33/0062* (2013.01); *B81B 7/02* (2013.01); *G01J 3/108* (2013.01);
(Continued)

(58) Field of Classification Search
CPC ........... G01N 33/0062; G01N 33/0068; G01N 21/3504
(Continued)

(56) References Cited

U.S. PATENT DOCUMENTS 9,651,488 B2 * 5/2017 Scherer ................. G01N 21/61
9,658,053 B2 5/2017 Medhat et al.
(Continued)

FOREIGN PATENT DOCUMENTS

| CN | 104614337 A | 5/2015 |
|---|---|---|
| WO | 2020009150 A1 | 8/2021 |

OTHER PUBLICATIONS

PCT/US2022/036257. International Search Report & Written Opinion (Dec. 12, 2022).
(Continued)

*Primary Examiner* — Peter J Macchiarolo
*Assistant Examiner* — Rodney T Frank
(74) *Attorney, Agent, or Firm* — LOZA & LOZA, LLP; Holly L. Rudnick

(57) ABSTRACT

Aspects relate to a compact and low-cost gas analyzer that can be used for different types of gas analysis, such as air quality analysis. The gas analyzer can include a light source, a gas cell configured to receive a sample (e.g., a gas under test), a spectral sensor including a spectrometer and a detector, and an artificial intelligence (AI) engine. Light can enter the gas cell and interact with the sample to produce output light that may be measured by the spectral sensor. The resulting spectrum produced by the spectral sensor may be analyzed by the AI engine to produce a result. The gas analyzer further includes a self-calibration component configured to enable calibration of the sample spectrum to compensate for spectral drift of the spectral sensor.

31 Claims, 41 Drawing Sheets

(52) U.S. Cl.
CPC ........... *G01N 21/3504* (2013.01); *G06N 3/02* (2013.01); *G01N 33/0068* (2024.05)

(58) Field of Classification Search
USPC .......................................................... 73/40.7
See application file for complete search history.

(56) References Cited

U.S. PATENT DOCUMENTS

| | | | |
|---|---|---|---|
| 2003/0038237 A1* | 2/2003 | Webber | G01N 21/3504 250/339.12 |
| 2007/0246653 A1* | 10/2007 | Zhou | G01J 3/027 250/339.1 |
| 2010/0282958 A1 | 11/2010 | Will et al. | |
| 2012/0033220 A1* | 2/2012 | Kotidis | G01N 21/35 356/445 |
| 2013/0003045 A1* | 1/2013 | Wilkins | G01N 21/031 356/402 |
| 2013/0120678 A1* | 5/2013 | Chao | F21K 9/60 977/774 |
| 2013/0166242 A1 | 6/2013 | Ido et al. | |
| 2015/0124257 A1* | 5/2015 | Scott | G01N 21/05 356/410 |
| 2016/0327479 A1* | 11/2016 | Feitisch | G01N 21/3504 |
| 2017/0059477 A1* | 3/2017 | Feitisch | G01J 3/42 |
| 2019/0301939 A1* | 10/2019 | Medhat | G01J 3/021 |
| 2020/0284654 A1* | 9/2020 | Sabry | G01J 3/0262 |
| 2021/0076941 A1 | 3/2021 | Van Laar | |

OTHER PUBLICATIONS

Elaraby et al. "Super-resolution infrared spectroscopy for gas analysis using convolutional neural networks." Proceedings of SPIE vol. 11511 (Aug. 20, 2020).

Esler et al. "Precision Trace Gas Analysis by FT-IR Spectroscopy. 1. Simultaneous Analysis of CO2, CH4, N2O, and CO in Air." Analytical Chemistry, vol. 72, No. 1 (Jan. 1, 2000).

Lancaster et al. "Real-time measurements of trace gases using a compact difference-frequency-based sensor operating at 3.5 μm." Appl. Phys. B Lasers and Optics, 67, 339-345 (1998).

Tang et al. "On-line multi-component alkane mixture quantitative analysis using Fourier transform infrared spectrometer." Chemometrics and Intelligent Laboratory Systems 146, p. 371-377 (Jun. 20, 2015).

Xiao Liu, Sitian Cheng, Hong Liu, Sha Hu, Daqiang Zhang and Huansheng Ning, "A Survey on Gas Sensing Technology," Sensors 2012.

https://en.wikipedia.org/wiki/Multipass_spectroscopic_absorption_cells#/Herriott_cell, obtained on May 16, 2022.

D. Perez-Guaita, J. Kuligowski, G. Quintas, S. Garrigues, M. de la Guardiaa, Atmospheric Compensation in Fourier Transform Infrared (FT-IR) Spectra of Clinical Samples, Applied Spectroscopy, vol. 67, No. 11, 2013.

P. R. Griffiths and J. A. de Haseth, Fourier Transform Infrared Spectrometry, 2nd edition, John Wiley & Sons, 2007.

L.S. Rothman et al,"The HITRAN2012 molecular spectroscopic database",Journal of Quantitative Spectroscopy &Radiative Transfer,130 (2013) 4-50.

Invitation to Pay Additional Fees, PCT/US2022/036257, dated Oct. 10, 2022, 12 pgs.

Lancaster D G et al. "Real-Time Measurements of Trace Gases Using a Compact Difference-Frequency-Based Sensor Operating at 3.5 MUM", Applied Physics B, Springer Berlin Heidelberg, Berlin/Heidelberg, vol. B67, No. 3, (Sep. 1, 1998), pp. 339-345.

\* cited by examiner

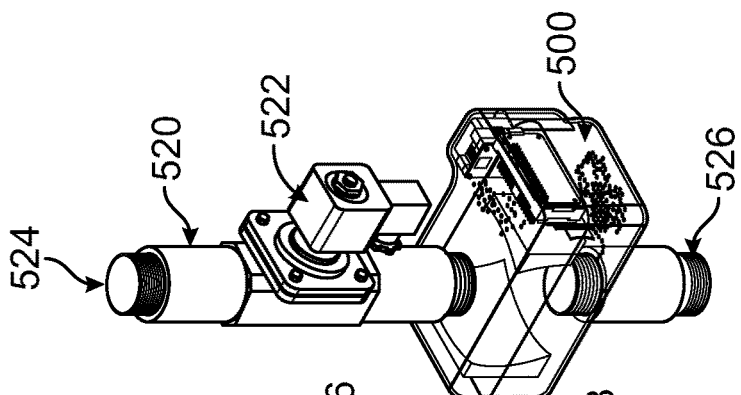
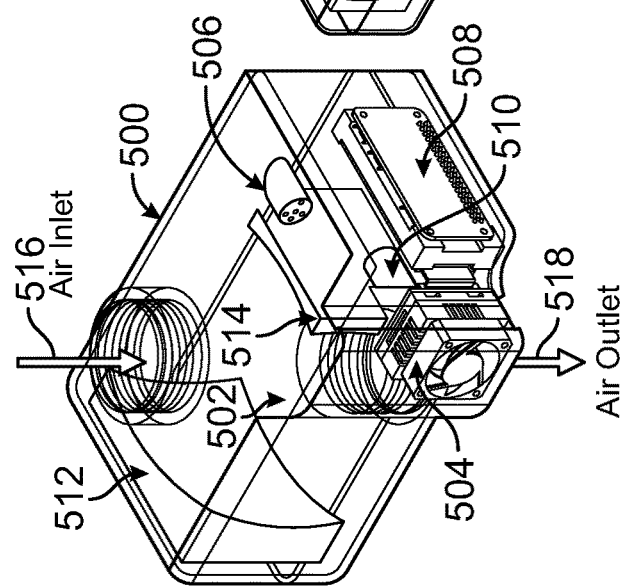
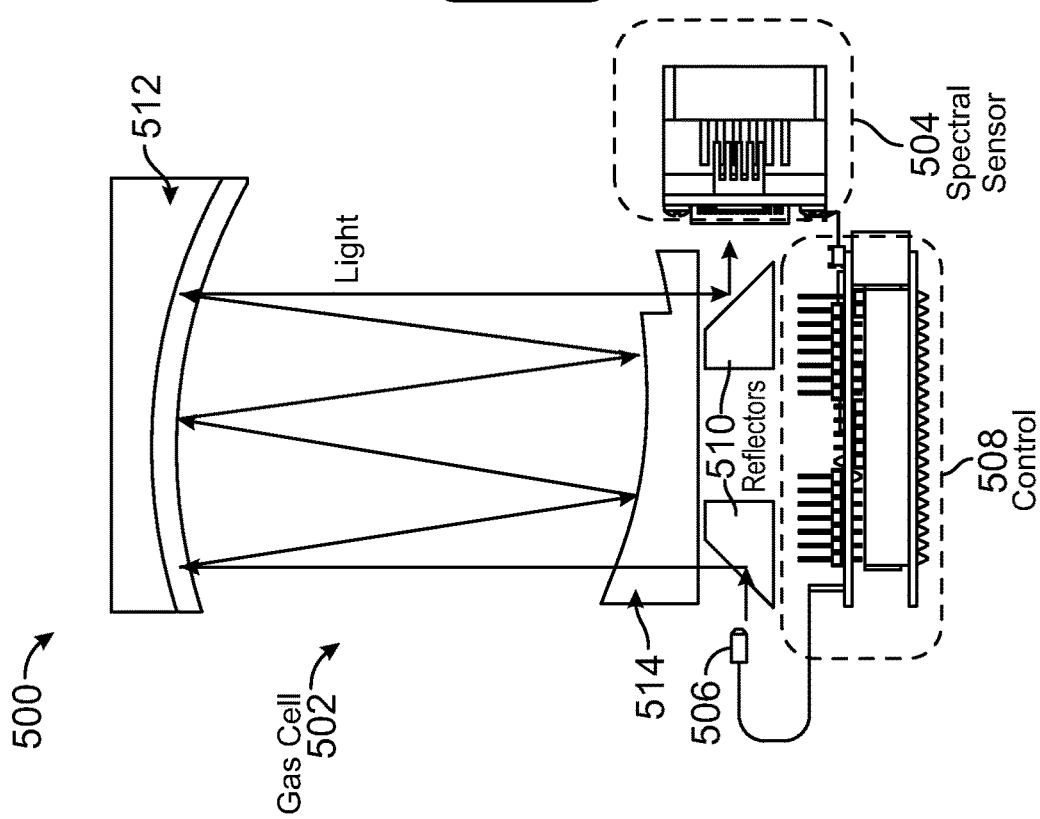
FIG. 5C
FIG. 5B
FIG. 5A

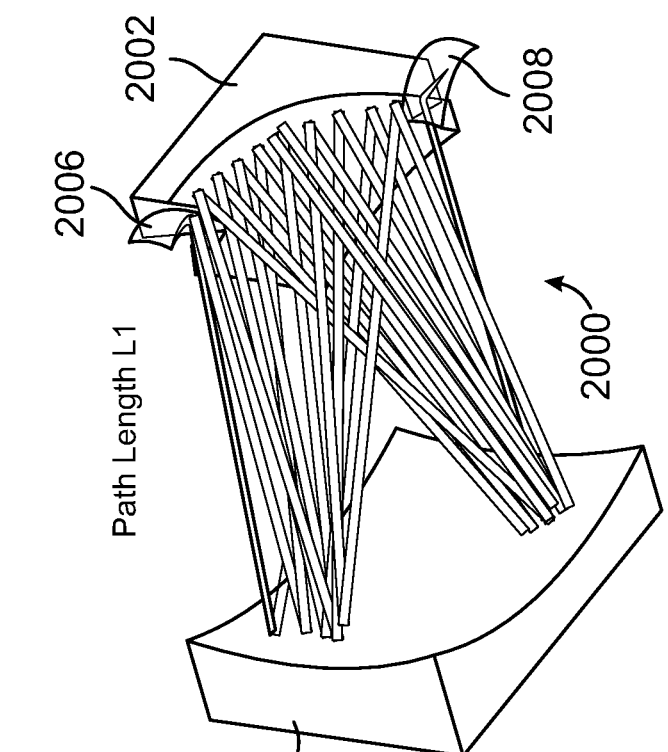
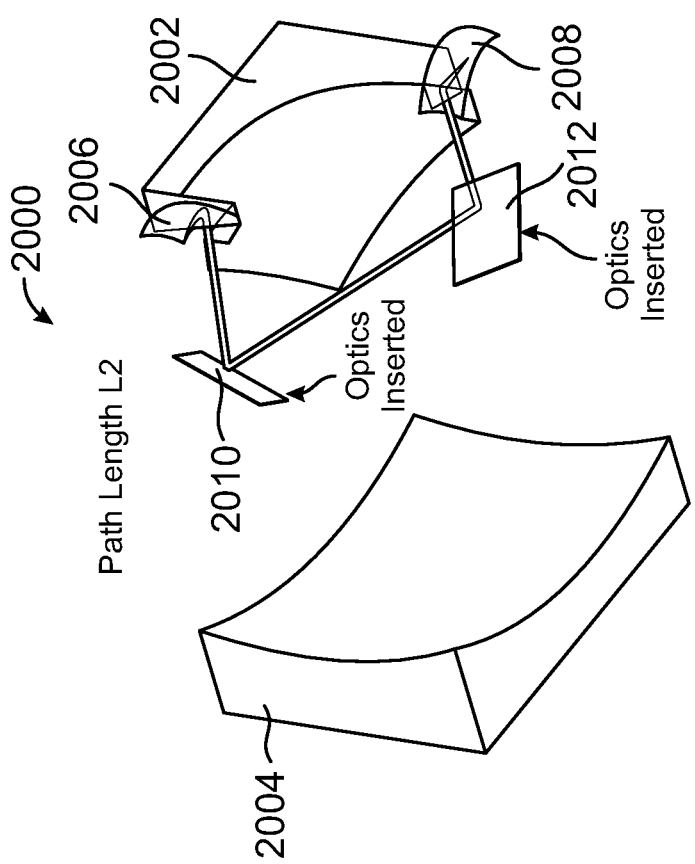

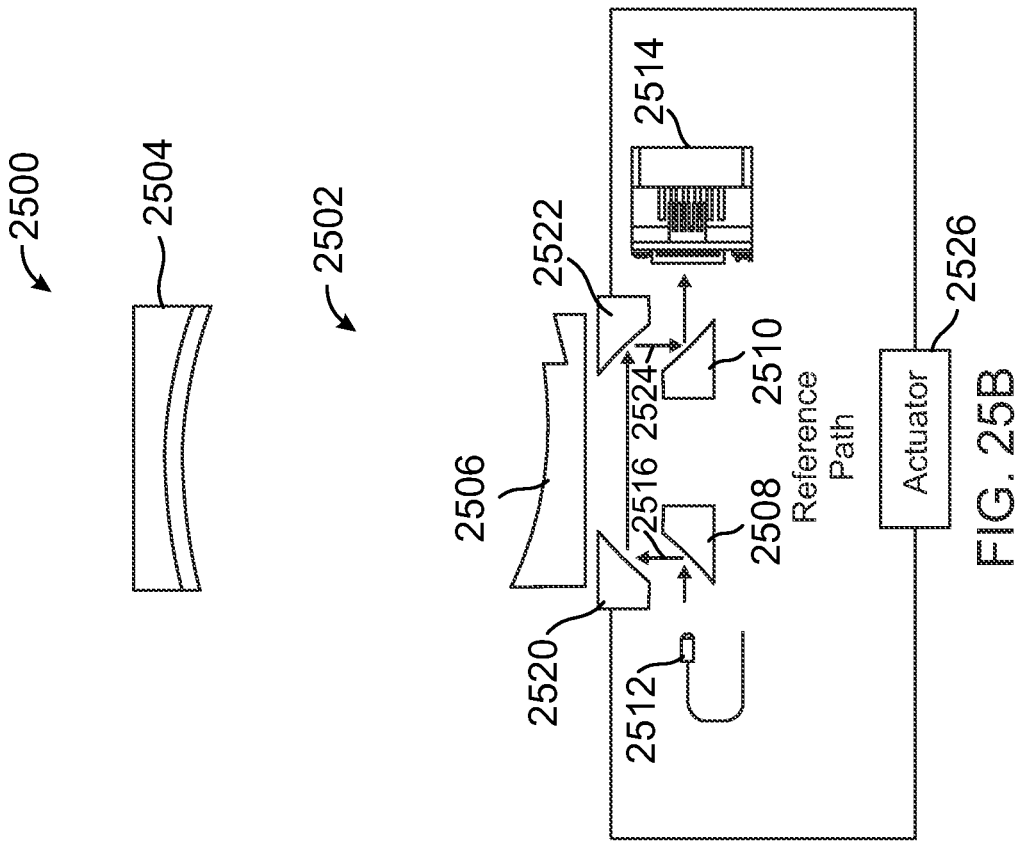
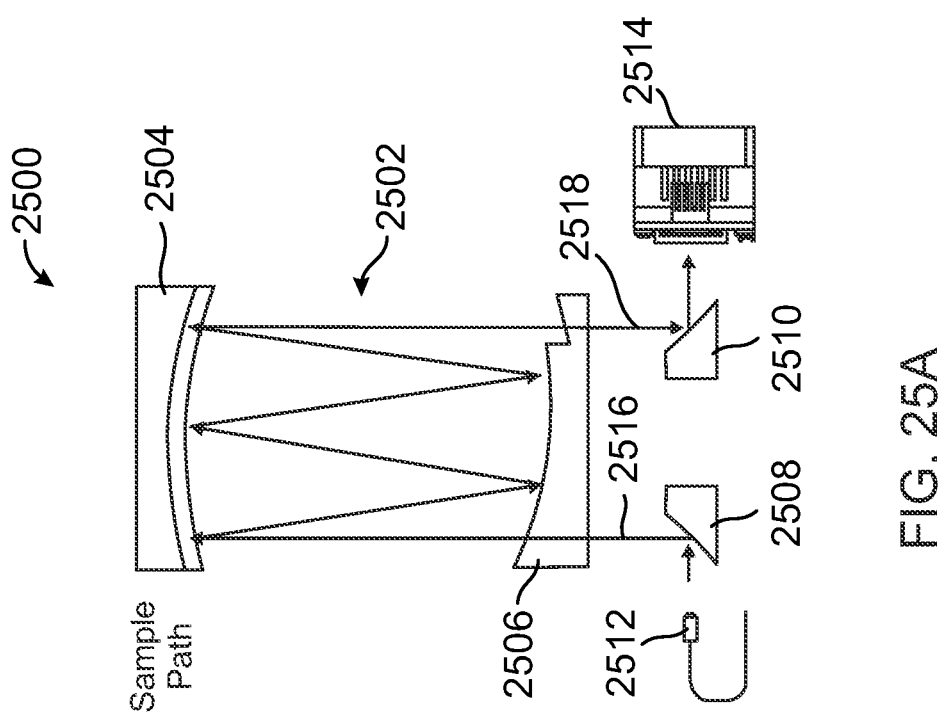
FIG. 25A
FIG. 25B

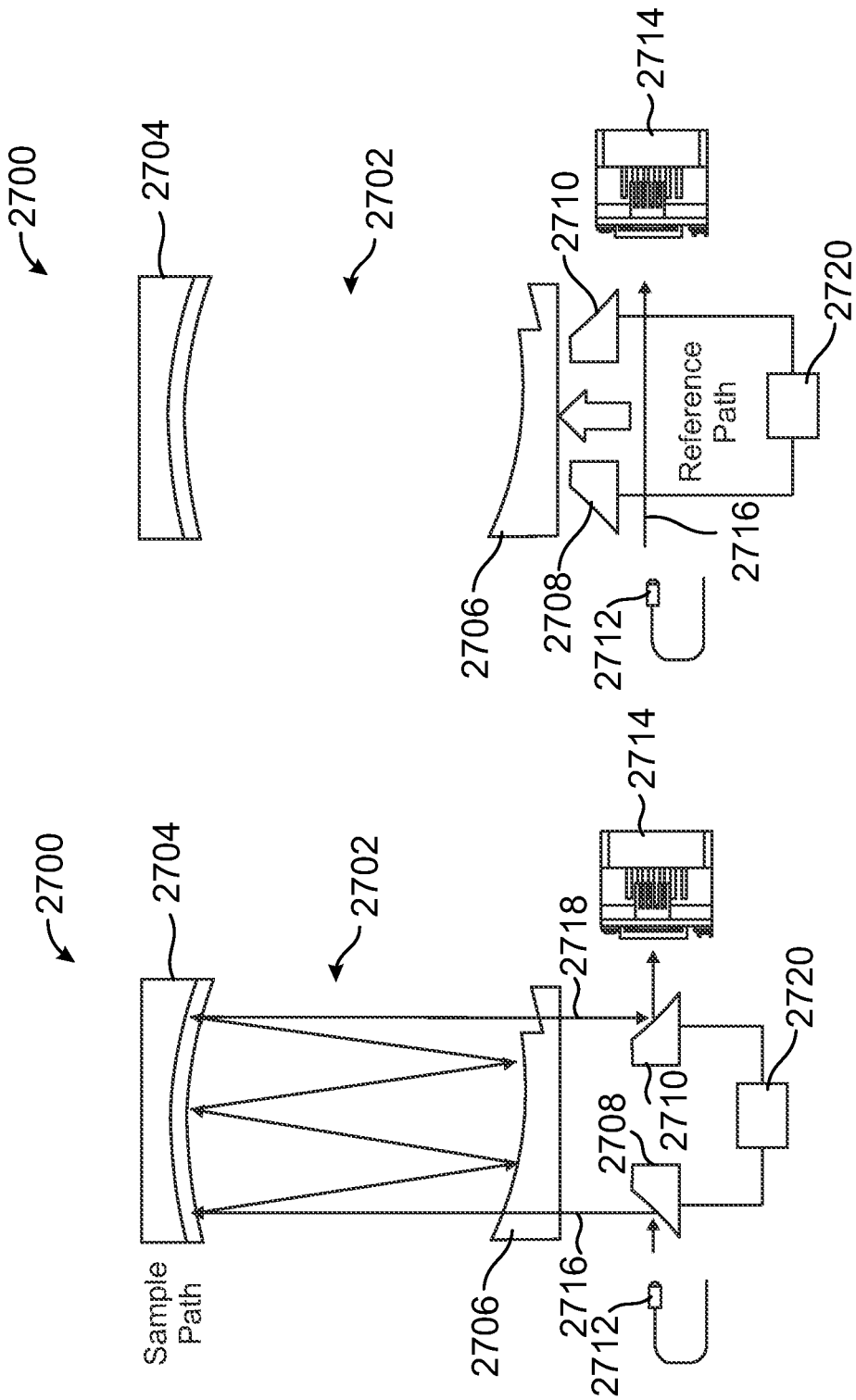

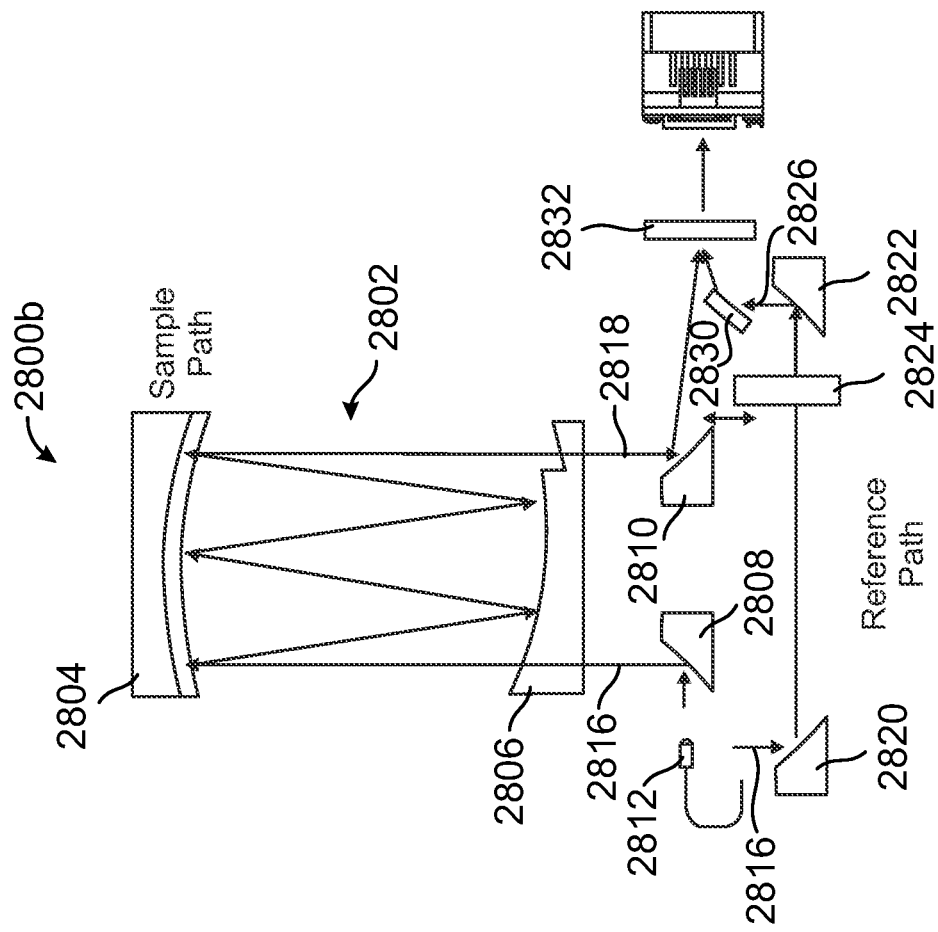
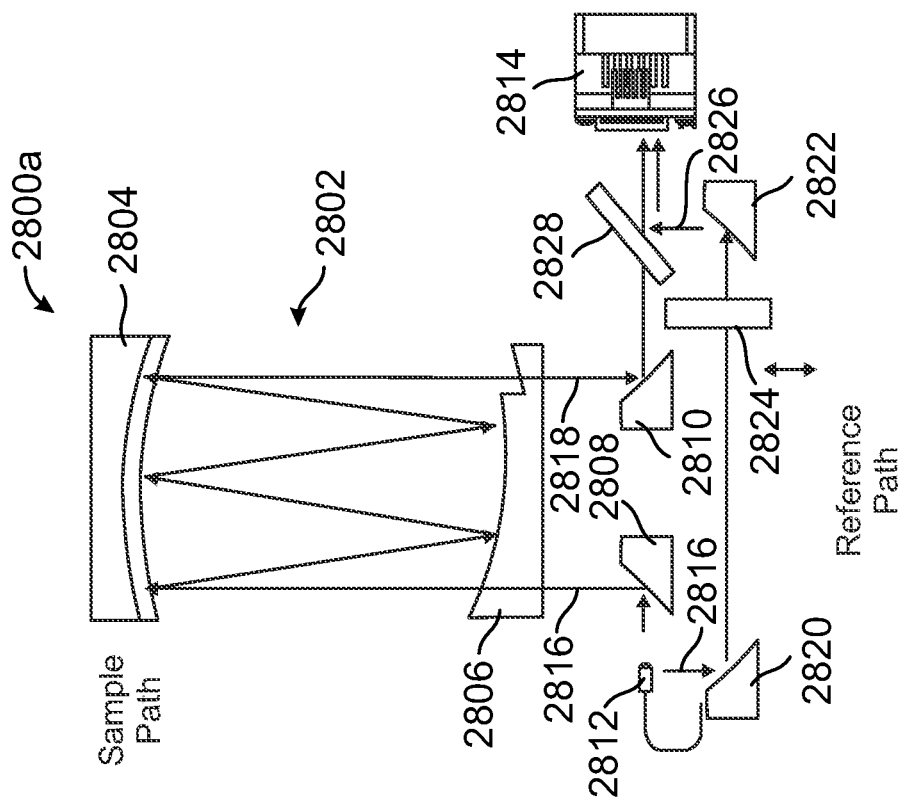
FIG. 28B
FIG. 28A

SELF-CALIBRATED SPECTROSCOPIC AND AI-BASED GAS ANALYZER

PRIORITY CLAIM

This application claims priority to and the benefit of Provisional Application No. 63/218,885, filed in the U.S. Patent and Trademark Office on Jul. 6, 2021, the entire content of which is incorporated herein by reference as if fully set forth below in its entirety and for all applicable purposes.

TECHNICAL FIELD

The technology discussed below relates generally to spectroscopic-based gas analysis, and in particular to a spectroscopic artificial intelligence (AI)-based gas analyzer that is self-calibrated.

BACKGROUND

Various technologies have been developed for gas sensing, including for example, technologies based on metal oxide semiconductor, polymer, carbon nanotubes, moisture absorption material, optical methods, calorimetric methods, gas chromatography and acoustic methods. Optical methods may be based on spectroscopy, interferometry, or ellipsometry, where the sensing occurs for the refractive index, absorbance and/or fluorescence properties of the analyte molecules or a chemo-optical transducing element. Multi-pass gas cells may be used in optical methods to increase the path length and improve the limit of detection. Examples of multi-pass gas cells include, but are not limited to, White cells, Herriot cells, Pfund cells, and circular cells. Optical methods provide an advantage over other technologies with respect to sensitivity, response time, and the ability to detect a wide range of gases. However, optical methods can suffer from challenges related to the production cost of the optical sensor and the size of the volume optics components used in the analyzing system.

To identify a gas sample under test (SUT) using optical methods, a background measurement (e.g., a background spectrum) is typically obtained and compared to a sample measurement (e.g., a sample spectrum) in order to abstract the specific gases absorptions from the sample measurement. The background measurement is usually performed before acquiring the spectrum of the sample. The background measurement does not contain any gases absorption, and as such, the background measurement can account for the transfer function of the measurement system, which may include, for example, a light source, a spectrometer, a detector and an optical coupling system. A challenge in obtaining background measurements involves evacuating the gas cell before each sample measurement to acquire the background spectrum, which may not be practical, for example, in examples in which the system is configured to obtain continuous measurements of gases flowing through the system.

In one example, the background measurement of a reference gas cell may be obtained at the same time as a sample measurement of a different sample gas cell containing the sample under test. For example, the background measurement and sample measurement may be performed in parallel either using two separate spectrometers and detectors or using the same spectrometer and detector. As another example, the reference gas cell and the sample gas cell can be measured in series with a condition that the reference gas cell is filled with a non-interfering gas with the sample. However, this architecture requires the use of two different gas cells placed in parallel or in series with one another.

In addition to the challenge of background measurements, the presence of mid-infrared (mid-IR) absorbing molecules in the atmosphere, such as water ($H_2O$) and carbon dioxide ($CO_2$), further presents a challenge of infrared (IR) spectroscopy in the open environment because the spectral contribution of atmospheric gases can hinder the accurate identification and quantification of target analytes. This problem is significant for water vapor as it has several strong absorption bands in the infrared region that overlap those of the target gases. There are two main challenges for the compensation of the absorption of water. The first challenge is that there is a non-linear relation between measured absorbance and true absorbance at low resolution and high absorbance. Therefore, the spectrum cannot simply be scaled by a factor with an assumption that this scaling factor accounts for the concentration change. The second challenge is that the water absorption spectrum is significantly dependent on environmental conditions, such as the temperature and pressure change.

SUMMARY

The following presents a summary of one or more aspects of the present disclosure, in order to provide a basic understanding of such aspects. This summary is not an extensive overview of all contemplated features of the disclosure, and is intended neither to identify key or critical elements of all aspects of the disclosure nor to delineate the scope of any or all aspects of the disclosure. Its sole purpose is to present some concepts of one or more aspects of the disclosure in a form as a prelude to the more detailed description that is presented later.

In an example, a self-calibrated and AI-based gas analyzer is disclosed. The gas analyzer includes a light source configured to produce incident light and a gas cell configured to receive a sample. The gas cell is further configured to receive input light corresponding to the incident light or an interference beam produced based on the incident light and to produce output light based on light interaction with the sample within the gas cell in a measurement mode. The gas analyzer further includes a spectral sensor including a spectrometer configured to receive the incident light from the light source or the output light from the gas cell and further configured to produce the interference beam, where the interference beam corresponds to the input light or is produced based on the output light. The spectral sensor further includes a detector configured to obtain a sample spectrum of the sample based on the interference beam. The gas analyzer further includes an artificial intelligence engine configured to receive the sample spectrum and to generate a result indicative of at least one parameter associated with the sample based on the sample spectrum, control circuitry configured to control the light source and the spectral sensor, and a self-calibration component configured to enable calibration of the sample spectrum to compensate for spectral drift of the spectral sensor.

These and other aspects of the invention will become more fully understood upon a review of the detailed description, which follows. Other aspects, features, and embodiments of the present invention will become apparent to those of ordinary skill in the art, upon reviewing the following description of specific, exemplary embodiments of the present invention in conjunction with the accompanying figures. While features of the present invention may be discussed relative to certain embodiments and figures below, all embodiments of the present invention can include one or more of the advantageous features discussed herein. In other words, while one or more embodiments may be discussed as having certain advantageous features, one or more of such features may also be used in accordance with the various embodiments of the invention discussed herein. In similar fashion, while exemplary embodiments may be discussed below as device, system, or method embodiments it should be understood that such exemplary embodiments can be implemented in various devices, systems, and methods.

BRIEF DESCRIPTION OF THE DRAWINGS

FIGS. 5A-5C are diagrams illustrating another example of a gas analyzer according to some aspects.

FIGS. 20A and 20B are diagrams illustrating an example of a modified Herriot gas cell including a self-calibration component according to some aspects.

FIGS. 25A and 25B are diagrams illustrating an exemplary gas analyzer including a self-calibration component external to the gas cell according to some aspects.

FIGS. 27A and 27B are diagrams illustrating another exemplary gas analyzer including a self-calibration component external to the gas cell according to some aspects.

FIGS. 28A and 28B are diagrams illustrating other exemplary gas analyzer configurations including a self-calibration component external to the gas cell according to some aspects.

DETAILED DESCRIPTION

Figure 1:
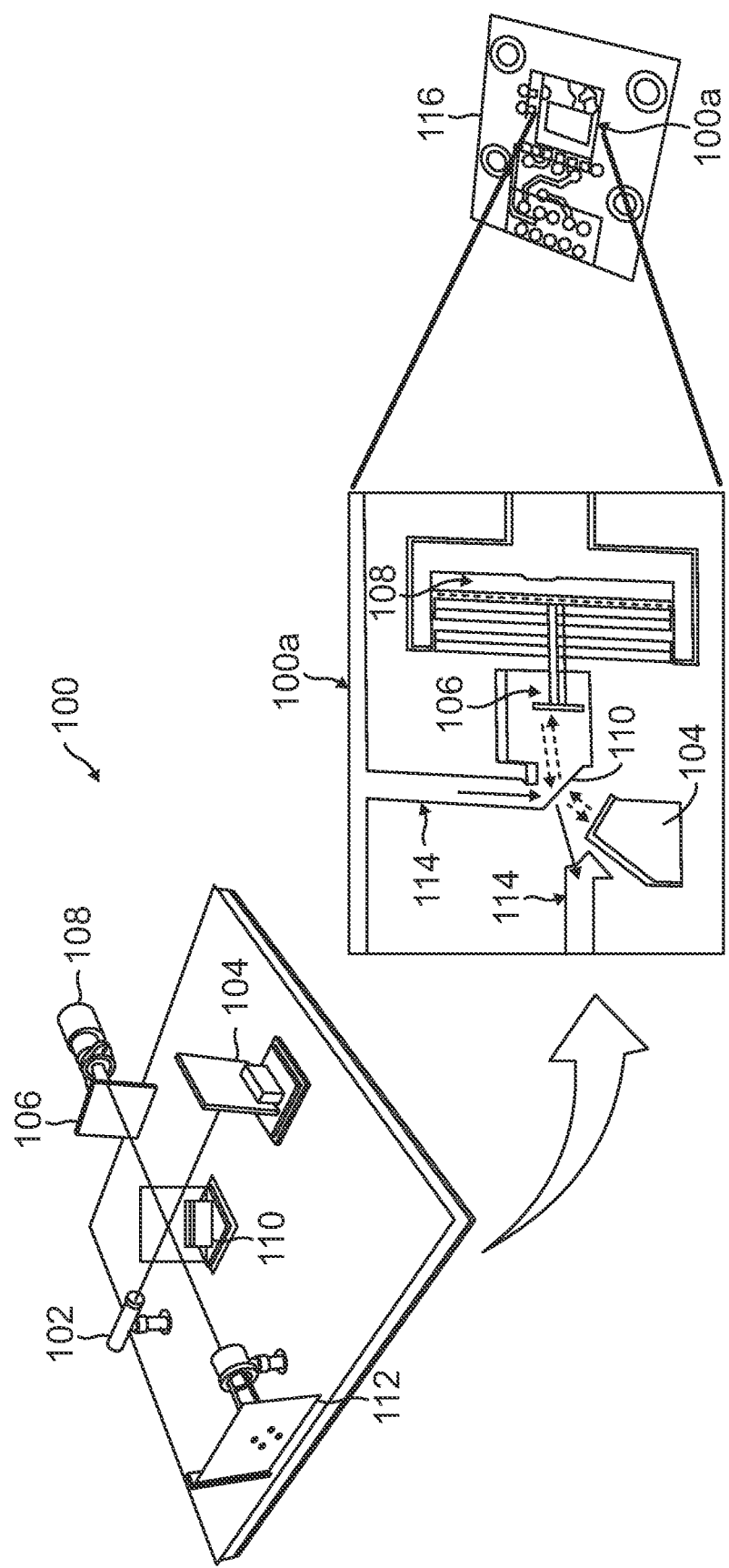
FIG. 1 is a diagram illustrating a spectrometer according to some aspects.

The detailed description set forth below in connection with the appended drawings is intended as a description of various configurations and is not intended to represent the only configurations in which the concepts described herein may be practiced. The detailed description includes specific details for the purpose of providing a thorough understanding of various concepts. However, it will be apparent to those skilled in the art that these concepts may be practiced without these specific details. In some instances, well known structures and components are shown in block diagram form in order to avoid obscuring such concepts.

Various aspects of the disclosure relate to a compact and low-cost gas analyzer that can be used for different types of gas analysis, such as air quality analysis. The core of the gas analyzer is a spectroscopic device that is capable of obtaining a spectrum of light over a wideband for multi-material detection. For example, the gas analyzer can include a light source (e.g., a single broadband light source), a gas cell configured to receive a sample (e.g., a gas under test), a spectral sensor including a spectrometer and a detector (e.g., a single photodetector), and an artificial intelligence (AI) engine. In some examples, the gas cell can include an asymmetric Herriot gas cell in which the reflectors each have a different radius of curvature. Other types of gas cells, including White gas cells and circular gas cells may also be used.

Light can enter the gas cell and interact with the sample to produce output light that may be measured by the spectral sensor. In one example, the incident light produced by the light source may enter the gas cell as input light and the output light from the gas cell may be input to the spectrometer to produce an interference beam that may be detected by the detector. In another example, the incident light produced by the light source may be directed towards the spectrometer and the resulting interference beam may be input to the gas cell as the input light. In this example, the output light from the gas cell may be directed to the detector. The resulting spectrum produced by the spectral sensor may be analyzed by the AI engine to produce a result. For example, the AI engine may deduce the quality of air and trigger or initiate an action based on the analysis results.

The gas analyzer further includes a self-calibration component configured to enable calibration of the sample spectrum without using a reference gas cell to compensate for spectral drift of the spectral sensor without the need for a separate reference gas cell or evacuating the sample under test from the sample gas cell to obtain a background measurement. In some examples, the self-calibration component includes additional optical elements configured to redirect light through the gas cell without reflecting off the gas cell reflector(s) or to redirect light outside of the gas cell for input to the spectrometer. In other examples, the self-calibration component includes a moveable reflector within the gas cell that can be moveable between a first position at which a sample measurement is obtained and a second position at which a reference spectrum is obtained. In other examples, the self-calibration component may include a reflective material attached to a solenoid external to a circular gas cell, where the solenoid is configured to move the reflective material into and out of the light path of light directed into the circular gas cell to obtain a sample spectrum and a reference spectrum. In other examples, the self-calibration component is included within the AI engine. In still other examples, the self-calibration component may include a bandpass filter configured to be inserted at the output of the gas cell. In further examples, the self-calibration component can be included within the spectrometer.

Using the gas analyzer device described herein, different aspects of air quality can be analyzed, including, for example, the concentration of volatile organic compounds (VOCs), or the detection, classification and quantification of odor types, among many different applications. The gas analyzer device further provides a modular approach in which additional sensors (e.g., physical or chemical sensors) assisting the spectral analyzer can be co-integrated in the analyzer. In addition, the gas analyzer device may further include an atmospheric compensation unit configured to reduce or eliminate the effect of the presence of undesired substances (e.g., $H_2O$ or $CO_2$) in the gas cell. For example, the atmospheric compensation unit may include filters for filtering the undesired substances before entering the gas cell. In other examples, the atmospheric compensation unit may be implemented within the AI engine or spectrometer, where different apodizations may be used. In still other examples, the atmospheric compensation unit may include one or more sensors to measure the undesired substance concentration, the temperature of the gas cell, and/or the pressure in the gas cell, so the substances can be deduced and subtracted from the measured spectrum using the AI engine based on a database.

The gas analyzer can be operated in different manners, such as mounting the gas analyzer in locations in which natural air flow leads force the air to enter and exit the gas cell. In other examples, the gas cell may be working in an inline operation or the gas analyzer can be equipped with a pump for generating the air flow and controlling the pressure of the air in the system. The gas analyzer may further be mounted in one or more locations in a heating, ventilation, and air conditioning (HVAC) system to monitor the air quality in different portions of the system. In addition, the gas analyzer can be mounted in vehicles for monitoring the air inside the car or monitoring the outdoor air in the environment. A network of the gas analyzers, together with a cloud-based AI engine, could be used to provide mapping of gas concentrations, based on numerical modeling of gas dispersion and the assimilation of the collected measured data.

FIG. 1 is a diagram illustrating a spectrometer 100 according to some aspects. The spectrometer 100 may be, for example, a Fourier Transform infrared (FTIR) spectrometer. In the example shown in FIG. 1, the spectrometer 100 is a Michelson FTIR interferometer. In other examples, the spectrometer may include an FTIR Fabry-Perot interferometer.

FTIR spectrometers measure a single-beam spectrum (power spectral density (PSD)), where the intensity of the single-beam spectrum is proportional to the power of the radiation reaching the detector. In order to measure the absorbance of a sample, the background spectrum (i.e., the single-beam spectrum in absence of a sample) may first be measured to compensate for the instrument transfer function. The single-beam spectrum of light transmitted or reflected from the sample may then be measured. The absorbance of the sample may be calculated from the transmittance, reflectance, or trans-reflectance of the sample. For example, the absorbance of the sample may be calculated as the ratio of the spectrum of transmitted light, reflected light, or trans-reflected light from the sample to the background spectrum.

The interferometer 100 includes a fixed mirror 104, a moveable mirror 106, a beam splitter 110, and a detector 112 (e.g., a photodetector). A light source 102 associated with the spectrometer 100 is configured to emit an input beam and to direct the input beam towards the beam splitter 110. The light source 102 may include, for example, a laser source, one or more wideband thermal radiation sources, or a quantum source with an array of light emitting devices that cover the wavelength range of interest.

The beam splitter 110 is configured to split the input beam into two beams. One beam is reflected off of the fixed mirror 104 back towards the beam splitter 110, while the other beam is reflected off of the moveable mirror 106 back towards the beam splitter 110. The moveable mirror 106 may be coupled to an actuator 108 to displace the movable mirror 106 to the desired position for reflection of the beam. An optical path length difference (OPD) is then created between the reflected beams that is substantially equal to twice the mirror 106 displacement. In some examples, the actuator 108 may include a micro-electro-mechanical systems (MEMS) actuator, a thermal actuator, or other type of actuator.

The reflected beams interfere at the beam splitter 110 to produce an output light beam, allowing the temporal coherence of the light to be measured at each different Optical Path Difference (OPD) offered by the moveable mirror 106. The signal corresponding to the output light beam may be detected and measured by the detector 112 at many discrete positions of the moveable mirror 106 to produce an interferogram. In some examples, the detector 112 may include a detector array or a single pixel detector. The interferogram data verses the OPD may then be input to a processor (not shown, for simplicity). The spectrum may then be retrieved, for example, using a Fourier transform carried out by the processor.

In some examples, the interferometer 100 may be implemented as a MEMS interferometer 100a (e.g., a MEMS chip). The MEMS chip 100a may then be attached to a printed circuit board (PCB) 116 that may include, for example, one or more processors, memory devices, buses, and/or other components. In some examples, the PCB 116 may include a spectrum analyzer, such as an AI engine, configured to receive and process the spectrum. As used herein, the term MEMS refers to the integration of mechanical elements, sensors, actuators and electronics on a common silicon substrate through microfabrication technology. For example, the microelectronics are typically fabricated using an integrated circuit (IC) process, while the micromechanical components are fabricated using compatible micromachining processes that selectively etch away parts of the silicon wafer or add new structural layers to form the mechanical and electromechanical components. One example of a MEMS element is a micro-optical component having a dielectric or metallized surface working in a reflection or refraction mode. Other examples of MEMS elements include actuators, detector grooves and fiber grooves.

In the example shown in FIG. 1, the MEMS interferometer 100a may include the fixed mirror 104, moveable mirror 106, beam splitter 110, and MEMS actuator 108 for controlling the moveable mirror 106. In addition, the MEMS interferometer 100a may include fibers 114 for directing the input beam towards the beam splitter 110 and the output beam from the beam splitter 110 towards the detector (e.g., detector 112). In some examples, the MEMS interferometer 100a may be fabricated using a Deep Reactive Ion Etching (DRIE) process on a Silicon On Insulator (SOI) wafer in order to produce the micro-optical components and other MEMS elements that are able to process free-space optical beams propagating parallel to the SOI substrate. For example, the electro-mechanical designs may be printed on masks and the masks may be used to pattern the design over the silicon or SOI wafer by photolithography. The patterns may then be etched (e.g., by DRIE) using batch processes, and the resulting chips (e.g., MEMS chip 100a) may be diced and packaged (e.g., attached to the PCB 116).

For example, the beam splitter 110 may be a silicon/air interface beam splitter (e.g., a half-plane beam splitter) positioned at an angle (e.g., 45 degrees) from the input beam. The input beam may then be split into two beams L1 and L2, where L1 propagates in air towards the moveable mirror 106 and L2 propagates in silicon towards the fixed mirror 104. Here, L1 originates from the partial reflection of the input beam from the half-plane beam splitter 110, and thus has a reflection angle equal to the beam incidence angle. L2 originates from the partial transmission of the input beam through the half-plane beam splitter 110 and propagates in silicon at an angle determined by Snell's Law. In some examples, the fixed and moveable mirrors 104 and 106 are metallic mirrors, where selective metallization (e.g., using a shadow mask during a metallization step) is used to protect the beam splitter 110. In other examples, the mirrors 104 and 106 are vertical Bragg mirrors that can be realized using, for example, DRIE.

In some examples, the MEMS actuator 108 may be an electrostatic actuator formed of a comb drive and spring. For example, by applying a voltage to the comb drive, a potential difference results across the actuator 108, which induces a capacitance therein, causing a driving force to be generated as well as a restoring force from the spring, thereby causing a displacement of moveable mirror 106 to the desired position for reflection of the beam back towards the beam splitter 110.

The unique information from the vibrational absorption bands of a molecule is reflected in an infrared spectrum that may be produced, for example, by the spectrometer 100 shown in FIG. 1. By applying spectral numerical processing and statistical analysis to a spectrum, the information in the spectrum may be identified or otherwise classified. The application of statistical methods to the analysis of experimental data is traditionally known as chemometrics, and more recently as artificial intelligence.

Figure 2:
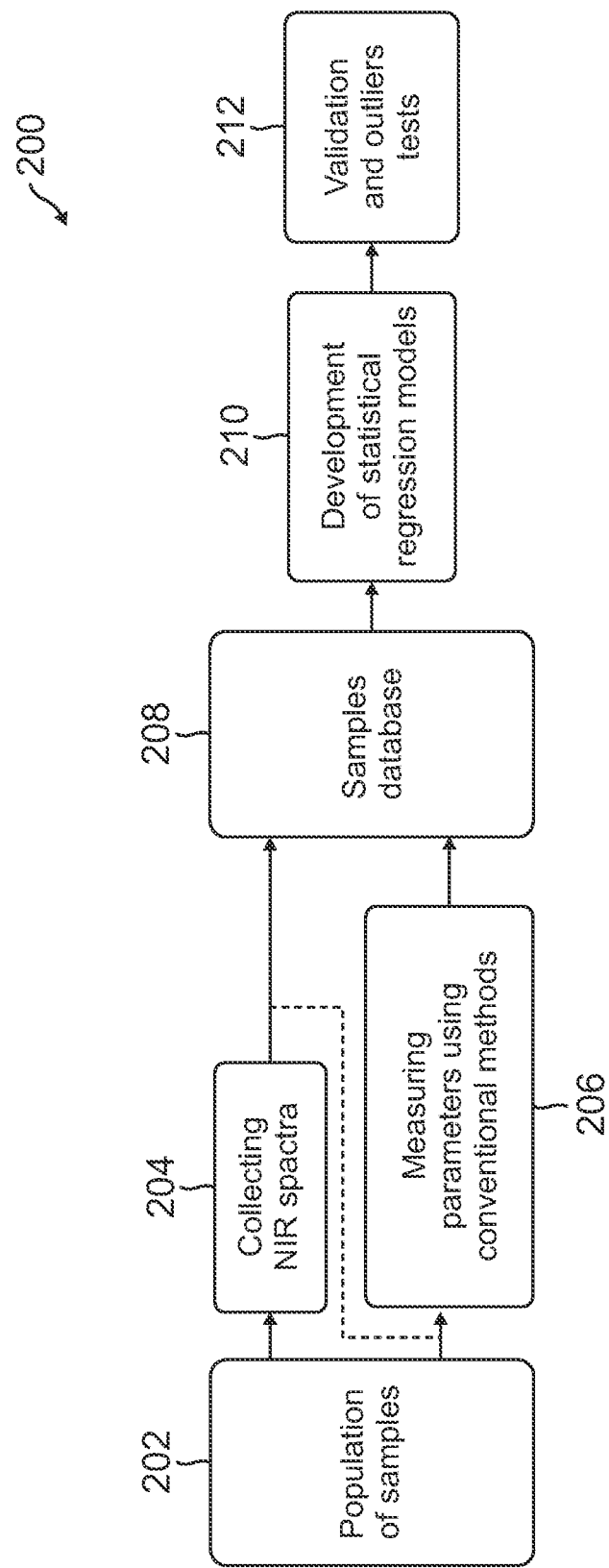
FIG. 2 illustrates an example of a workflow for building an AI engine according to some aspects.

FIG. 2 illustrates an example of a workflow 200 for building an AI engine according to some aspects. To begin building the AI engine, a group or population of samples 202 is obtained for measurements by a spectrometer, such as the spectrometer 100 shown in FIG. 1, to produce spectra 204. At the same time, these samples 202 can also be measured by conventional methods and the values recorded as reference values 206. These reference values 206 together with the spectra 204 form a samples database 208 that is used to teach the AI engine (e.g., machine learning) how to interpret the spectra and transform the spectra to certain values (e.g., results). For example, the samples database 208 may be used in the development of statistical regression models (e.g., calibration models) 210 that may then be applied to a spectrum of a sample to produce a result associated with the sample. Validation and outliers detection 212 of the test results may then be performed to refine the calibration model(s).

Since the spectrum produced by infrared (IR) spectroscopy are instantaneous, unlike conventional analysis methods, there is no need to wait for certain transformations (e.g., chemical transformations) to occur within the sample. Different physical and chemical parameters of the sample can be analyzed with a single scan.

Figure 3:
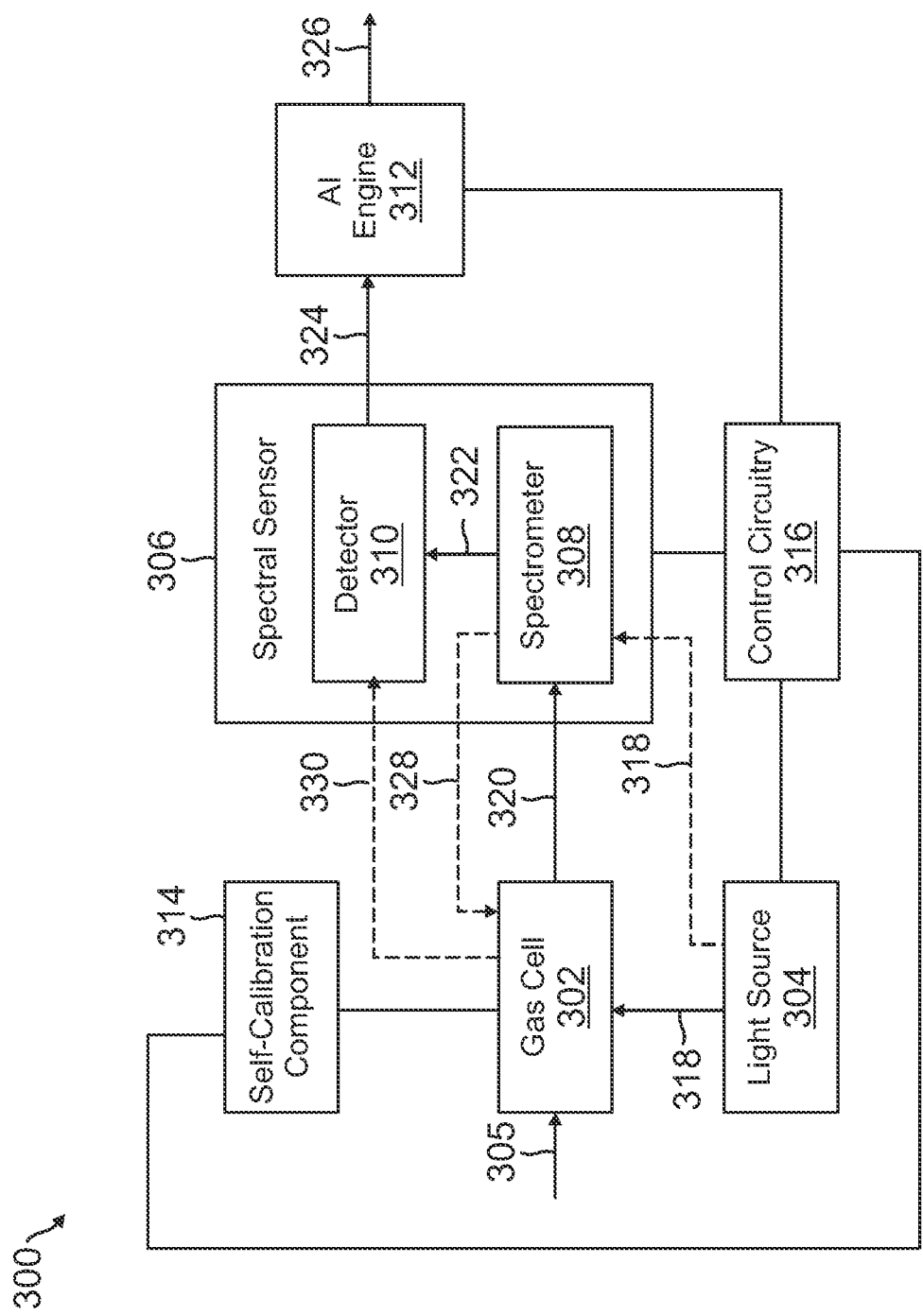
FIG. 3 is a diagram illustrating an example of a gas analyzer according to some aspects.

FIG. 3 is a diagram illustrating an example of a gas analyzer 300 according to some aspects. The gas analyzer 300 includes a gas cell 302, a light source 304, a spectral sensor 306, an artificial intelligence (AI) engine 312, a self-calibration component 314, and control circuitry 316.

The control circuitry 316 may include, for example, one or more processor(s). For example, the processor(s) may include a single processing device or a plurality of processing devices. Such a processing device may be a microprocessor, micro-controller, digital signal processor, microcomputer, central processing unit, field programmable gate array, programmable logic device, logic circuitry, analog circuitry, digital circuitry, and/or any device that manipulates signals (analog and/or digital) based on hard coding of the circuitry and/or operational instructions. The control circuitry 316 may further include a memory, which may be a single memory device, a plurality of memory devices, and/or embedded circuitry of the processor. Such a memory device may be a read-only memory, random access memory, volatile memory, non-volatile memory, static memory, dynamic memory, flash memory, cache memory, and/or any device that stores digital information, including instructions (e.g., code) that may be executed by the processor.

The spectral sensor 306 includes a spectrometer 308 and a detector 310. The spectrometer 308 may include, for example, a Michelson interferometer, a Fabry-Perot cavity, or one more of light filters diffraction gratings, spatial light modulators, or birefringent devices. In some examples, the spectrometer 308 includes a MEMS interference device, such as the MEMS FTIR based spectrometer, as shown in FIG. 1. The MEMS interferometer enables generating a spectrum in millisecond time scale since the moving micromirror is driven by a MEMS actuator. The detector 310 may include, for example, a single photodetector. The light source(s) 304 may include, for example, a laser source or wideband source. In some examples, the light source(s) 304 may be infrared or near-infrared light source(s). In an example, the light source 304 may include a single broadband light source.

The gas cell 302 may be configured to receive a sample (e.g., a gas under test) 305, such as air. The gas cell 302 may include, for example, a White cell (e.g., including three reflectors, such as three mirrors), a Herriot cell (e.g., including two reflectors, such as two mirrors), a Pfund cell, or a circular cell. The Herriot cell may be simpler than the White cell in that the Herriot cell includes only two mirrors and is less susceptible to mechanical disturbance of the cell. However, the Herriot cell may not accept high numerical aperture beams, and larger sized mirrors may be used when long path lengths are needed.

The light source(s) 304 can be configured to generate incident light 318. In some examples, as shown in FIG. 3, the incident light 318 from the light source 304 may be directed into the gas cell (e.g., via one or more optical coupling elements, not shown) as input light. The gas cell 302 is a multi-pass gas cell configured to produce output light 320 based on light interaction with the sample via multiple reflections of the light within the gas cell 302. The output light 320 may then be input to the spectrometer 308, which is configured to produce an interference beam 322 based on the output light 320. The interference beam 322 may be received by the detector 310, which may be configured to obtain a spectrum 324 of the sample based on the interference beam 322.

In other examples (shown by the dotted lines in FIG. 3), the incident light 318 from the light source 304 may first be input to the spectrometer 308. In this example, an interference beam 328 produced by the spectrometer 308 may be directed to the gas cell 302 as the input light that interacts with the sample via multiple reflections of light within the gas cell 302 to produce output light 330. The output light 330 may then be detected by the detector 310 to obtain the spectrum 324 of the sample. In this configuration, the detector 310 can be detachable and replaced for modularity. The wavelength range of the spectral sensor 306 can be changed by changing the detector 310. In addition, different cooling options for the detector 310, such as one, two, three or four stages of cooling can be selected and used.

The spectrum 324 may be input to the AI engine 312 for analysis and processing. The AI engine 312 is configured to process the spectrum 324 to generate a result 326 indicative of at least one parameter associated with the sample based on the spectrum 324. For example, the AI engine 312 may include one or more processors for processing the spectrum 324 and a memory configured to store one or more calibration models utilized by the processor in processing the spectrum. In some examples, the result 326 corresponds to an action that is triggered or initiated based on the analysis of the spectrum 324. For example, the action may include sending an alert to a control center or operator, evacuating a building, turning off an HVAC unit, control access to a building or facility, allow a human subject to pass through a gate, or other suitable action. In some examples, the result 326 may correspond to different aspects of air quality: (1) the concentration of volatile organic compounds (VOCs); (2) detection, classification, and quantification of odor types and levels thereof; (3) olfactometric analysis; (4) detection of biomarkers; (5) detection of particulate matter; (6) $CO_2$ concentration, CO concentration, NOx concentration, water vapor concentration, or humidity, in addition to any other physical or chemical analytes.

The self-calibration component 314 may be configured to enable calibration of the sample spectrum 324 to compensate for spectral drift of the spectral sensor 306 without the use of a reference gas cell. In some examples, the self-calibration component 314 may facilitate self-referencing by enabling a reference spectrum (e.g., a background measurement) to be obtained by the detector 310 and input to the AI engine 312. In other examples, the self-calibration component 314 may be included within the AI engine 312. In still other examples, the self-calibration component 314 may be included within the spectrometer 308. In still other examples, the self-calibration component 314 may be configured to provide for self-correction of the spectrum 324 that may be used separate from or together with the self-referencing.

In an example operation, the control circuitry 316 can be configured to control the spectrometer 308 and the light source(s) 304 to initiate a measurement of a sample. For example, the control circuitry 316 can control the light source(s) 304 to generate and direct the incident light 318 to the gas cell 302 (or to the spectrometer 308). The control circuitry 316 can further be configured to control the spectrometer 308 and detector 310 to produce the interference beam and transmit the spectrum 324 to the AI engine 312. For example, the control circuitry 316 may be configured to power on/off the light source 304 and spectral sensor 306 and to provide other control signals to the light source 304 and the spectral sensor 306. In addition, the control circuitry 316 may be configured to control the AI engine 312 to perform a particular analysis and/or to produce a particular result (e.g., turn on or off an HVAC unit, etc.). The control circuitry 316 may further be configured to control the self-calibration component 314. For example, the control circuitry 316 may control the self-calibration component 314 to switch between a measurement mode in which the spectrum 324 of the sample within the gas cell is obtained and a calibration mode in which a reference spectrum (without the sample) is obtained.

Figure 4:
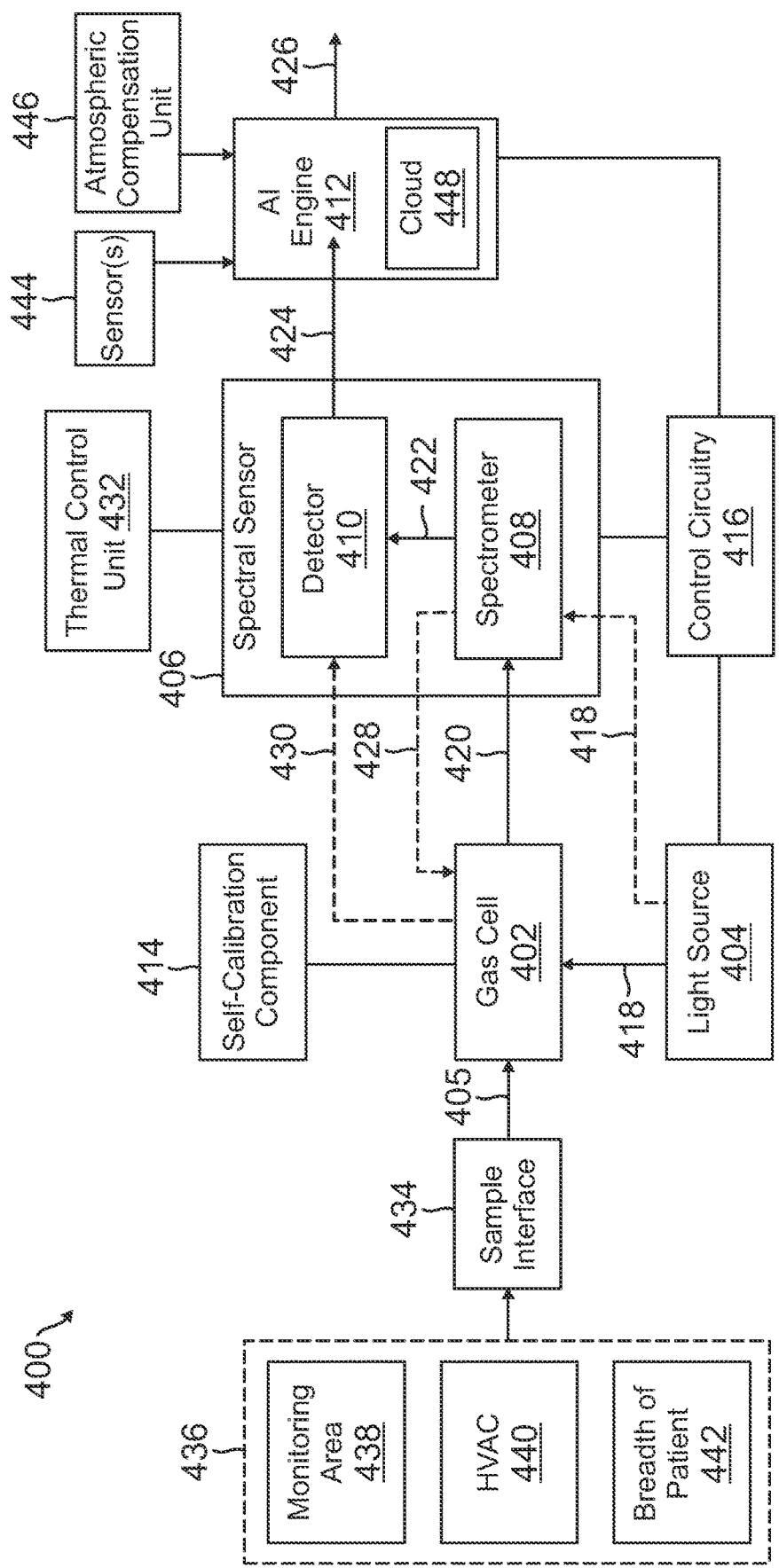
FIG. 4 is a diagram illustrating another example of a gas analyzer according to some aspects.

FIG. 4 is a diagram illustrating another example of a gas analyzer 400 according to some aspects. The gas analyzer 400 shown in FIG. 4 includes a gas cell 402, a light source 404, a spectral sensor 406, an artificial intelligence (AI) engine 412, a self-calibration component 414, and control circuitry 416. As in the example shown in FIG. 3, the light source(s) 404 can be configured to generate incident light 418. In some examples, as shown in FIG. 4, the incident light 418 from the light source 404 may be directed into the gas cell 402 (e.g., via one or more optical coupling elements, not shown) as input light, which interacts with the sample 405 within the gas cell 402 to produce output light 420. The output light 420 may then be input to the spectrometer 408, which is configured to produce an interference beam 422 based on the output light 420. The interference beam 422 may be received by the detector 410, which may be configured to obtain a spectrum 424 of the sample based on the interference beam 422. The spectrum 424 may be input to the AI engine 412 for analysis and processing. The AI engine 412 is configured to process the spectrum 424 to generate a result 426 indicative of at least one parameter associated with the sample based on the spectrum 424.

In other examples (shown by the dotted lines in FIG. 4), the incident light 418 from the light source 404 may first be input to the spectrometer 408. In this example, an interference beam 428 produced by the spectrometer 408 may be directed to the gas cell 402 as the input light that interacts with the sample via multiple reflections of light within the gas cell 402 to produce output light 430. The output light 430 may then be detected by the detector 410 to obtain the spectrum 424 of the sample.

In the example shown in FIG. 4, the gas analyzer 400 may further include a thermal control unit 432 configured to stabilize a temperature at the detector 410. For example, the thermal control unit 432 may include a thermoelectric cooler (TEC), such as a Peltier element, heat sink(s), and/or fans. In addition, the gas analyzer 400 may further include a sample interface 434 configured to input the sample 405 into the gas cell 402. For example, the sample interface 434 may provide an input to the gas cell 402 from a sampling environment 436. Examples of sampling environments 436 include, but are not limited to, a monitoring area 438, an HVAC system 440, or a patient's breath 442 (e.g., exhaled air from a subject under test). In examples in which the sampling environment 436 corresponds to the breath of a patient 443, the sample interface 434 may include, for example, disposable breath sampler (e.g., a mouthpiece or tube). In examples in which the sampling environment 436 corresponds to a monitoring area 436, the gas analyzer 400 can be integrated, via the sample interface 434, into vehicles, buildings, rooms, factories, storage areas, or any other indoor environment, or can be mounted, via the sample interface 434, in an outdoor environment, such as oil and gas sites (e.g., for leakage monitoring and localization), leachate sites, and uncovered water sites.

As in FIG. 3, the control circuitry 416 is also configured to control the light source 404, spectral sensor 406, AI engine 412, and self-calibration component 414. For example, the control circuitry 416, such as a microprocessor, can control the operation of the different components of the gas analyzer 400 and synchronize the operation of the light source 404, the spectral sensor 406, the thermal control unit 432, and the self-calibration component 414. In some examples, the gas analyzer 400 can be operating in different measurement modes. For example, the control circuitry 416 can switch on different components based on user input or to make a measurement at specified frequent discrete measurements. In case of continuous monitoring, the control circuitry 416 may continuously operate the gas analyzer components within specified active hours, collecting spectra continuously with a specified scan time/integration time. The control circuitry 416 can further continuously switch on/off various gas analyzer components, taking a measurement each specified period of time with a certain duty cycle to reduce the self-heating of the system or to improve the lifetime of the components, such that some components are switched off during the processing and the communication time.

In addition, the gas analyzer 400 may further include one or more sensors 444 (e.g., physical or chemical or both types of sensors) that may also optionally be controlled by the control circuitry 416. Each of the one or more sensors 444 may be configured to generate sensor data related to the sample and to provide the sample data to the AI engine 412. In some examples, the one or more other sensors 444 may include, for example, temperature, pressure, and/or flow sensors at the input and/or output of the gas cell 402 to record the flow of the air, temperature, and/or the pressure inside the gas cell 402. Temperature, pressure and/or air flow sensors 444 can be used to enhance the accuracy of the prediction outputs of the AI engine 412. For example, the temperature and pressure affects the molecular vibration spectrum of the gases, and the temperature may have a significant effect on hydrogen bonds, for example. The flow rate and pressure can also affect the equivalent concentration of the air constitutes in the gas cell 402. In examples in which the gas analyzer is utilized in an HVAC system (HVAC environment 440), flow rate sensor data may indicate the flow rate of the HVAC system (e.g., since HVAC systems can typically be operated at different flow rates). Other types of physical sensors 444 can be used for particulate matter, since such particulate matter affects light scattering that can lead to a baseline shift in the spectrometer 408 output.

Chemical sensors 444 for some types of gases can also be integrated with the gas analyzer 400. For example, some gases, such as $O_2$, $H_2$ and $N_2$, have almost no absorption in the infrared region of the spectrum since their vibrations are not accompanied with a change in the diploe moment. Therefore, detection of these types of gases can be performed using their electronic transition spectrum that is usually in the UV-V range. In this example, a UV-V spectral sensor 444 can be integrated in the gas analyzer 400. Other types of gas sensors, such as electrochemical or another suitable type of gas sensor can also be used.

The gas analyzer device 400 further includes an atmospheric compensation unit 446 configured to reduce an effect of the presence of one or more undesired substances in the gas cell 402. In some examples, the atmospheric compensation unit 446 may be controlled by the control circuitry 416 and/or an output of the atmospheric compensation unit 446 may be provided to the AI engine 412. In some examples, the undesired substances include $CO_2$ and/or water vapor ($H_2O$). Since the air contains a percentage of $CO_2$ and water vapor that are not negligible, especially for exhaled air from breath, and since both $CO_2$ and water vapor have strong infrared absorption signals, they may affect the prediction accuracy for other analytes in the air. Therefore, in some examples, the atmospheric compensation unit 446 includes additional sensors that may be used to quantify their presence, and the sensor output together with the spectrometer output may be fed into the AI engine 412 for improving the prediction accuracy of other analytes. For example, a humidity sensor can be used to correct for water vapor presence. In other examples, the atmospheric compensation unit 446 may be included within the AI engine 412 and/or the spectrometer 408 (e.g., the spectral sensor 406).

In some examples, the AI engine 412 may be implemented as or include a cloud-based AI engine 448. In this example, data from the gas analyzer 400 (e.g., spectral data and sensor data) may be transmitted via a wireless or wireline connection to a cloud-based AI engine 446. The cloud-based AI engine 446 may collect data from multiple gas analyzers to produce the result 426. For example, a network of gas analyzers together with a modeling block in the cloud-based AI engine 446 may be used to provide mapping of gas concentrations, based on numerical modeling of gas dispersion and the assimilation of the collected measured data. In an example, for outdoor air monitoring, the gas analyzer 400 can be mounted in an outdoor environment, and data about the air quality can be continuously collected and communicated to the cloud-based AI engine 446 for air quality analysis. In another example, gas analyzers 400 can be mounted on vehicles and the data collected by the gas analyzers (and other sensors) may be wirelessly communicated to the cloud-based AI engine 446 to draw maps of pollution in cities based on the vehicle's mobility.

The gas analyzer 400 is able to predict both chemical and physical parameters. For example, carbon dioxide, water vapor, total volatile organic compounds (TVOCs) are chemical parameters, while the particulate matter is a physical parameter. Part of the collected data may be used for training the AI engine 412 using, for example, reference values from a reference device.

FIGS. 5A-5C are diagrams illustrating another example of a gas analyzer 500 according to some aspects. The gas analyzer 500 includes a gas cell 502, a spectral sensor 504, a light source 506, control circuitry 508, and optical coupling elements 510 (e.g., reflectors, such as mirrors). The gas cell 502 is a Herriot gas cell including two reflectors (e.g., two mirrors) 512 and 514. In the example shown in FIG. 5A, light from the light source 506 is optically coupled into the gas cell 502 using an input optical coupling element 510. The light source 506 may be in the form of coherent light source, such as supercontinuum source or frequency comb, or in the form of uncoherent light source, such as thermal radiator or light emitting diode, plasma, or other suitable light source. The light interacts with the gas (air) under test within the gas cell 502 based on multiple reflections of the light therein, and the resulting output light is directed into the spectral sensor 504 via, for example, an output optical coupling element 510. The spectral sensor 504 includes, for example, a spectrometer configured to produce an interference beam based on the output light. The interference beam is then optically coupled to a detector (e.g., photodetector) within the spectral sensor for the detection of light (e.g., detection of the interference beam) and energy conversion into an electrical form to produce a spectrum. The control module (e.g., a mother board) is used to power the light source 506 and power the spectral sensor 504. In some examples, the optical coupling elements 510 may be optical lenses or reflectors.

As shown in FIG. 5B, gas (e.g., air) may be input to the gas cell 502 via a gas inlet 516 and exit the gas cell 502 via a gas outlet 518. In some examples, as further shown in FIG. 5C, the gas inlet and gas outlet may be coupled to a tube 520 (e.g., a sample interface) configured to provide the flow of gas into and out of the gas cell 502. In addition, a valve 522 may be used to control the flow of the air/gas from an input 524 to an output 526.

Figures 6A, 6B, 6C:
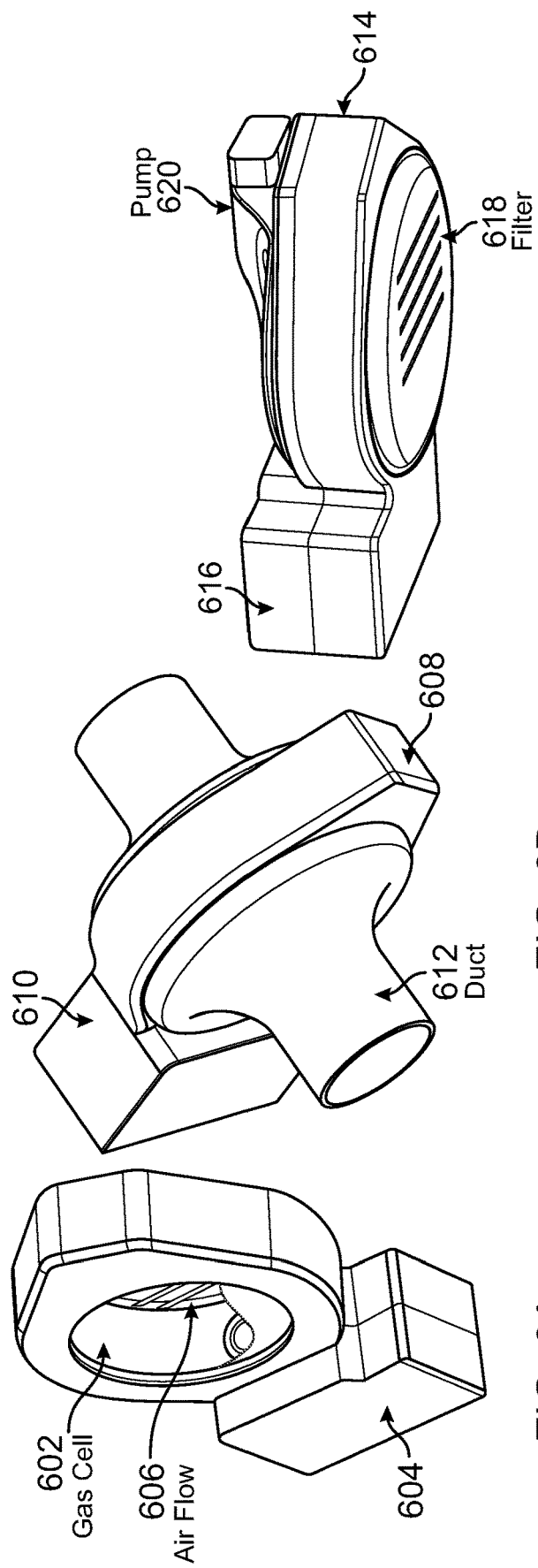
FIGS. 6A-6C are diagrams illustrating examples of gas analyzer configurations according to some aspects.

FIGS. 6A-6C are diagrams illustrating examples of gas analyzer configurations according to some aspects. In the example shown in FIG. 6A, the gas analyzer main blocks include the gas cell 602 for light/air interaction and the spectroscopic unit (e.g., at least the light source and spectral sensor) 604 for analyzing the light. In some examples, the gas cell 602 may be considered to be a part of the spectroscopic unit 604. The gas analyzer can be mounted such that the natural air flow leads 606 force the air to enter and exit the gas cell 602.

In another example, as shown in FIG. 6B, the gas analyzer can be configured in an inline operation. For example, the gas analyzer can be inserted in air ducts 612 for ducted operation, such that the air flowing through the duct 612 enters the gas cell 608 for light/air interaction and the resulting output light may be measured by the spectroscopic unit 610. In a further example, as shown in FIG. 6C, the gas analyzer can be equipped with a pump 620 for generating the air flow and controlling the pressure of the air in the gas cell 614. Filters (e.g., filter 618) can be used as well to prevent dust particles or humidity condensation accumulating in the gas cell 614 or spectroscopic unit 616. In this example, the gas analyzer can be mounted under a seat, above a roof, or localized in a corner. In each of the configurations shown in FIGS. 6A-6C, the gas analyzer can be equipped with wireless communication capabilities for data transfer and/or powering.

Figure 7:
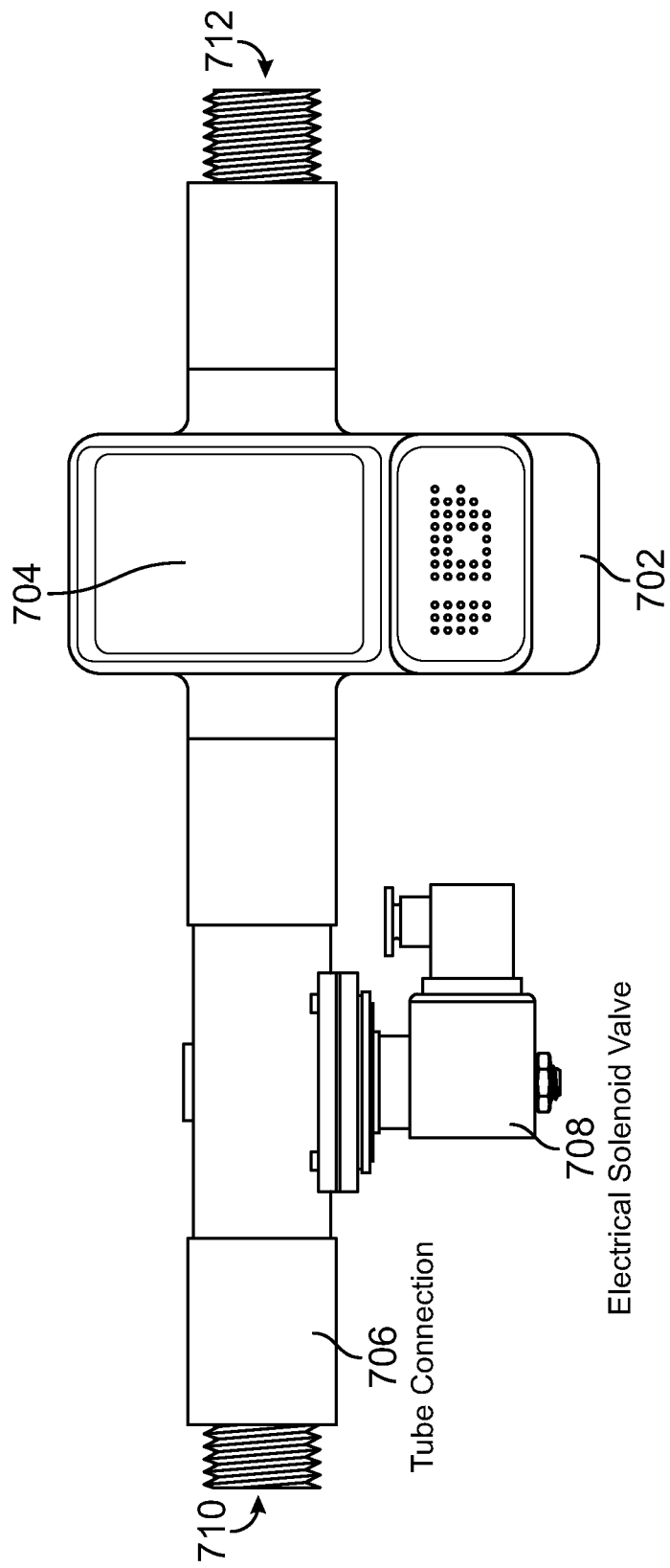
FIG. 7 is a diagram illustrating another gas analyzer configuration according to some aspects.

FIG. 7 is a diagram illustrating another gas analyzer configuration according to some aspects. For ducted operation, as shown in FIG. 7, a tube connection 706 (e.g., sample interface) is used to interface the spectroscopic unit 702 and gas cell 704 within the spectroscopic unit 702 with the indoor/outdoor environment. One or more valves 708 may be used to control the flow of the air/gas from an input 710 to an output 712. Other sensors, such as flow meters and pressure meters, can be used as well at the input 710 and/or output 712 to record the flow of the air and the pressure inside the gas cell. In some examples, the gas analyzer can be mounted in close proximity to oil and gas sites or gas pipes for leakage monitoring and localization.

Figure 8:
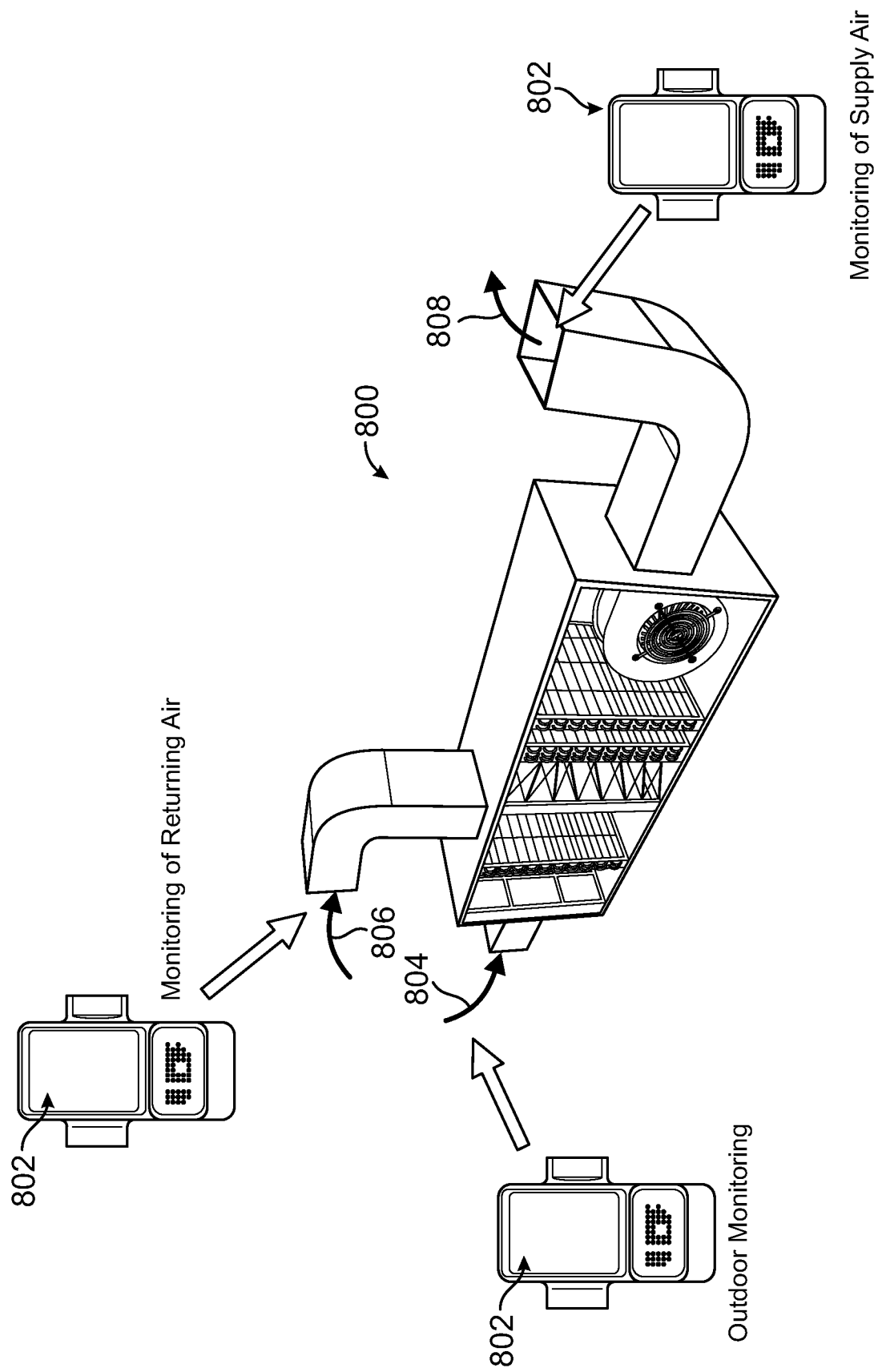
FIG. 8 is a diagram illustrating another gas analyzer configuration according to some aspects.

FIG. 8 is a diagram illustrating another gas analyzer configuration according to some aspects. In the example shown in FIG. 8, a gas analyzer 802 can be mounted in one or more locations in an HVAC system 800. For example, the gas analyzer 802 can be mounted on an output 808 of the HVAC system 800 to monitor the supplied air from the HVAC system 800. As another example, the gas analyzer 802 can also be mounted on a return air input 806 to the HVAC system 800 for monitoring the quality of the returned air. In both of the above examples, the indoor air quality is monitored. In a further example, the gas analyzer 802 can be mounted on an outdoor air input port 804 of the HVAC system 800 to monitor the quality of the outdoor air input to the system.

Figure 9B:
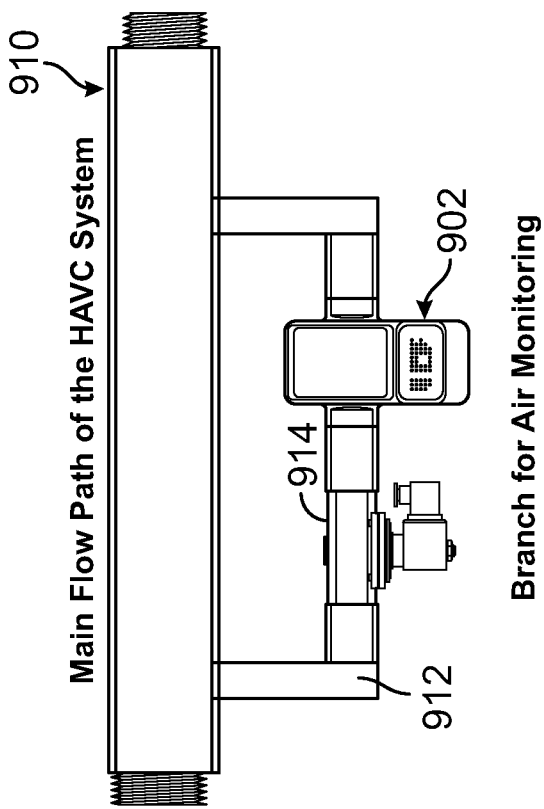
FIGS. 9A and 9B are diagrams illustrating another gas analyzer configuration according to some aspects.
Figure 9A:
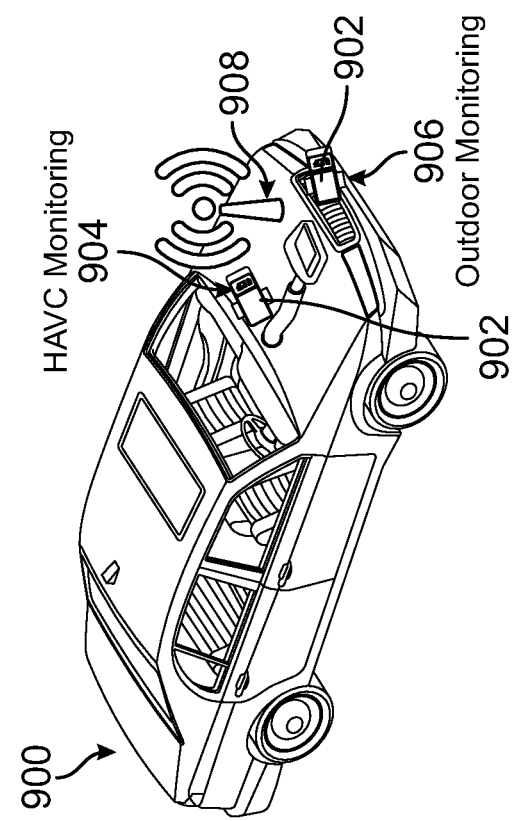

FIGS. 9A and 9B are diagrams illustrating another gas analyzer configuration according to some aspects. In the example shown in FIG. 9A, the gas analyzer 902 can be mounted in a vehicle 900 for monitoring the air inside the car (e.g., within an HVAC system 904) or monitoring outdoor air in the environment 906. In addition, the gas analyzer may be mounted under the seat or in the top of the car (not shown) to monitor the air quality inside the car (e.g., within the cabin). In examples in which the gas analyzer 902 is mounted in the HVAC system 904 of the car 900, as shown in FIG. 9B, the gas analyzer 902 can be mounted in a main path 910 in which the air is flowing or within a branch 912 of the main path 910 created for air monitoring that does not affect the main path. For outdoor air monitoring 906, the gas analyzer 902 can be mounted behind the grill in the front of the car 900 or in any other place. With outdoor air monitoring 906, data related to the air quality can be continuously collected while the vehicle 900 is moving. The vehicle 900 may further include a wireless device 908 or the gas analyzer 902 may be configured with a wireless transceiver to communicate the collected spectral data and any other related sensor data to a cloud-based AI engine for analysis.

Figure 10:
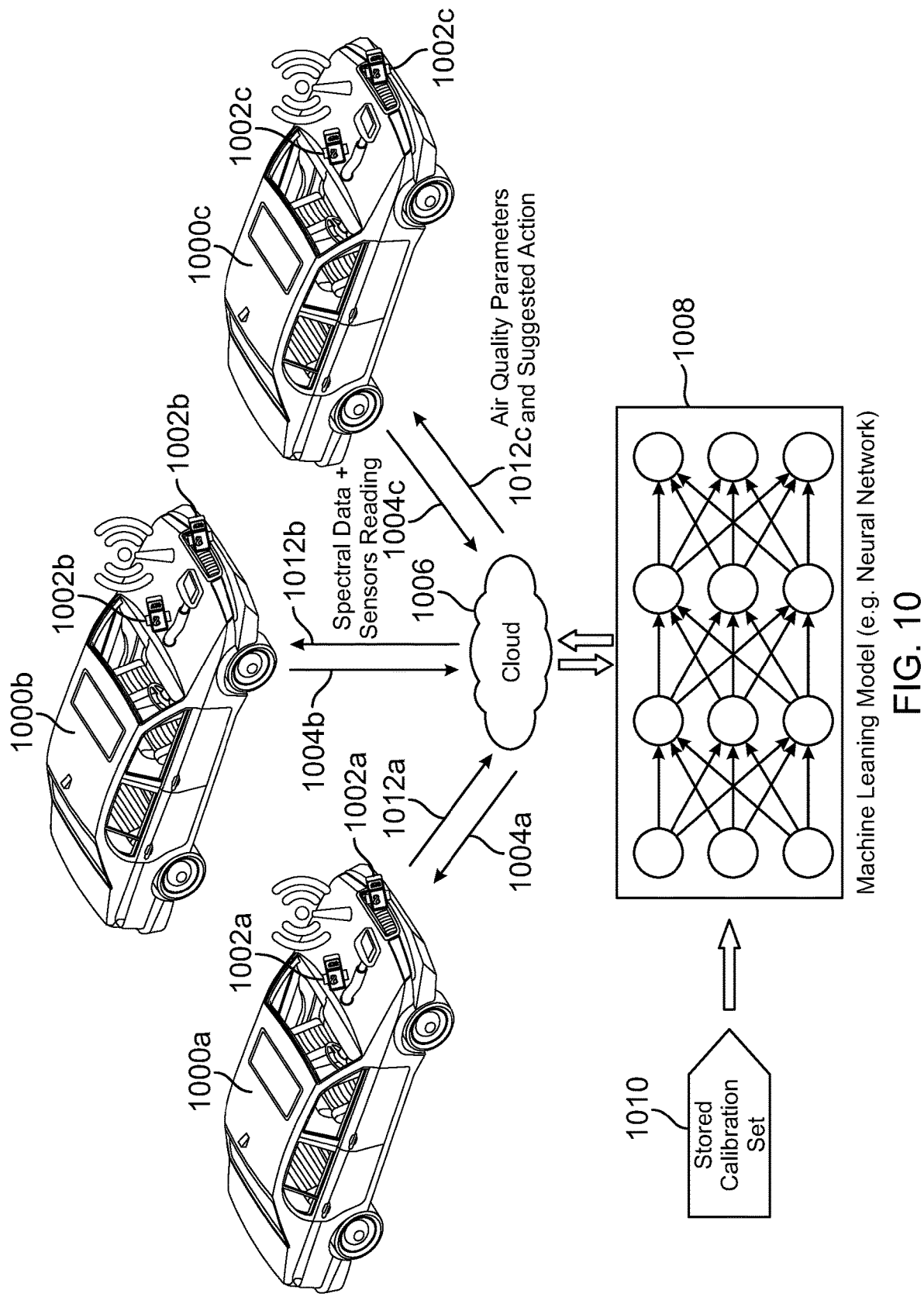
FIG. 10 is a diagram illustrating an example of a cloud-based configuration of gas analyzers according to some aspects.

FIG. 10 is a diagram illustrating an example of a cloud-based configuration of gas analyzers according to some aspects. In the example shown in FIG. 10, a wireless communication network including a plurality of gas analyzers 1002a-1002c distributed over an area is realized. The gas analyzers 1002a-1002c may be mounted, for example, within vehicles 1000a-1000c moving within the area. A gateway 1006 may be used to collect data 1004a-1004c sent by the gas analyzers 1002a-1002c deployed over the area and to redirect the collected data 1004a-1004c to a cloud-based AI engine 1008. In some examples, the data 1004a-1004c may include spectral data obtained by the spectroscopic unit (e.g., light source, gas cell, and spectral sensor) of the gas analyzer. In addition, the data 1004a-1004c may further include sensor data (e.g., sensor readings, such as air flow, pressure, temperature, etc.) obtained by one or more sensors of the gas analyzer. The AI engine 1008 can implement a machine learning (ML) model (e.g., a neural network) to process the received data 1004a-1004c using a calibration model that may be stored, for example, on a database 1010. For example, the database 1010 may store sets of calibration models (e.g., statistical regression models) and the AI engine 1008 may select one of the calibration models for processing the data 1004a-1004c. The AI engine 1008 may then transmit a result 1012a-1012c to the vehicles 1000a-1000c and/or the gas analyzers 1002a-1002c produced based on the data 1004a-1004c. For example, the result 1012a-1012c may include air quality parameters and/or a recommended action.

In some examples, the network of gas analyzers 1002a-1002c, together with the cloud-based AI engine 1008, may be configured to provide a mapping of gas concentrations, based on numerical modeling of gas dispersion and the assimilation of the collected measured data 1004a-1004c. Different forms of mapping can be produced depending on the use case. For example, inverse modeling can serve for localization of gas leakages, if any. As another example, the cloud-based AI engine 1008 may use the collected data 1004a-1004c to draw maps of pollution in cities based on the vehicles 1000a-1000c mobility. Data from additional sensors determining the air flow speed and directions can be used to predict the dispersion of the pollution.

In some examples, the AI engine may be localized in each of the gas analyzers 1002a-1002c, and the data 1004a-1004c and/or the result 1012a-1012c may be transmitted to a database (not shown) for their storage. For example, a database may be set up on a server. This database can centralize all information needed for further processing of the collected data. In addition to the spectral and sensor data, other data, such as the location of sensors, the dates of receipt of the measurement, etc., may be stored in the database. In some examples, a library allows access to the data without having to know the structure of the database may be provided.

Figure 11:
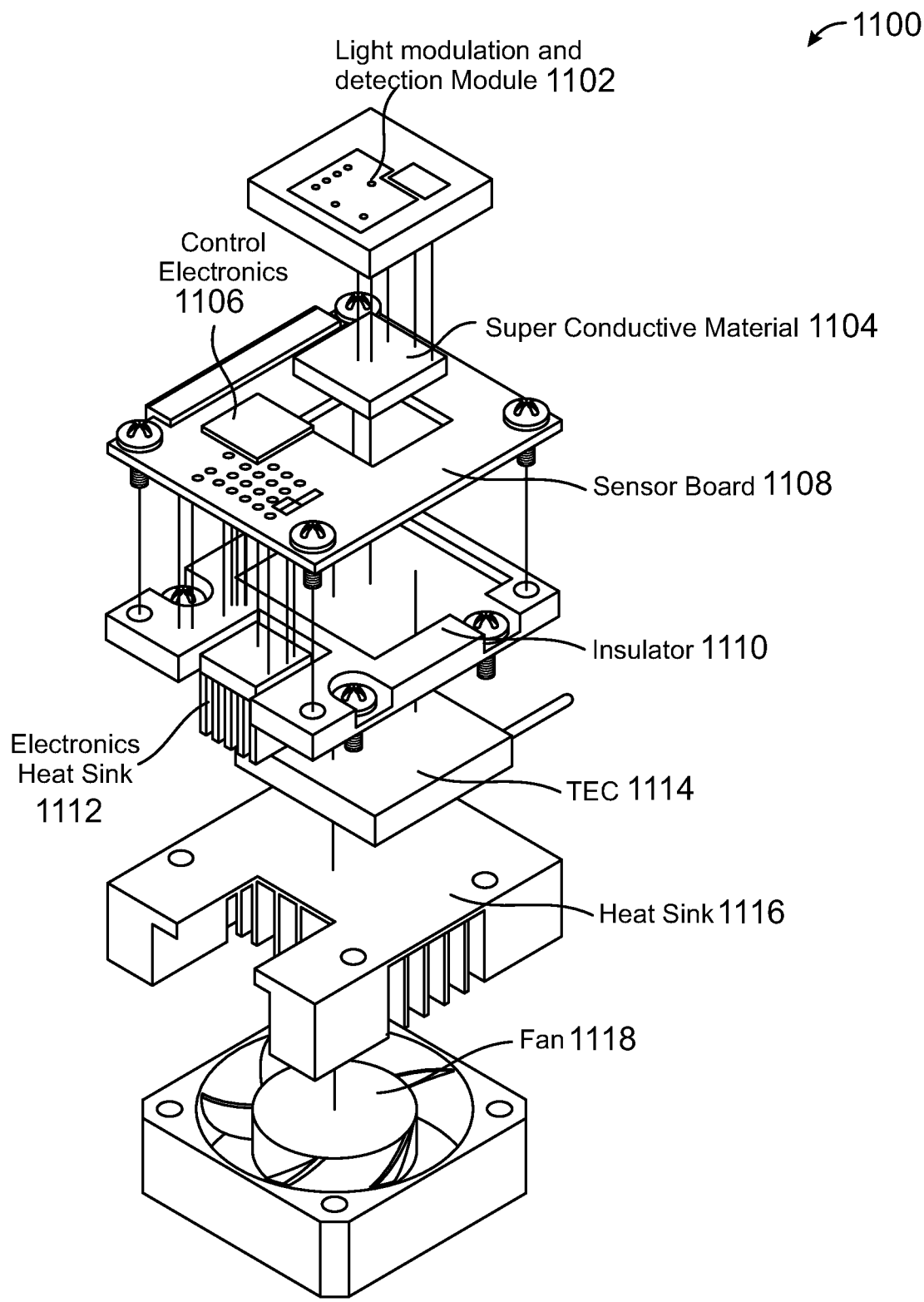
FIG. 11 is a diagram illustrating a gas analyzer including a thermal control unit according to some aspects.

FIG. 11 is a diagram illustrating a gas analyzer 1100 including a thermal control unit according to some aspects. The thermal control unit is configured to stabilize the gas analyzer 1100 by cooling the components that are thermally sensitive, such as a detector. In some examples, the thermal control unit can include a Thermoelectric Cooler (TEC) 1114 for stabilizing the temperature at the detector (e.g., photodetector) of the spectral sensor 1102 (e.g., Light Modulation and Detection Module (LMDM)). The TEC 1114 can be mounted below a sensor board 1108 to control the temperature of the LMDM 1102. For efficient operation, the conduction resistance should be very low between the TEC 1114 and the LMDM 1102. For example, a hole can be drilled in the sensor board 1108 below the LMDM 1102. Moreover, a super conductive material 1104 with a thermal interface material can be included to enhance the conduction between the LMDM 1102 and the TEC 1114. The thermal conduction can also be enhanced by adding thermal vias or by embedding copper coin in the sensor board 1108 (e.g., printed circuit board (PCB)).

From the other side of the TEC 1114, a heat sink 1116 and a cooling fan 1118 can be included in the gas analyzer 1100 in order to dissipate the heat generated from the TEC 1114. An electronics heat sink 1112 may further be included to dissipate heat from control electronics 1106 on the PCB 1108. Insulator material 1110 between the heat sink 1116 and the PCB 1108 can also be added to prevent the heat from returning back to the PCB 1108.

In some examples, the TEC 1114 can be implemented in an open loop configuration with no feedback of temperature to the driving circuitry; however, this may not be suitable for variations in ambient temperature and changes in the self-heating conditions of the gas analyzer 1100. Therefore, a closed-loop control loop may be used to ensure high accurate stabilization of the temperature of the LMDM 1102, including a temperature sensor and a control chip (e.g., control electronics) 1106. The control chip 1106 can include, for example, a proportional-integral-derivative (PID) controller, a difference amplifier, a compensation amplifier/network and an H-bridge. The difference amplifier can compare the current temperature sensor voltage with a target set-point temperature voltage resulting in an error voltage. The compensation amplifier/network can amplify the error signal, compensate and stabilize the feedback loop, and drive the next power/output stage. The H-bridge can control the magnitude and direction of TEC current to control whether it should cool or heat the gas analyzer 1100. In some examples, the temperature sensor can be a thermistor beside or inside the LMDM 1102, or a temperature sensor inside the control electronics 1106 next to the LMDM 1102 on the PCB 1108. The temperature drift can also be extracted from the LMDM 1102 itself or specifically from the photodetector through spectral features drift.

FIGS. 12A-12D are diagrams illustrating example configurations of a thermal control unit of a gas analyzer according to some aspects. In the examples shown in FIGS. 12A and 12B, the thermal control unit can include a Peltier element (e.g., TEC) 1206 directly attached to the backside of a sensor board (e.g., PCB) 1204, relying on the thermal conductivity of the board internal layers. A spectral sensor (e.g., light modulation chip of LMDM) 1202 may thus be attached to the topside of the PCB 1204. A heat sink 1208 and fan 1210 may further be included under the TEC 1206 in order to dissipate the heat generated from the TEC 1206. A thermistor 1212 adjacent the light modulation chip 1202 may provide a temperature of the light modulation chip 1202 to a control chip 1214 (e.g., control circuitry) via an electrical connection 1216 therebetween for closed-loop control of the TEC 1206. In the example shown in FIG. 12B, thermal conductivity between the light modulation chip 1202 and the TEC 1206 can be improved having a backside exposed pad 1220 soldered onto a sensor pad on the sensor board 1204 in addition to having thermal conduction vias 1218 in the sensor board 1204.

Figure 12A:
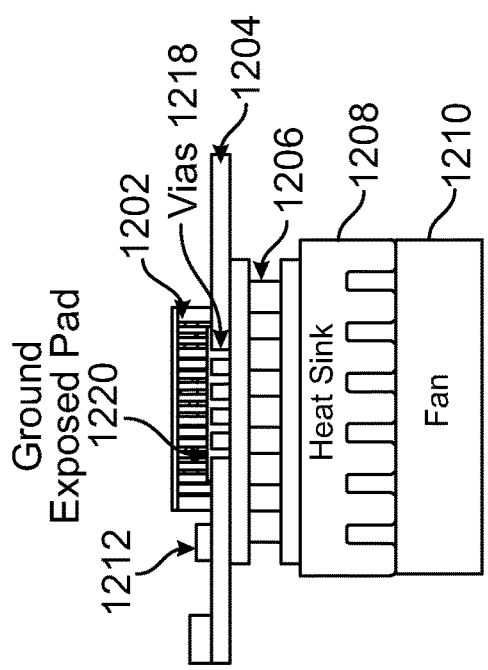
FIGS. 12A-12D are diagrams illustrating example configurations of a thermal control unit of a gas analyzer according to some aspects.
Figure 12B:
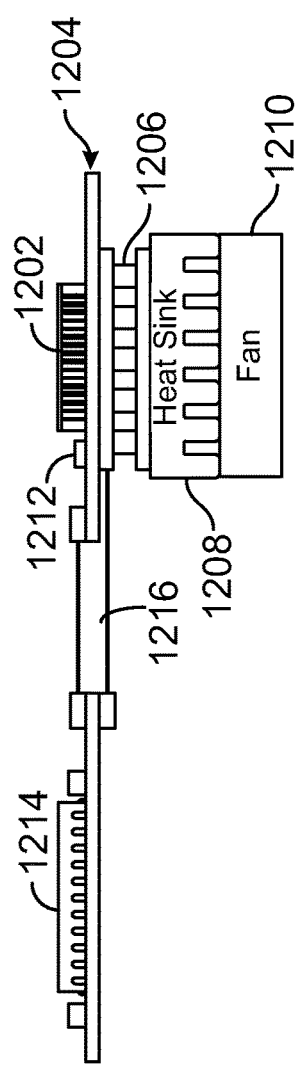
Figure 12C:
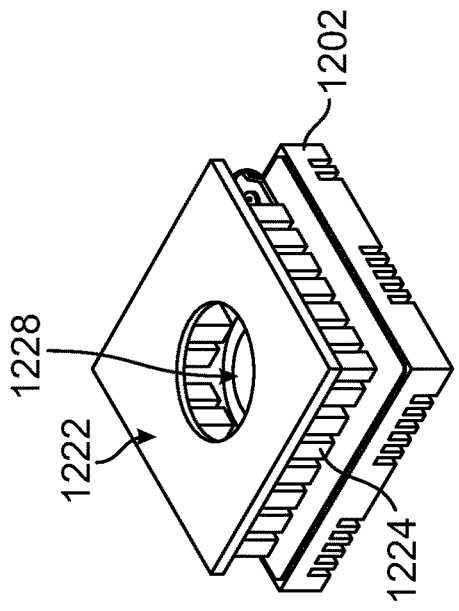
Figure 12D:
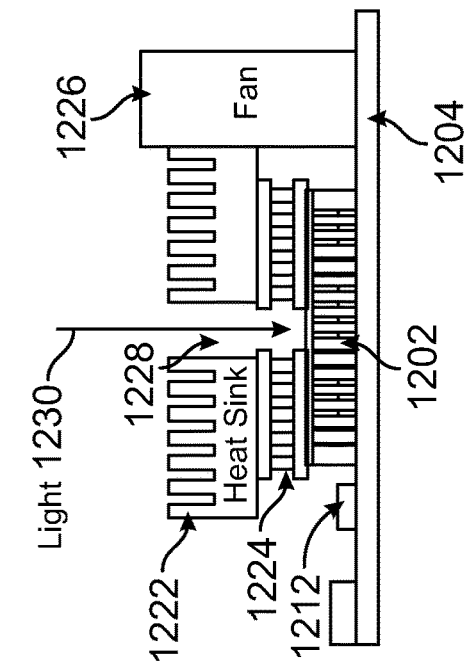

In the example shown in FIGS. 12C and 12D, a Peltier element (e.g., TEC) 1224 with a hole 1228 can be attached to the topside of the light modulation chip 1202, such that light 1230 is coupled to the light modulation chip 1202 through the hole. A heat sink 1222 with a hole (e.g., hole 1228 through the heat sink 1222 and Peltier element 1224) can be attached as well to the topside of the Peltier element 1224. In addition, a fan 1226 can be included on the topside of the sensor board 1204 (e.g., PCB) to cool the heat sink 1222 and Peltier element 1224. The thermistor 1212 may further be included on the topside of the PCB 1204 adjacent to the light modulation chip 1202 to measure the temperature of the light modulation chip 1202.

As discussed above, since the air contains a percentage of $CO_2$ and water vapor and both $CO_2$ and water vapor have strong infrared absorption signals, these undesired substances may affect the prediction accuracy for other analytes in the air. For example, gas absorption inside the gas cell can affect the interferogram bursts shape and position. However, the impact of the sample on the spectral sensor interferogram can be compensated, especially the sharp bands of $CO_2$ and water vapor, as described below. In some examples, the gas analyzer further includes an atmospheric compensation unit (e.g., atmospheric compensation unit 446 shown in FIG. 4) configured to reduce an effect of the presence of one or more undesired substances in the gas cell. In some examples, as discussed above, the atmospheric compensation unit may include one or more additional sensors to quantify the presence of the undesired substances and the output data from the one or more additional sensors, along with the spectral sensor output, may be fed to the AI engine for improving the prediction accuracy of other analytes. For example, humidity sensor can be used to correct for water vapor presence.

In other examples, the atmospheric compensation unit (e.g., atmospheric compensation unit 446 shown in FIG. 4) may include an apodization function in the spectrometer of the spectral sensor (e.g., spectrometer 408 of the spectral sensor 406 shown in FIG. 4) that can be used to reduce the impact of the presence of $CO_2$ and water vapor. The apodization function can be applied on the interferogram produced by the spectrometer. In various aspects, the apodization function applied on the interferogram can be studied for spectra of water vapor and Toluene to show how the water vapor peak and side lobes are affected by the apodization. For example, Gaussian and Boxcar apodization functions can be compared for Toluene spectra with different water vapor levels.

Figure 13A:
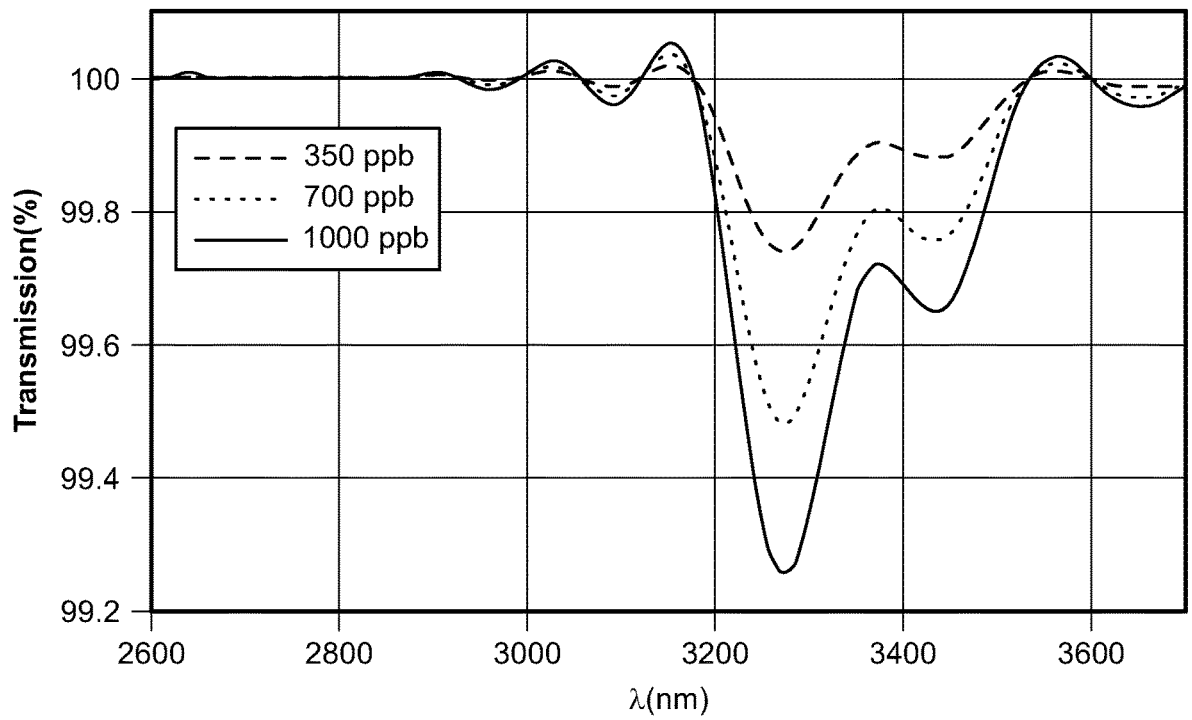
FIGS. 13A and 13B are diagrams illustrating spectra of an analyte (sample) under test using different apodization functions according to some aspects.
Figure 13B:
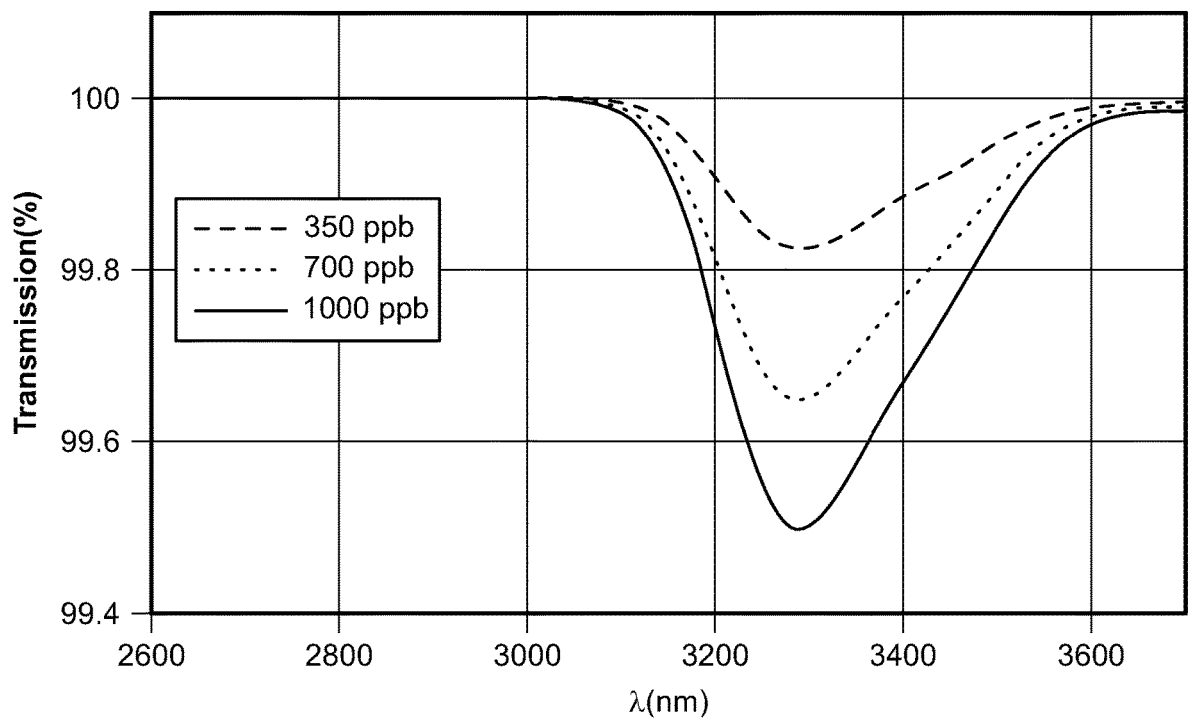

FIGS. 13A and 13B are diagrams illustrating spectra of an analyte (sample) under test using different apodization functions according to some aspects. FIG. 13A illustrates the spectra of pure Toluene with concentrations of 350, 700 and 1000 ppb at a resolution of 80 $cm^{-1}$ and path length of 20 m using the Boxcar apodization, while FIG. 13B illustrates the same spectra using the Gaussian apodization. As can be seen in FIGS. 13A and 13B, the Toluene peak has better resolution when Boxcar apodization is applied, but the sidelobes disappear in the case of Gaussian apodization.

Figure 14A:
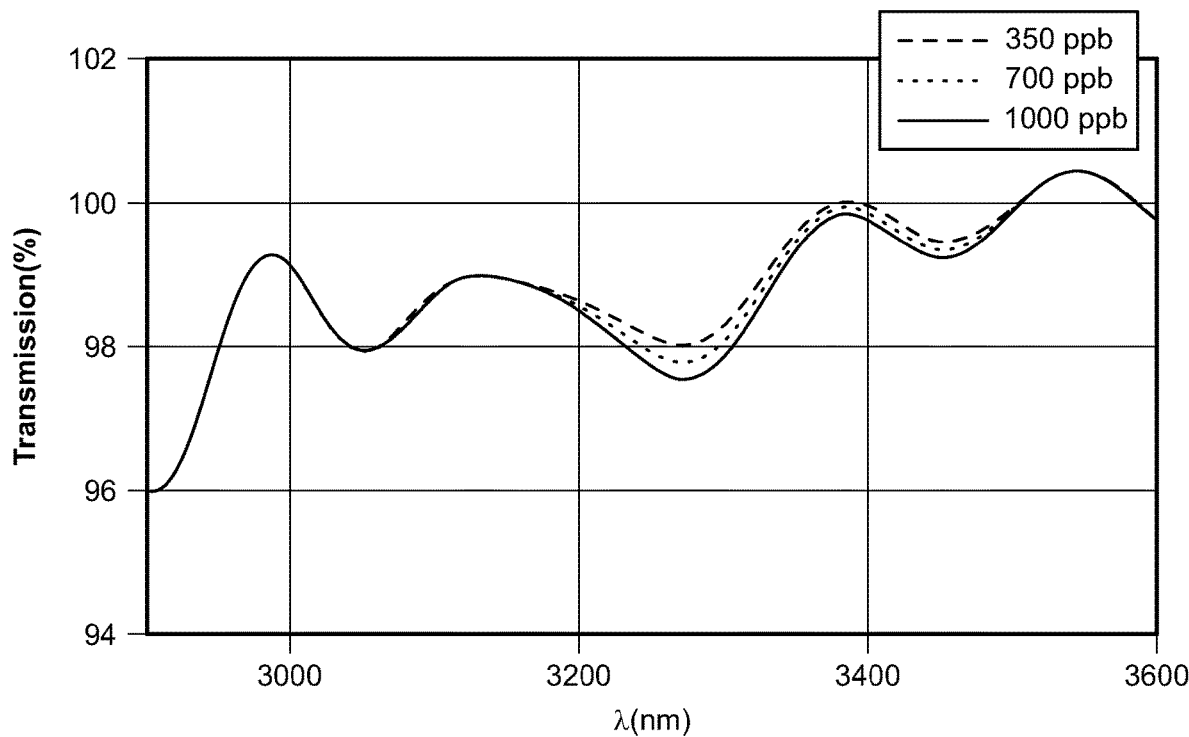
FIGS. 14A and 14B are diagrams illustrating spectra of an analyte with water vapor using different apodization functions according to some aspects.
Figure 14B:
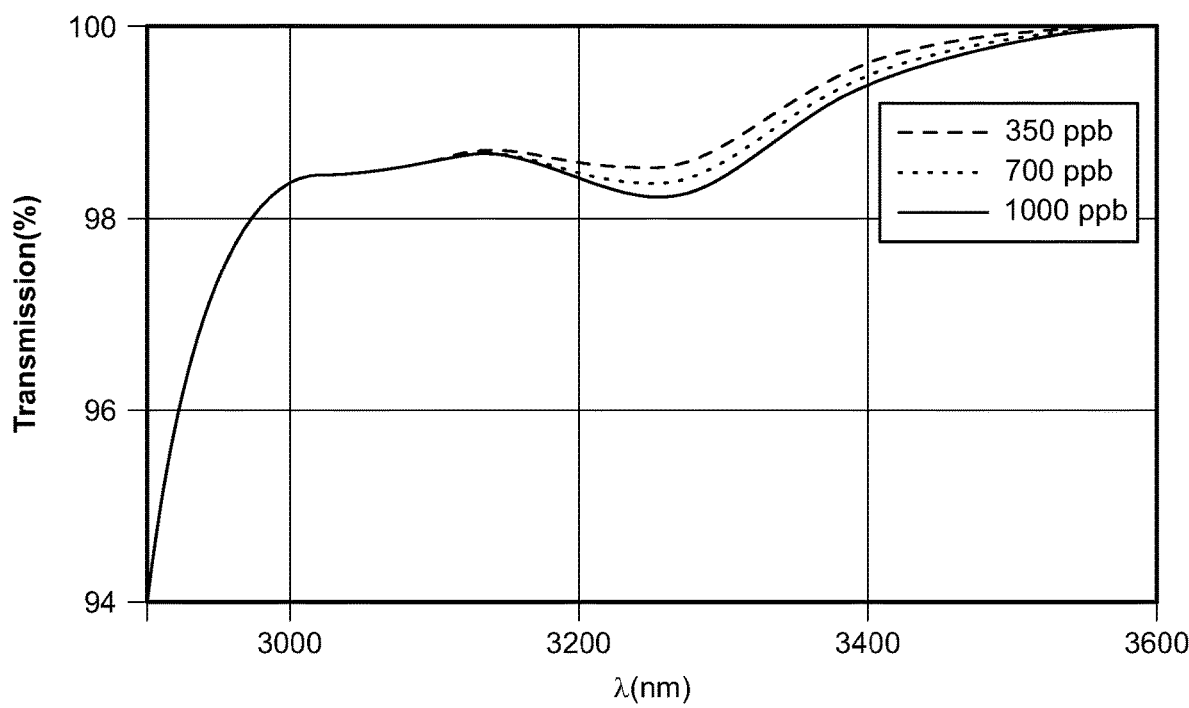

FIGS. 14A and 14B are diagrams illustrating spectra of an analyte with water vapor using different apodization functions according to some aspects. FIG. 14A illustrates the spectra of Toluene with concentrations of 350, 700 and 1000 ppb with a water vapor concentration of 0.14% at a resolution of 80 $cm^{-1}$ and path length of 20 m using the Boxcar apodization, while FIG. 14B illustrates the same spectra using the Gaussian apodization. It should be noted that a water vapor concentration of 0.14% is low compared to the usual water vapor atmospheric level. At the Toluene absorption region, there is water vapor absorption as the baseline is shifted. This shift is due to actual water vapor absorbance and not sidelobes of the water vapor peak because this shift is still clear even when Gaussian apodization is used.

Figure 15A:
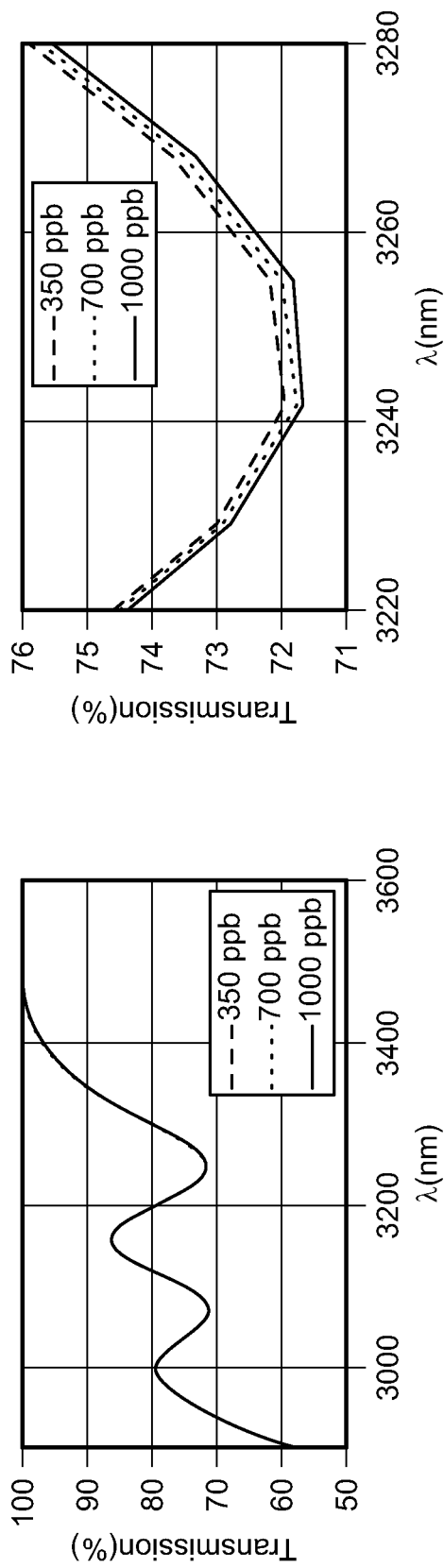
FIGS. 15A and 15B are further diagrams illustrating spectra of an analyte with water vapor using different apodization functions according to some aspects.
Figure 15B:
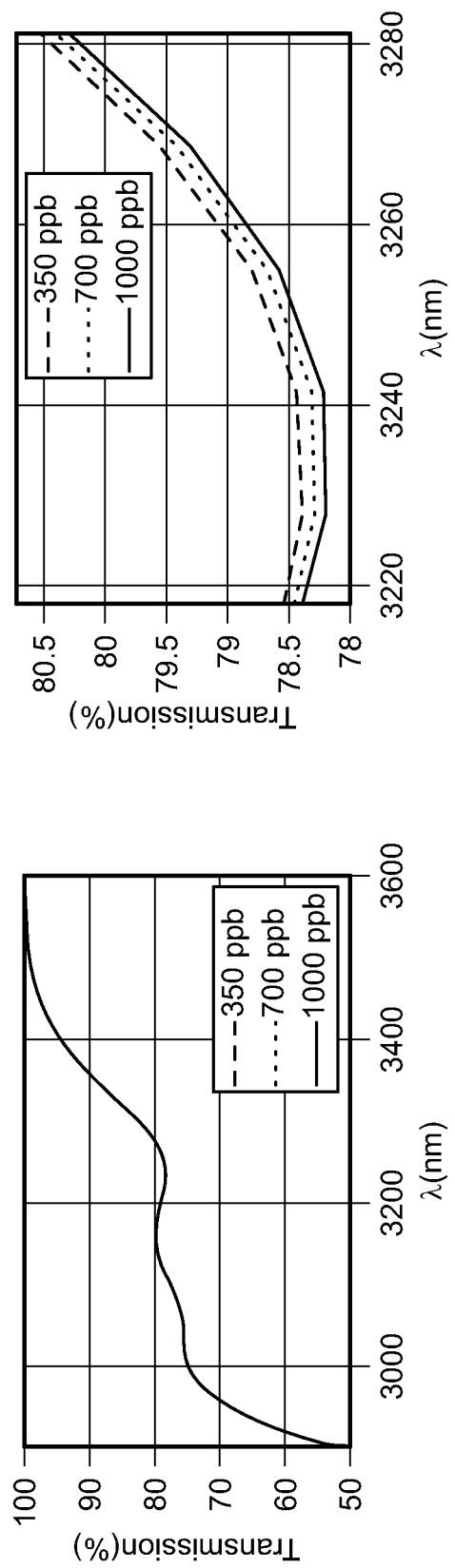

FIGS. 15A and 15B are further diagrams illustrating spectra of an analyte with water vapor using different apodization functions according to some aspects. FIG. 15A illustrates the spectra of Toluene with concentrations of 350, 700 and 1000 ppb with water vapor of concentration 3% at a resolution of 80 $cm^{-1}$ and path length of 20 m using the Boxcar apodization, while FIG. 15B illustrates the same spectra using the Gaussian apodization. It should be noted that a water vapor concentration of 3% is close to the usual atmospheric levels. The weak absorption of Toluene is insignificant compared to the strong water vapor absorption in both apodizations.

Therefore, to be able to measure small concentrations of Toluene at atmospheric conditions, the atmospheric compensation unit (e.g., atmospheric compensation unit 446 shown in FIG. 4) may further include a water vapor compensation technique applied on the measured spectra by the AI engine (e.g., AI engine 412 or cloud-based AI engine 446 shown in FIG. 4) and the spectrometer (e.g., spectrometer 408 shown in FIG. 4). For example, a database of water vapor and/or $CO_2$ absorption spectrum at different temperatures and pressures can be formed either from experimental measurements or theoretically from existing databases, such as Pacific Northwest National Laboratory (PNNL), High-Resolution Transmission Molecular Absorption Database (HITRAN), or other available existing databases. The theoretical/experimental spectra can then be processed by the AI engine using synthesized spectral sensor characteristics, such the spectral resolution, self-apodization, baseline artifacts, thermal drift with temperature, etc., to produce processed spectra. The processed spectra may be provided by the AI engine to the spectrometer for application to the interferogram produced by the spectrometer. One simple example is direct subtraction of the processed spectra from the measured spectra by the spectrometer.

Figure 16A:
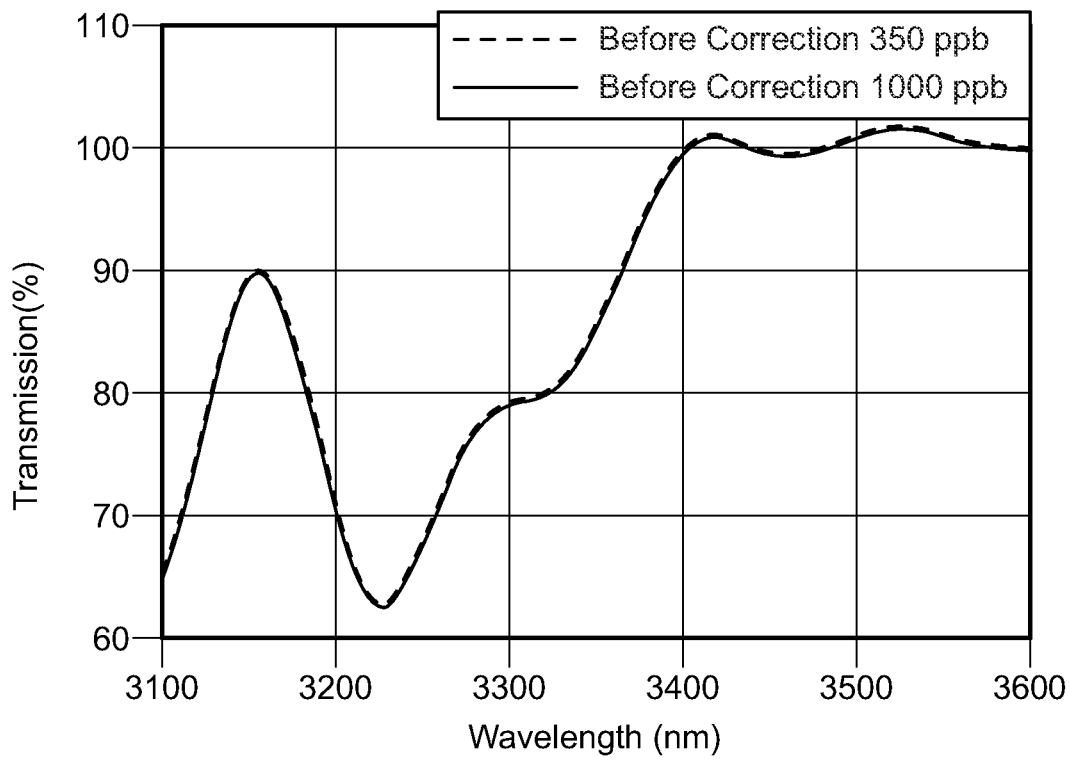
FIGS. 16A and 16B are diagrams illustrating examples of simulated spectra of an analyte with water vapor before and after atmospheric compensation according to some aspects.
Figure 16B:
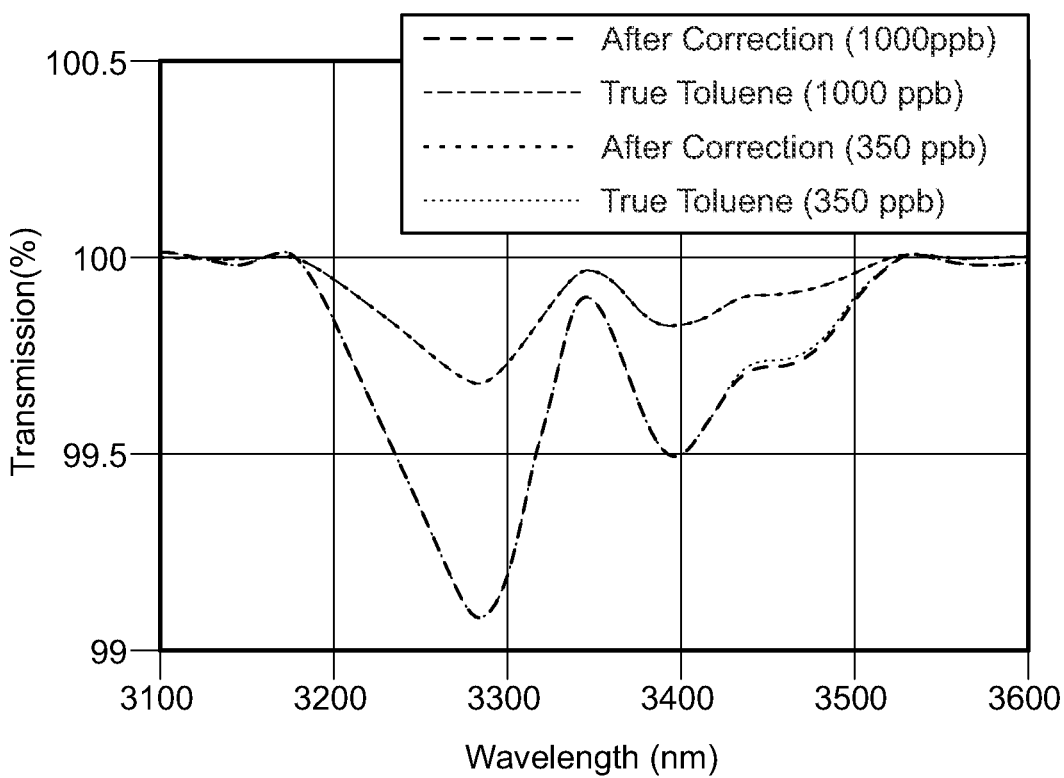

In various aspects, the water vapor compensation technique can first be applied to simulated spectra of Toluene with water vapor to test the performance of this technique to eliminate water vapor absorption. FIGS. 16A and 16B are diagrams illustrating examples of simulated spectra of an analyte with water vapor before and after atmospheric compensation according to some aspects. The simulated spectra used are for 350 and 1000 ppb Toluene with 4% water vapor at a resolution 66 $cm^{-1}$ and pathlength of 20 m. FIG. 16A illustrates the spectra before compensation where the Toluene 350 ppb and Toluene 1000 ppb are not differentiated from each other due to the strong absorption of water vapor compared to the absorption of Toluene. FIG. 16B illustrates the spectra after applying the atmospheric compensation method described above compared with true Toluene (pure 350 and 1000 ppb) spectra. FIG. 16B illustrates the similarity between the spectra after applying the atmospheric compensation method and the spectra of pure Toluene.

Figure 17:
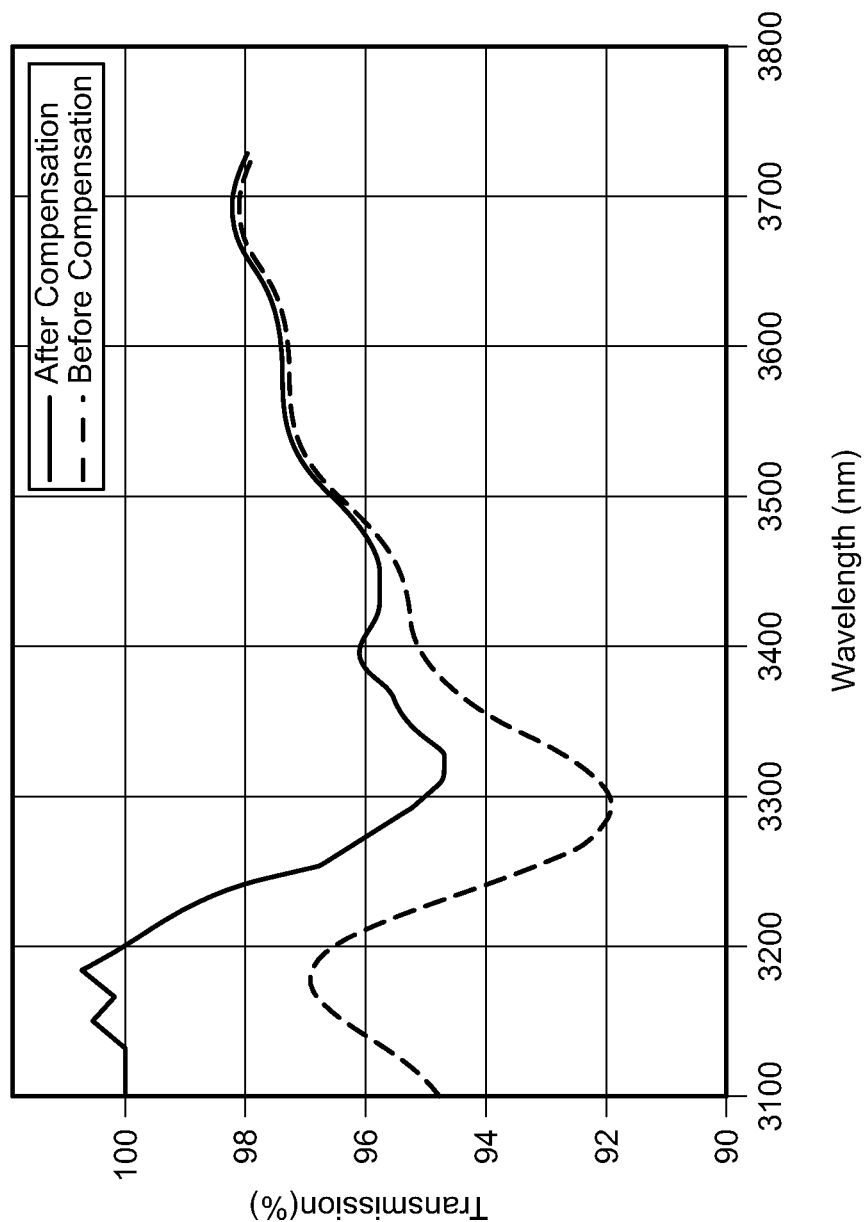
FIG. 17 is a diagram illustrating a spectra of an analyte with water vapor after compensation according to some aspects.

The water vapor compensation method discussed above can then be applied to the measured spectra of Toluene that contains different concentrations of water vapor. FIG. 17 is a diagram illustrating a spectra of an analyte with water vapor after compensation according to some aspects. The water vapor compensation method was applied on Toluene with concentrations of 7, 11 and 55 ppm with a resolution 80 cm$^{-1}$ and a path length of 20 m. FIG. 17 illustrates the spectrum of Toluene 7 ppm before and after applying the compensation technique. As can be seen in FIG. 17, the absorption decreased after the water vapor compensation method because the water absorption was eliminated.

In an example in which the gas analyzer is mounted in a moving vehicle, the gas cell should be mechanically stable to prevent any changes in the optical path length or coupling efficiency of the light as a result of shock and vibration in the moving vehicle. In some examples, the size of the cell may be reduced to be more compact and to minimize the optical tolerance (of angles and decentering).

Figure 18A:
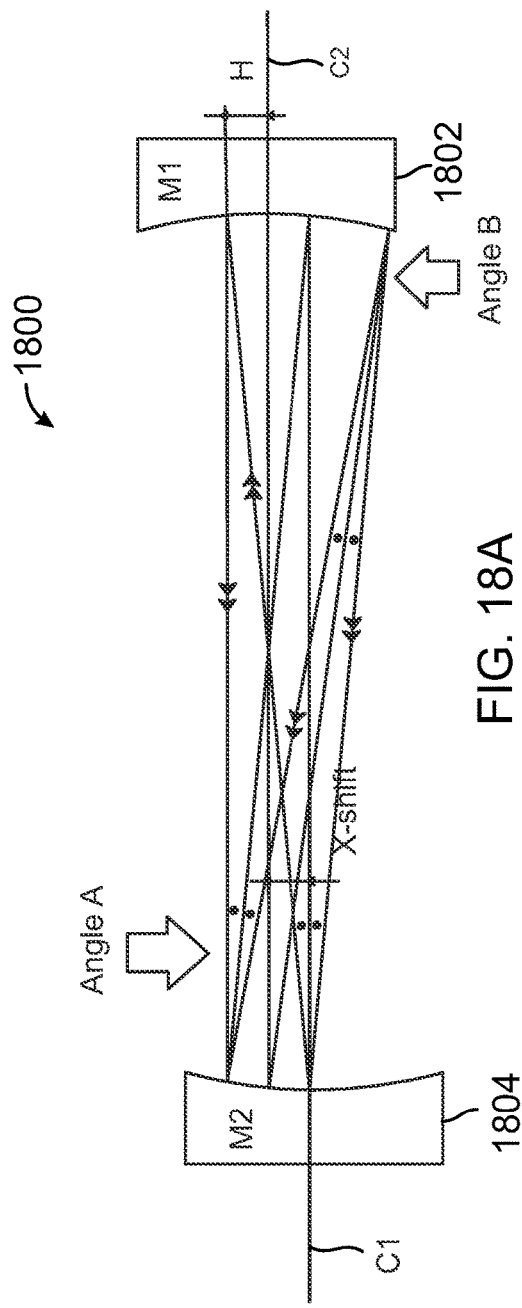
FIGS. 18A and 18B are diagrams illustrating an example of a modified Herriot gas cell according to some aspects.
Figure 18B:
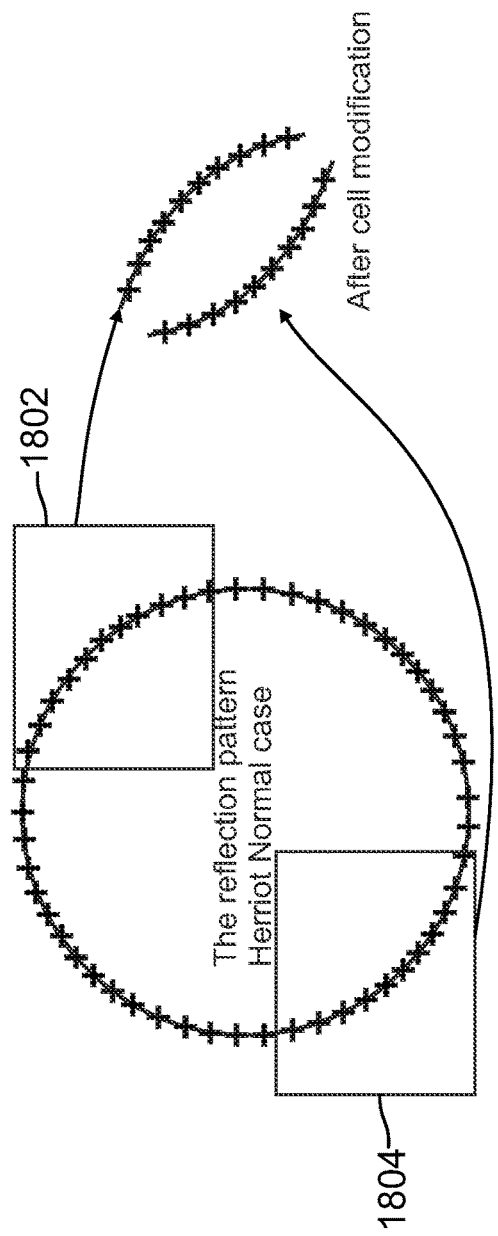

FIGS. 18A and 18B are diagrams illustrating an example of a modified Herriot cell according to some aspects. The modified Herriot cell is an asymmetrical Herriot cell 1800 that is more compact and can tolerate vibrations when mounted in, for example, a moving vehicle. The asymmetrical Herriot cell 1800 includes a first reflector 1802 (e.g., mirror M1) and a second reflector 1804 (e.g., mirror M2) opposite the first reflector and configured to produce multiple reflections of light therebetween. To decrease the total number of reflections, as shown in FIG. 18A, an angle A of incidence/reflection off the second reflector (M2) 1804 may be decreased and an angle B of incidence/reflection off the first reflector (M1) 1802 may be increased. This may be achieved by decreasing a radius of curvature C1 of M1 1802 and increasing a radius of the curvature C2 of M2 1804 according to the cell or cavity length. FIG. 18B illustrates the multiple reflection light pattern in both a normal Herriot cell and in the modified (asymmetrical) Herriot cell.

Figure 19:
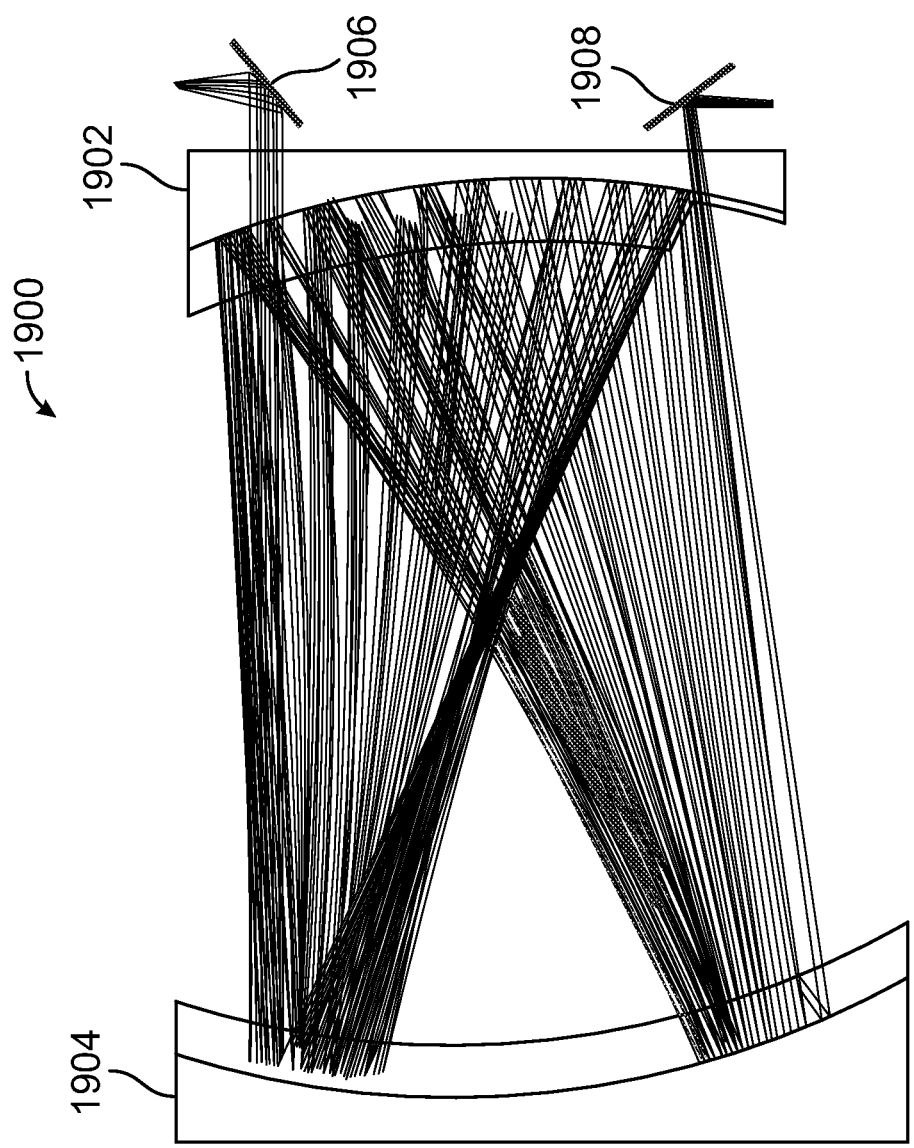
FIG. 19 is a diagram illustrating an example of an asymmetrical Herriot gas cell according to some aspects.

FIG. 19 is a diagram illustrating an example of an asymmetrical Herriot cell according to some aspects. An exemplary design of the asymmetric Herriot cell 1900 and the corresponding ray tracing is shown in FIG. 19. In the example shown in FIG. 19, the Herriot cell 1900 includes two reflectors 1902 and 1904 configured to produce multiple reflections therebetween. Each of the reflectors 1902 and 1904 has a different radius of curvature configured to reduce the total number of reflections. Light may enter the asymmetrical Herriot cell 1900, for example, after being collimated by an off-axis parabolic mirror 1906. Multiple reflections of light may then occur between the two reflectors 1902 and 1904 (e.g., mirrors M1 and M2). Output light may then exit the Herriot cell 1900 and be focused onto the spectrometer (not shown) by an off-axis parabolic mirror 1908.

In some examples, the Herriot gas cell may not be able to be evacuated frequently for practical reasons. Therefore, a background (e.g., reference) measurement in a frequent manner may not be possible, and thus time drift in the light source, detector or light modulation chip response, for example, due to aging, may cause non-accurate prediction by the AI engine. In some examples, this may be overcome using a self-calibration mechanism (e.g., corresponding to the self-calibration component 314/414 shown in FIGS. 3 and 4) in which the air is measured twice. One time with a path length $L_1$ and a second time with a path length $L_2$. The measured spectra $S_1$ and $S_2$ will be in the form of:

$$S_1 = P_{LS}(\lambda, t) R_d(\lambda, t) V_i(\lambda, t) \eta_1(\lambda) e^{-\alpha_{air}(\lambda) L_1} \quad \text{(Equation 1)}$$

$$S_2 = P_{LS}(\lambda, t) R_d(\lambda, t) V_i(\lambda, t) \eta_2(\lambda) e^{-\alpha_{air}(\lambda) L_2} \quad \text{(Equation 2)}$$

where $P_{LS}(\lambda, t)$ is the light source spectrum versus wavelength $\lambda$ at a given aging time t, $R_d(\lambda, t)$ is the detector responsivity, $V_i(\lambda, t)$ is the light modulation chip response, for example, interferometer visibility, $\eta$ is the coupling efficiency of the optics and $\alpha_{air}$ is the absorption coefficient of the gases in the air. By dividing the two measurements, a ratio may be obtained as follows:

$$S_1/S_2 = \eta_1/\eta_2 e^{-\alpha_{air}(\lambda)(L_1 - L_2)} \quad \text{(Equation 3)}$$

In this example, the ratio may be independent of the aging time. The AI calibration (or chemometrics) model may be trained using this ratio, and the prediction (e.g., result) can also be based on this ratio. For optimal detection with small limit of detection (LOD), the path $L_1$ can be maximized while the path $L_2$ is minimized.

FIGS. 20A and 20B are diagrams illustrating an example of a modified Herriot gas cell including a self-calibration component according to some aspects. The modified Herriot gas cell 2000 is an asymmetric Herriot gas cell that includes two reflectors (e.g., mirrors) 2002 and 2004 configured to produce multiple reflections therebetween. Each of the reflectors 2002 and 2004 has a different radius of curvature configured to reduce the total number of reflections. Input light is coupled into the asymmetric Herriot gas cell 2000 via an input optical coupling element (e.g., an input off-axis parabolic mirror) 2006 and output light exits the asymmetric Herriot gas cell and is redirected towards a spectrometer (not shown) via an output optical coupling element (e.g., an output off-axis parabolic mirror) 2008.

In the example shown in FIG. 20A, the self-calibration component corresponds to redirecting optical elements (e.g., mirrors) 2010 and 2012 that may be inserted into a light path of the modified Herriot cell 2000 to produce a short optical path length $L_2$. For example, the redirecting optical elements 2010 and 2012 may be inserted into the Herriot cell 2000 using a mechanical or electro-mechanical mechanism. Thus, the redirecting optical elements 2010 and 2012 may be configured to operate in a calibration mode to receive input light from the input optical coupling element 2006 and to redirect the input light through the Herriot gas cell without reflecting the light off either of the reflectors 2002 and 2004. The resulting output light may be directed towards the spectral sensor (not shown) via the output optical coupling element 2008, where a reference spectrum may be obtained.

In the example shown in FIG. 20B, the redirecting optical elements 2010 and 2012 may be removed from the light path of the asymmetric Herriot cell 2000 (e.g., via a mechanical or electro-mechanical mechanism) to produce a long optical path length $L_1$ and to enable a sample spectrum of a sample under test to be obtained in a measurement mode of the Herriot cell/gas analyzer. For example, input light may enter the asymmetric Herriot cell 2000 via the input optical coupling element 2006. Multiple reflections of light may then occur between the two reflectors 2002 and 2004 to allow the reflected light to interact with a sample (not shown). Output light may then exit the Herriot cell 2000 and be focused onto the spectral sensor by the output optical coupling element 2008.

By inserting the redirecting mirrors 2010 and 2102 into the modified Herriot cell 2000, the light system is common between the two measurements, with two optical path lengths $L_1$ and $L_2$ except for the optics inserted, which can change the coupling efficiency. This change in coupling efficiency may be kept time-independent by ensuring accurate placement of the optics from one measurement to another. Slight tolerance or misalignment may leads to a slight change, but this slight change is either wavelength independent or varies slowly with the wavelength as a baseline shift that can be overcome in the pre-processing in the AI engine.

In some examples, the secondary optical path (e.g., optical path length $L_2$) produced by the insertable redirecting optical elements 2010 and 2012 shown in FIG. 20A may be a temporary path used for background calibration. In some examples, the secondary optical path does not affect the main path power, alignment, or function. However, the received power at the detector should be within a sufficient level. The self-calibration component (e.g., redirecting optical elements 2010 and 2012) shown in FIG. 20A can be adapted for other gas cells with different path lengths that may be optimized per application depending on the requirements on the detection range and limit of detection.

Figure 21B:
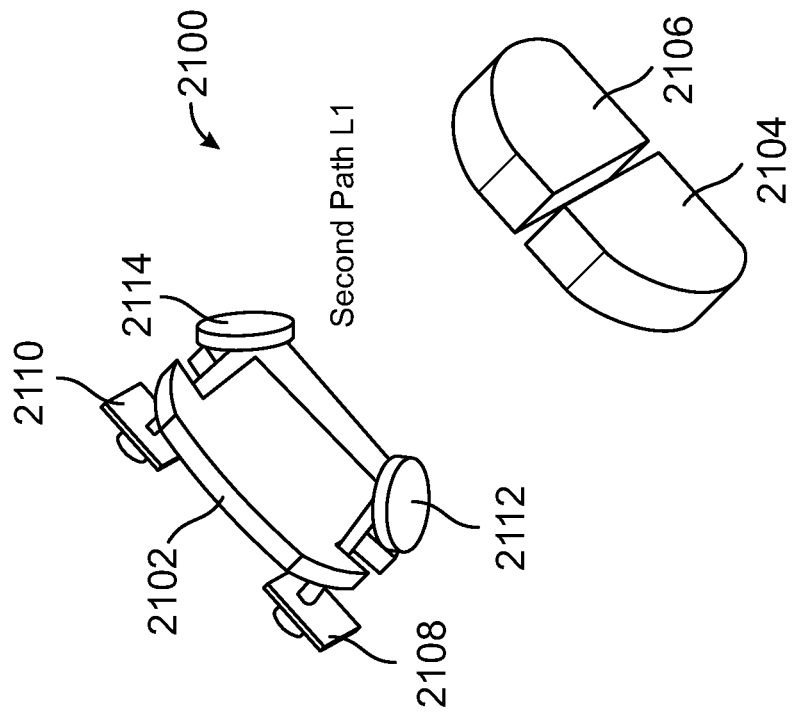
FIGS. 21A and 21B are diagrams illustrating an example of a White gas cell including a self-calibration component according to some aspects.
Figure 21A:
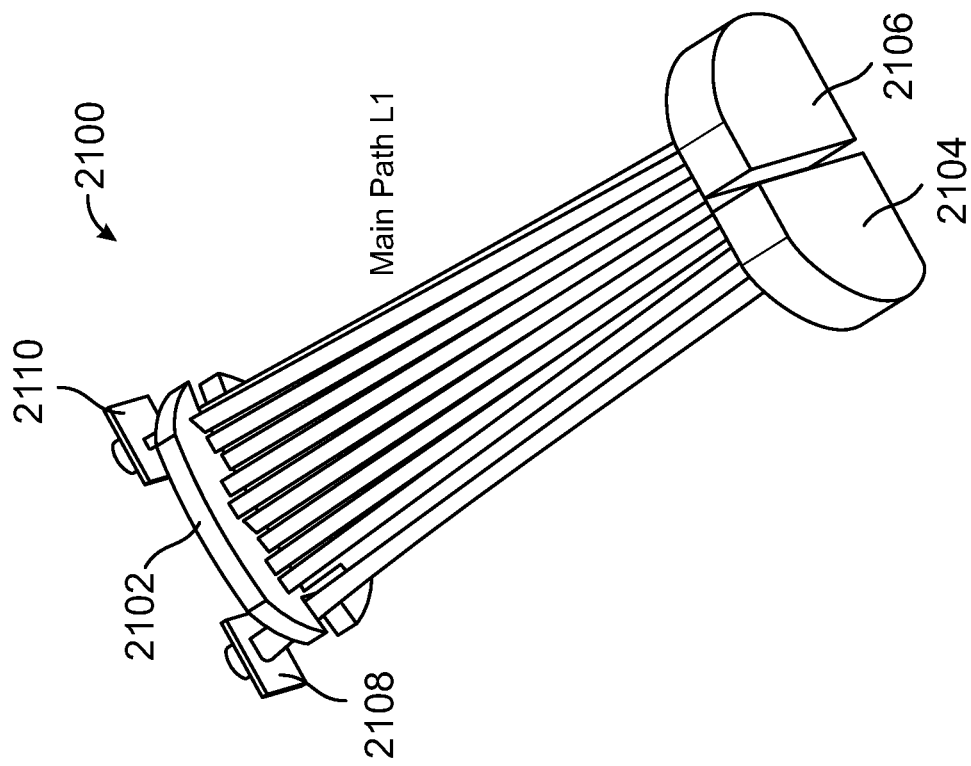

FIGS. 21A and 21B are diagrams illustrating an example of a White gas cell including a self-calibration component according to some aspects. The White gas cell includes three reflectors (e.g., mirrors) 2102, 2104, and 2106, an input optical coupling element (e.g., an input off-axis parabolic mirror) 2108, and an output optical coupling element (e.g., an output off-axis parabolic mirror) 2110. Each of the reflectors 2102, 2104, and 2106 may be a spherical mirror. In addition, each of the reflectors 2102, 2104, and 2106 may have the same radius of curvature that is equal to the separation (distance) between a larger spherical mirror 2102 on one side of the White gas cell 2100 and two smaller spherical mirrors 2104 and 2106 on the other side of the White gas cell 2100. For example, spherical mirror 2102 may have a length that is greater than the respective lengths of either of spherical mirrors 2104 and 2106. In addition, spherical mirrors 2104 and 2106 may be tilted with respect to one another to provide a small angle between the mirrors 2104 and 2106 selected to maintain the light within the White gas cell 2100.

In the example shown in FIG. 21A, the White gas cell 2100 provides a long optical path length $L_1$ to enable a sample spectrum of a sample under test to be obtained in a measurement mode of the White gas cell/gas analyzer. For example, input light can be coupled into the White gas cell 2100 via the input optical coupling element 2108. Multiple reflections of light may then occur between the longer reflector 2102 and each of shorter reflectors 2104 and 2106 making at least two passes up and down the multi-pass White gas cell 2100 to allow the reflected light to interact with a sample (not shown). Output light may then exit the White gas cell and is redirected towards a spectrometer (not shown) via an output optical coupling element (e.g., an output off-axis parabolic mirror) 2110.

In the example shown in FIG. 21B, the self-calibration component may include redirecting optical elements (e.g., two small mirrors) 2112 and 2114 that may be inserted into a light path of the White gas cell 2100 to switch from the main optical path $L_1$ to the secondary optical path $L_2$. In some examples, the inserted mirrors 2112 and 2114 can be of the same type and have the same coating material as the White cell reflectors 2102, 2104, and 2106, so that any degradation in the reflection will be common in the main optical path $L_1$ and the secondary optical path $L_2$. The second optical path directs the input light from the input optical coupling element 2108 into a U-turn path through the White gas cell 2100 towards the output optical coupling element 2110. Thus, the redirecting optical elements 2112 and 2114 may be configured to operate in a calibration mode to receive input light from the input optical coupling element 2108 and to redirect the input light through the White gas cell 2100 without reflecting the light off any of the reflectors 2102, 2104, and 2106 to enable a reference spectrum of a sample under test to be obtained. In some examples, the redirecting optical elements 2112 and 2114 can be flat mirrors with alignment angle drivers, curved mirrors with decentering drivers, or wedges with alignment angle drivers. Examples of curved mirrors include, but are not limited to, concave, convex, or toroidal mirrors. The inserted redirecting optical elements 2112 and 2114 should satisfy the alignment between the cell input light and the output cell light.

Figure 22:
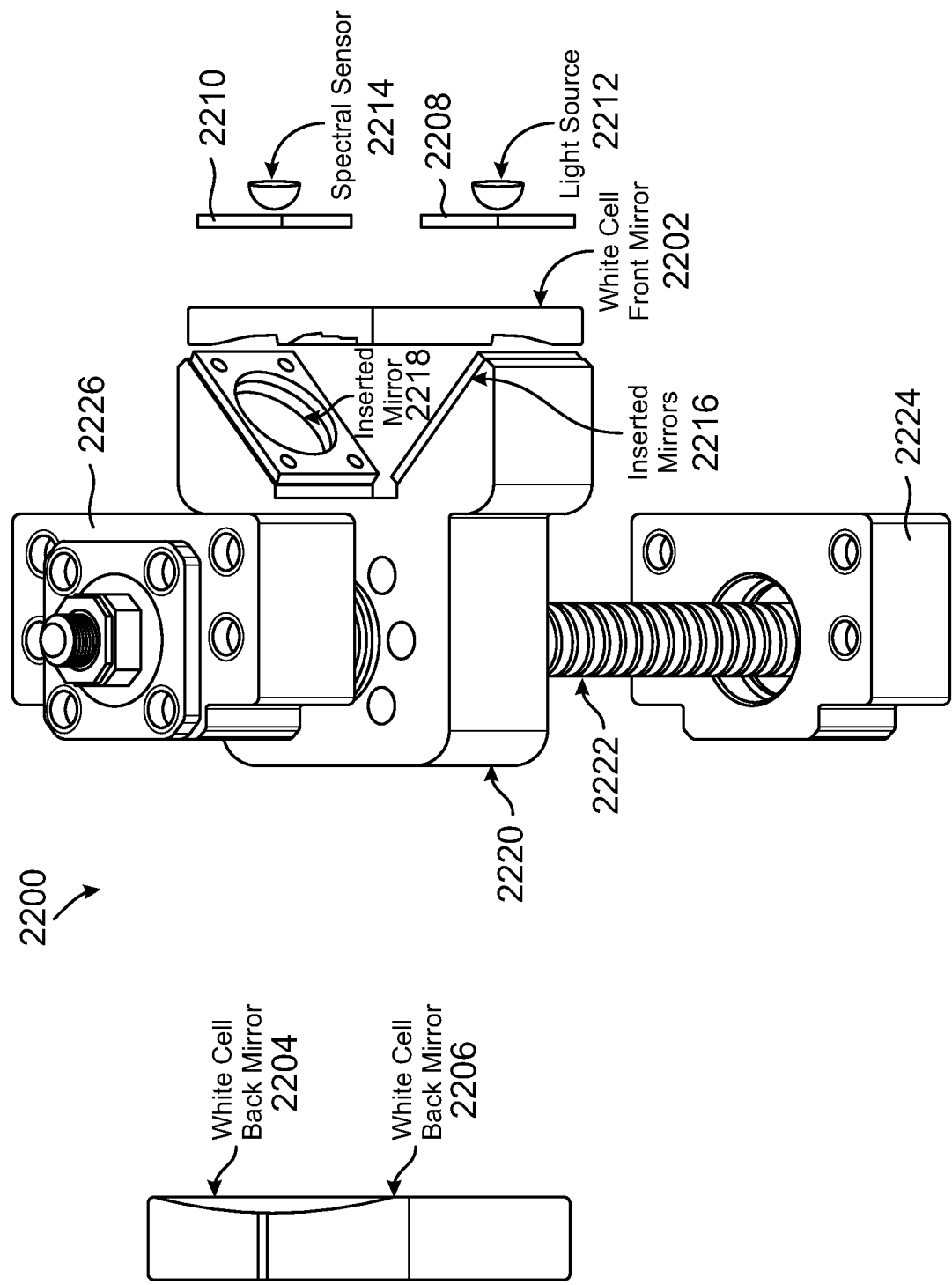
FIG. 22 is a diagram illustrating an example of an insertion mechanism for inserting redirecting optical elements into a White gas cell according to some aspects.

FIG. 22 is a diagram illustrating an example of an insertion mechanism for inserting redirecting optical elements into a White gas cell according to some aspects. The White gas cell 2200 includes three reflectors (e.g., mirrors) 2202, 2204, and 2206, an input optical coupling element (e.g., an input off-axis parabolic mirror) 2208, and an output optical coupling element (e.g., an output off-axis parabolic mirror) 2210. Input light from a light source 2212 may be input to the White gas cell 2200 via the input optical coupling element 2208 and output light from the White gas cell 2200 may be coupled towards a spectral sensor (or detector) 2214 via the output optical coupling element 2210.

Redirecting optical elements 2216 and 2218 corresponding to the self-calibration component are mounted on a holder 2220. The holder 2220 may be coupled to a lead screw 2222 (e.g., through a nut). The lead screw 2222 may be coupled to a bearing mechanism 2224 on one side and to a stepper motor 2226 on the other side for insertion and removal of the redirecting optical elements 2216 and 2218 into and out of the light path of the White gas cell 2200, as described above in connection with FIG. 21.

Figure 23:
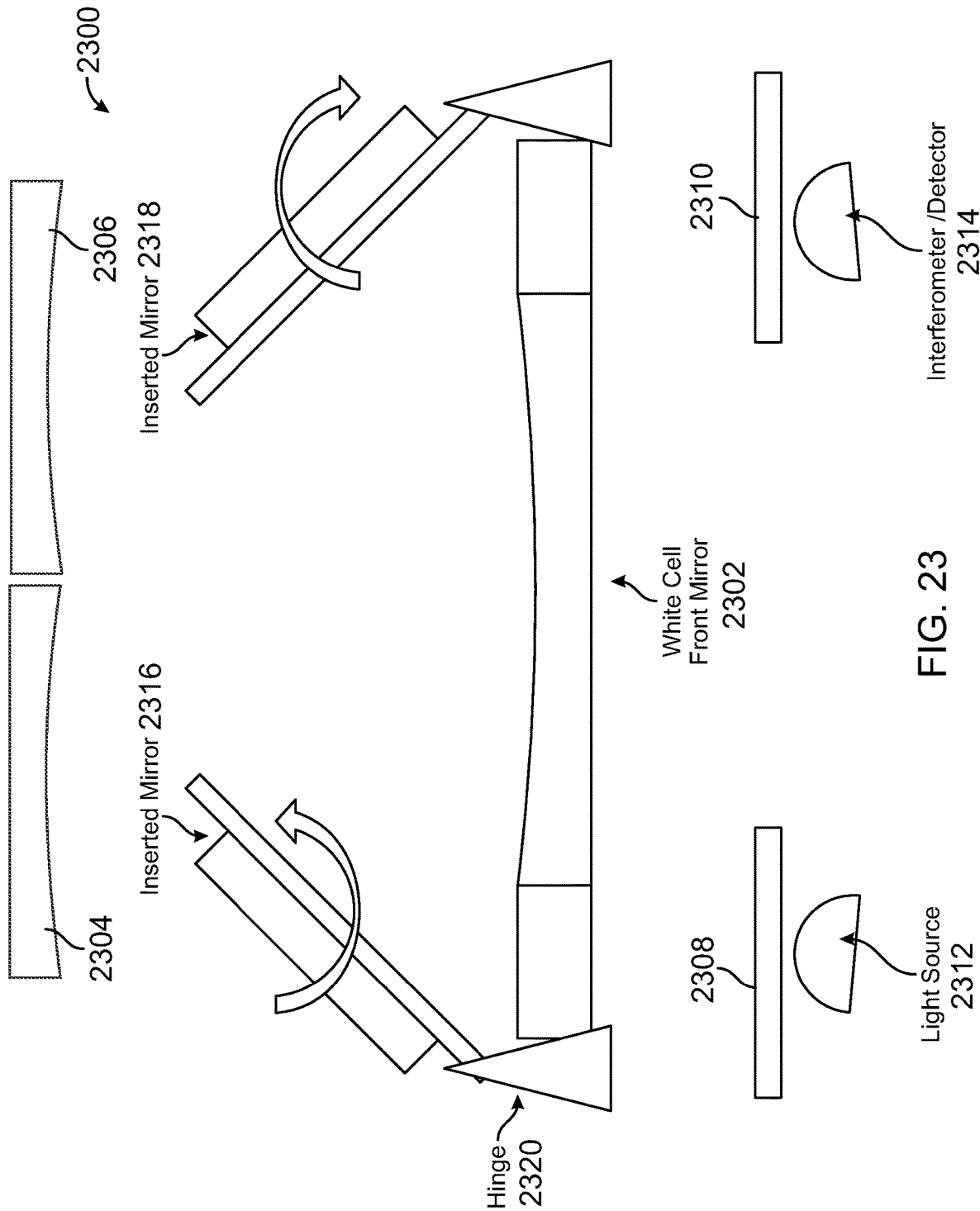
FIG. 23 is a diagram illustrating another example of an insertion mechanism for inserting redirecting optical elements into a White gas cell according to some aspects.

FIG. 23 is a diagram illustrating another example of an insertion mechanism for inserting redirecting optical elements into a White gas cell according to some aspects. The White gas cell 2300 includes three reflectors (e.g., mirrors) 2302, 2304, and 2306, an input optical coupling element (e.g., an input off-axis parabolic mirror) 2308, and an output optical coupling element (e.g., an output off-axis parabolic mirror) 2310. Input light from a light source 2312 may be input to the White gas cell 2300 via the input optical coupling element 2308 and output light from the White gas cell 2300 may be coupled towards a spectral sensor (or detector) 2314 via the output optical coupling element 2310.

Redirecting optical elements 2316 and 2318 corresponding to the self-calibration component may be inserted and removed from the light path of the White gas cell 2200 using a rotational motion instead of a translation motion as shown in FIG. 22. The rotation can be around a hinge 2320 located at the sides of the White gas cell large reflector 2302. The insertion mechanism shown in FIG. 23 reduces the overall size of the gas analyzer (e.g., as compared to the insertion mechanism shown in FIG. 22), and does not complicate the optical design, since the redirecting optical elements 2316 and 2318 are not blocking any part of the light when the redirecting optical elements 2316 and 2318 are not inserted into the light path.

Figure 24A:
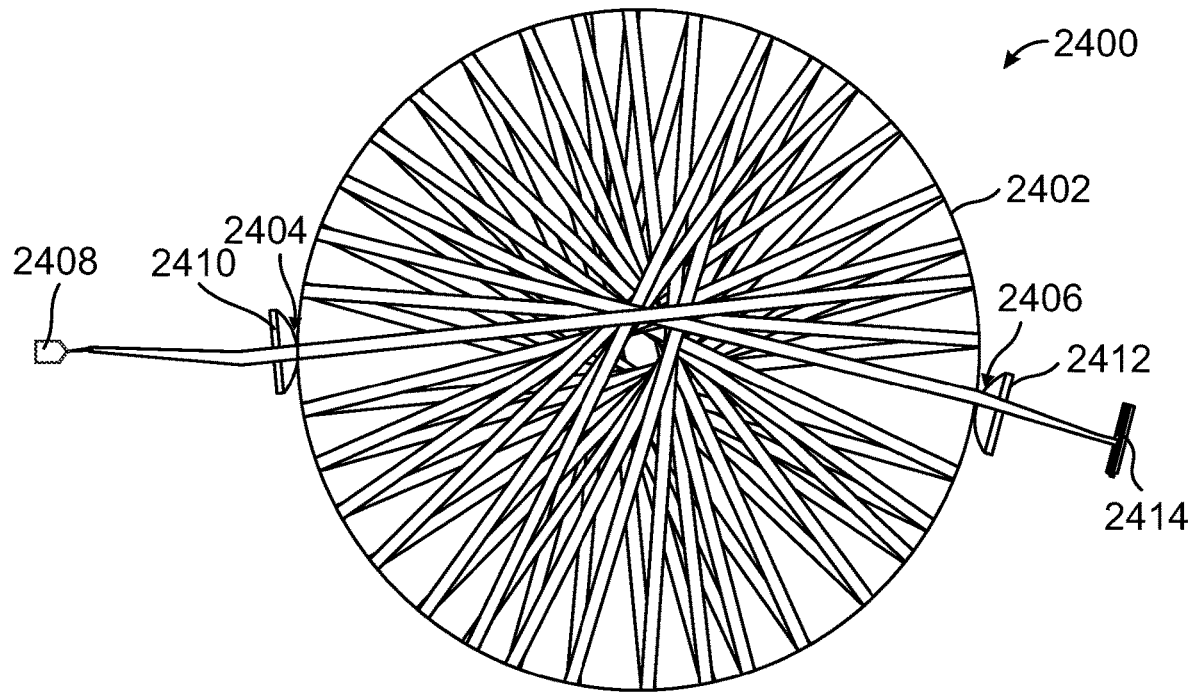
FIGS. 24A and 24B illustrate an example of a circular gas cell including a self-calibration component according to some aspects.
Figure 24B:
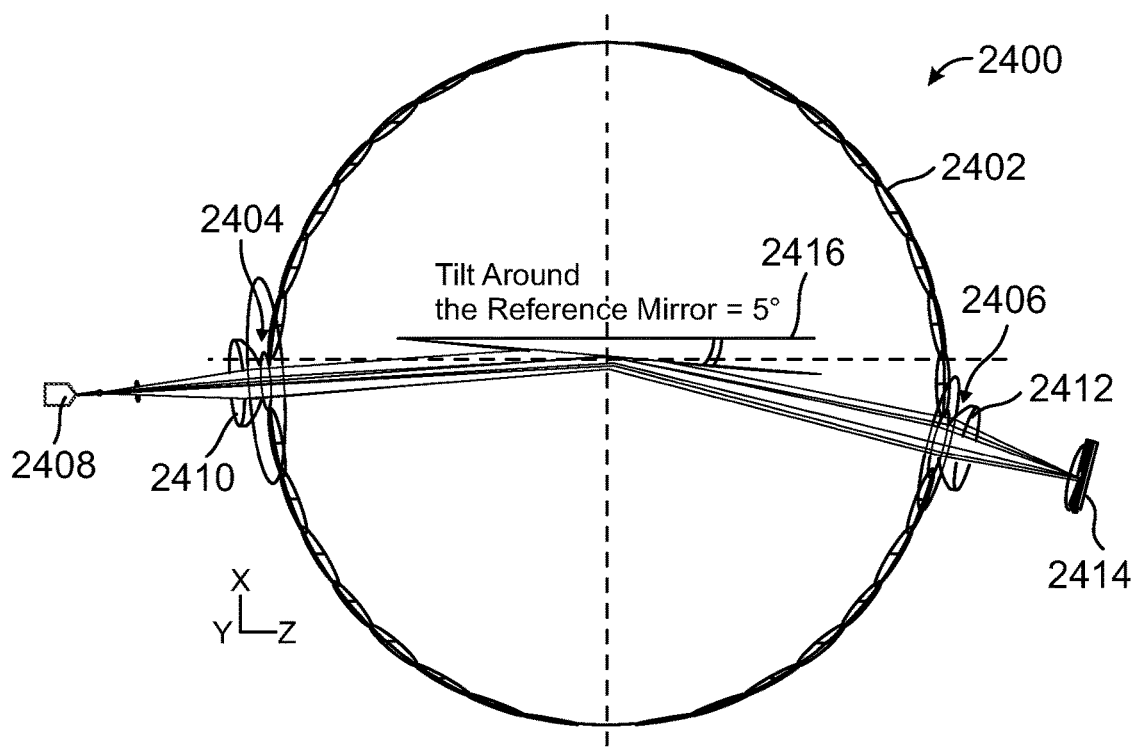

FIGS. 24A and 24B illustrate an example of a circular gas cell including a self-calibration component according to some aspects. As shown in FIG. 24A, the circular gas cell 2400 includes a circular reflecting element 2402, an input 2404 and an output 2406. Input light from a light source 2408 may be provided to the input 2404 of the circular gas cell 2400 via an input optical coupling element 2410 (e.g., one or more lenses or mirrors, such as an off-axis parabolic mirror). In a measurement mode of the circular gas cell/gas analyzer, multiple reflections of the input light may occur within the circular gas cell 2400 around the circular reflecting element 2402 to produce light interaction with a sample under test within the circular gas cell 2400. Output light may be directed via the output 2406 to an output optical coupling element 2412, which is configured to couple the output light to a spectral sensor (or detector) 2414 to obtain a sample spectrum of the sample.

In some examples, the circular gas cell 2400, in the simplest shape, can be considered as a portion of sphere. In this example, the total path and number of reflections can be changed by tilting the input light away from the center of the sphere or by decentering the input light away from the center of the sphere (e.g., by five degrees). Different numbers of reflections and path lengths may be obtained using these two different options. However, the light at the circular gas cell output may spread and the light energy may be decreased. Therefore, in some examples, small divergence light sources such as lasers, may be used. However, the filament sources power may be decreased dramatically if used in this type of circular cell 2400. Thus, in the filament source example, an array of spherical or toroidal mirrors may be included as the output optical coupling element 2412 to prevent the spreading of the light at the output 2406 of the circular cell 2400.

As shown in FIG. 24B, the self-calibration component can include a flat mirror 2416 that may be inserted into the light path of the circular gas cell 2400. When inserted, the flat mirror 2416 is configured to operate in a calibration mode to receive the input light via the input optical coupling element 2410 and to redirect the input light through the circular gas cell 2400 without reflecting off the circular reflecting element 2402 towards the output optical coupling element 2412 to obtain a reference spectrum. In some examples, the center of the flat mirror 2416 passes through the circle center of the circular gas cell 2400. In addition, the flat mirror 2416 may be, for example, 60 mm by 10 mm, with a tilt around the flat mirror 2416 being five degrees.

FIGS. 25A and 25B are diagrams illustrating an exemplary gas analyzer including a self-calibration component external to the gas cell according to some aspects. The gas analyzer 2500 includes a gas cell 2502 (e.g., a Herriot gas cell or modified/asymmetric Herriot gas cell including reflectors 2504 and 2506, though other types of gas cells may be used), optical coupling elements 2508 and 2510, a light source 2512, and a spectral sensor 2514 (e.g., spectrometer and associated detector). In a measurement mode of the gas analyzer 2500, as shown in FIG. 25A, incident light 2516 produced by the light source 2512 may be coupled into the gas cell 2502 as input light via an input optical coupling element 2508 (e.g., an off-axis parabolic mirror). The input light 2516 may be reflected between the two reflectors 2504 and 2506 to cause light interaction with a sample (not shown) within the gas cell 2502. Output light 2518 from the gas cell 2502 may be coupled to the spectral sensor 2514 via an output optical coupling element 2510 (e.g., an off-axis parabolic mirror) to obtain a sample spectrum of the sample.

In the example shown in FIG. 25B, the self-calibration component includes external reflectors 2520 and 2522 outside of the gas cell 2502 and configured to operate in a calibration mode to receive the incident light 2516 produced by the light source 2512 and to produce reference light 2524 reflected towards the spectral sensor 2514 to obtain a reference spectrum without the sample. In some examples, the external reflectors 2520 and 2522 are coupled to an actuator 2526 that may be controlled, for example, by a control/processor chipset (e.g., control circuitry 316/416 shown in FIGS. 3 and 4). Thus, in the calibration mode, self-referencing of the gas analyzer 2500 can be achieved automatically without the need for manual intervention or the need to pump the sample under test from the gas cell 2500. The external reflectors 2520 and 2522 outside of the gas cell 2502 can be moved in-plane in-between the main optical coupling elements 2508 and 2510 and the gas cell 2502 to operate in the calibration mode, and then can be moved automatically out-of-plane to operate in the measurement mode. The external reflectors 2520 and 2522 prevent the incident light 2516 from entering the gas cell 2500 and direct the incident light 2516 to be coupled directly to the spectral sensor 2514 for measuring the background reference spectrum.

Figures 26A, 26B:
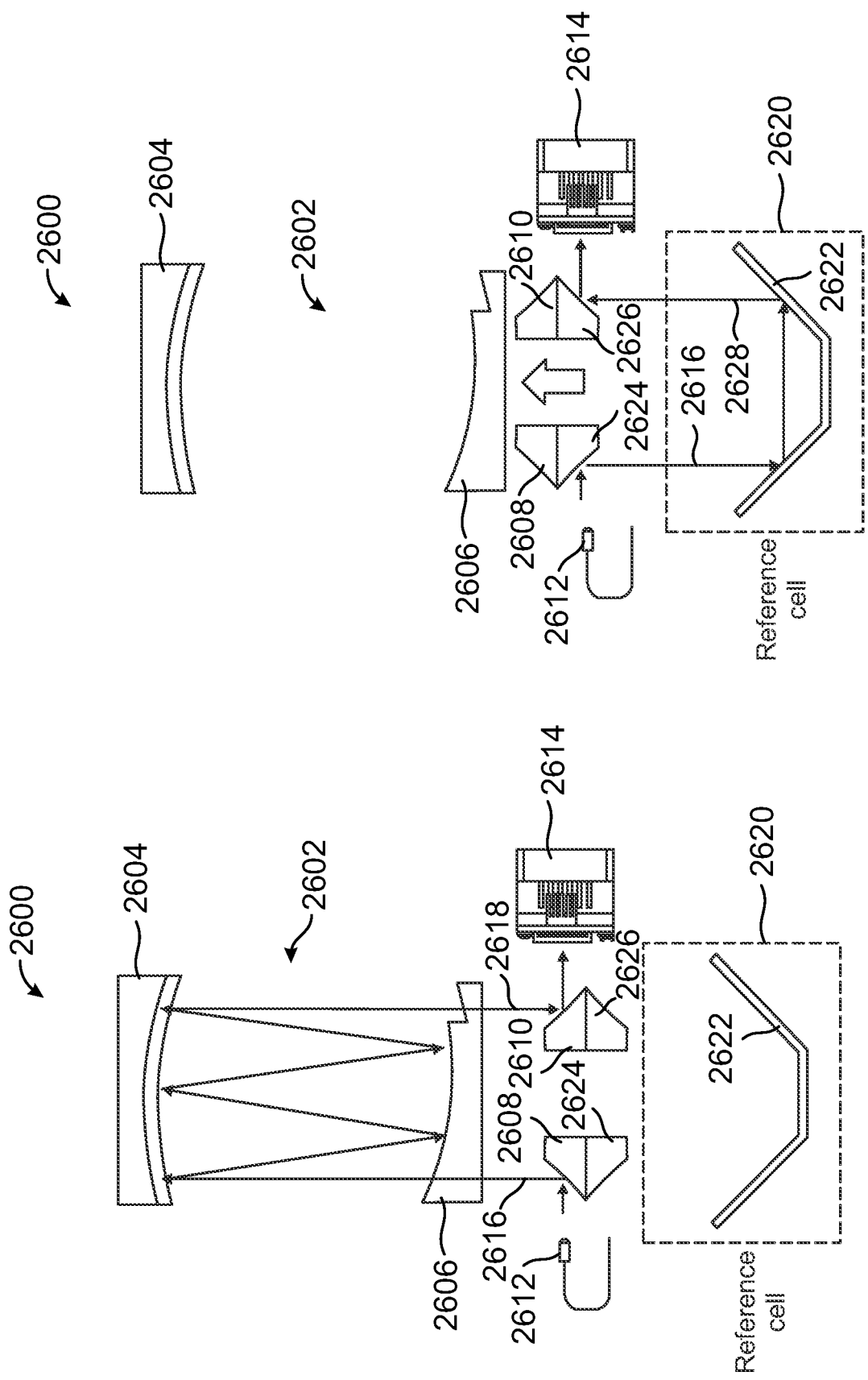
FIGS. 26A and 26B are diagrams illustrating another exemplary gas analyzer including a self-calibration component external to the gas cell according to some aspects.

FIGS. 26A and 26B are diagrams illustrating another exemplary gas analyzer including a self-calibration component external to the gas cell according to some aspects. The gas analyzer 2600 includes a gas cell 2602 (e.g., a Herriot gas cell or modified/asymmetric Herriot gas cell including reflectors 2604 and 2606, though other types of gas cells may be used), optical coupling elements 2608 and 2610, a light source 2612, and a spectral sensor 2614 (e.g., spectrometer and associated detector). In a measurement mode of the gas analyzer 2600, as shown in FIG. 26A, incident light 2616 produced by the light source 2612 may be coupled into the gas cell 2602 as input light via an input optical coupling element 2608 (e.g., an off-axis parabolic mirror). The input light 2616 may be reflected between the two reflectors 2604 and 2606 to cause light interaction with a sample (not shown) within the gas cell 2602. Output light 2618 from the gas cell 2602 may be coupled to the spectral sensor 2614 via an output optical coupling element 2610 (e.g., an off-axis parabolic mirror) to obtain a sample spectrum of the sample.

The self-calibration component in the example shown in FIGS. 26A and 26B includes two external reflectors 2624 and 2626 and a reference cell 2620 including a reference reflector 2622. The two external reflectors 2624 and 2426 are attached to the main reflectors (e.g., optical coupling elements 2608 and 2610), such that the four reflectors 2608, 2610, 2624, and 2626 are moveable together (e.g., via an actuator as in the example shown in FIGS. 25A and 25B). In the measurement mode, as shown in FIG. 26A, the two main reflectors 2608 and 2610 are aligned with the light source 2612 to direct the incident light 2616 along a gas cell path. In a calibration mode, as shown in FIG. 26B, the external reflectors 2624 and 2626 are aligned with the light source 2612 to direct the incident light 2616 along a reference cell path. For example, the incident light 2616 may be directed by a first external reflector 2624 into the reference gas cell 2620. The reference gas cell 2620 may be configured to receive the incident light reflected from the first external reflector 2624 and to reflect the incident light 2616 towards the second external reflector 2626 to produce reference light 2628 for reflection by the second external reflector 2626 towards the spectral sensor 2614. In some examples, the reference gas cell 2620 can be a vacuum sealed cell or a cell of a short length to minimize the absorption of any gases in the air inside the cell.

FIGS. 27A and 27B are diagrams illustrating another exemplary gas analyzer including a self-calibration component external to the gas cell according to some aspects. The gas analyzer 2700 includes a gas cell 2702 (e.g., a Herriot gas cell or modified/asymmetric Herriot gas cell including reflectors 2704 and 2706, though other types of gas cells may be used), optical coupling elements 2708 and 2710, a light source 2712, and a spectral sensor 2714 (e.g., spectrometer and associated detector). In a measurement mode of the gas analyzer 2700, as shown in FIG. 27A, incident light 2716 produced by the light source 2712 may be coupled into the gas cell 2702 as input light via an input optical coupling element 2708 (e.g., an off-axis parabolic mirror). The input light 2716 may be reflected between the two reflectors 2704 and 2706 to cause light interaction with a sample (not shown) within the gas cell 2702. Output light 2718 from the gas cell 2702 may be coupled to the spectral sensor 2714 via an output optical coupling element 2710 (e.g., an off-axis parabolic mirror) to obtain a sample spectrum of the sample.

The self-calibration component in the example shown in FIGS. 27A and 27B includes an actuator 2720 coupled to the optical coupling elements 2708 and 2710 (e.g., main reflectors). In this example, the actuator 2720 may be configured to move the main reflectors 2708 and 2710 away from the gas cell light path during calibration mode. Thus, the incident light 2716 produced by the light source 2712 may be coupled directly into the spectral sensor 2714 without passing through the gas cell 2702 and without being redirected by the main reflectors 2708 and 2710 or any other reflector.

FIGS. 28A and 28B are diagrams illustrating other exemplary gas analyzer configurations including a self-calibration component external to the gas cell according to some aspects. The gas analyzers 2800a and 2800b shown in FIGS. 28A and 28B each include a gas cell 2802 (e.g., a Herriot gas cell or modified/asymmetric Herriot gas cell including reflectors 2804 and 2806, though other types of gas cells may be used), optical coupling elements 2808 and 2810, a light source 2812, and a spectral sensor 2814 (e.g., spectrometer and associated detector). In a measurement mode of the gas analyzer 2800a, as shown in FIG. 28A, incident light 2816 produced by the light source 2812 may be coupled into the gas cell 2802 as input light via an input optical coupling element 2808 (e.g., an off-axis parabolic mirror). The input light 2816 may be reflected between the two reflectors 2804 and 2806 to cause light interaction with a sample (not shown) within the gas cell 2802. Output light 2818 from the gas cell 2802 may be directed towards the spectral sensor 2814 via an output optical coupling element 2810 (e.g., an off-axis parabolic mirror) to obtain a sample spectrum of the sample.

In the example shown in FIGS. 28A and 28B, the self-calibration component includes two external reflectors 2820 and 2822 outside of the gas cell 2802 and configured to operate in a calibration mode to receive the incident light 2816 produced by the light source 2812 and to produce reference light 2826 reflected towards the spectral sensor 2814 to obtain a reference spectrum without the sample. The self-calibration component further includes a shutter 2824 configured to switch between the calibration mode and the measurement mode. For example, the shutter 2824 can be configured to block the reference light path during the measurement mode by blocking the incident light 2816 from reaching the second external reflector 2822.

In the example shown in FIG. 28A, a beam combiner 2828 may be used to couple light from both the reference light path and the sample path (through the gas cell 2802) to the spectral sensor 2814. During reference measurement in calibration mode, the shutter 2824 may block the sample path (e.g., by blocking the output light 2818 from reaching the combiner 2828) to be able to measure the reference spectrum separately, or the shutter 2824 may allow both paths to be coupled to the spectral sensor 2814, such that the summation of the two spectra is collected. To extract the reference spectrum, the sample spectrum may be subtracted from the sum. For example, the beam combiner 2828 may be configured to combine the output light 2818 and the reference light 2826 for input to the spectral sensor 2814 to produce a combined spectrum in the calibration mode. The spectral sensor 2814 may then be configured to extract the reference spectrum from the combined spectrum by subtracting the sample spectrum from the combined spectrum.

In some examples, the beam combiner 2828 can be in the form of typical beam splitter with a selected splitting ratio to maximize the coupled power from the sample path. Another option shown in FIG. 28B includes a transmission diffuser 2832, where the two beams of the two paths are focused onto the transmission diffuser 2832. For example, the output light 2818 from the sample light path (e.g., from the gas cell 2802) may be directed towards the transmission diffuser 2832 via the main optical coupling element 2810, while the reference light 2826 from the reference light path (e.g., from the second external reflector 2822) may be directed towards the transmission diffuser 2832 via an additional reflector 2830. The output transmitted beam from the transmission diffuser 2832 can be considered as a new Lambertian source combining/mixing the two beams (output light 2818 and reference light 2826), which may be directed towards the spectral sensor 2814.

Figure 29A:
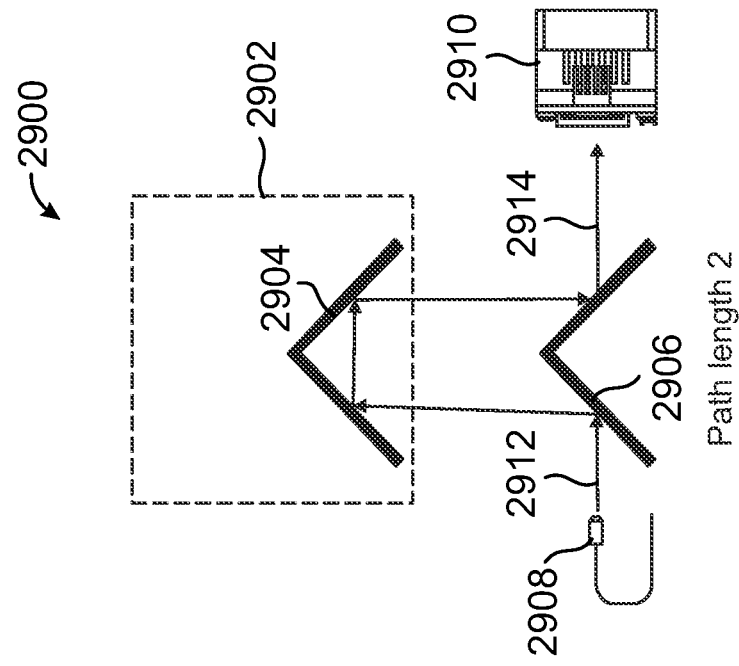
FIGS. 29A and 29B are diagrams illustrating an exemplary gas analyzer including a self-calibration component within the gas cell according to some aspects.
Figure 29B:
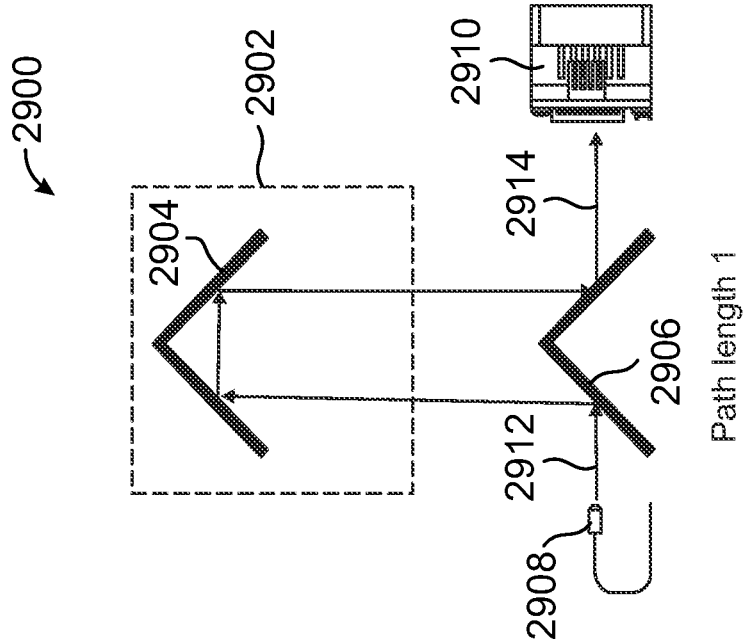

FIGS. 29A and 29B are diagrams illustrating an exemplary gas analyzer including a self-calibration component within the gas cell according to some aspects. The gas analyzer 2900 includes a gas cell 2902 including a reflector 2904, an optical coupling element 2906, a light source 2908, and a spectral sensor 2910. The reflector 2904 may be a moveable reflector. For example, the moveable reflector 2904 may be coupled to an actuator for switching between a measurement mode (e.g., as shown in FIG. 29A) and a calibration mode (e.g., as shown in FIG. 29B). Incident light 2912 from the light source 2908 may be coupled via the optical coupling element (e.g., fixed reflector) 2906 into the gas cell 2902. The light may then be directed towards the moveable reflector 2904, which further reflects the light back towards the fixed reflector 2906 to produce output light/reference light 2914 coupled into the spectral sensor 2910.

In the example shown in FIGS. 29A and 29B, self-referencing can be achieved by measuring the spectra of the gas cell 2902 at two different path lengths by moving the moveable reflector 2904 between a first position in the measurement mode and a second position in a calibration mode. In the measurement mode, as shown in FIG. 29A, the spectral sensor 2910 may receive the output light 2914 from the gas cell 2902 produced based on light interaction with a sample (not shown) within the gas cell 2902 to obtain a sample spectrum corresponding to a long path length (Path length 1) inside the gas cell 2902. In the calibration mode, as shown in FIG. 29B, the spectral sensor 2910 may receive the reference light 2914 from the gas cell 2902 to obtain a reference spectrum corresponding to a short path length (Path length 2) inside the gas cell 2902.

Figures 30A, 30B:
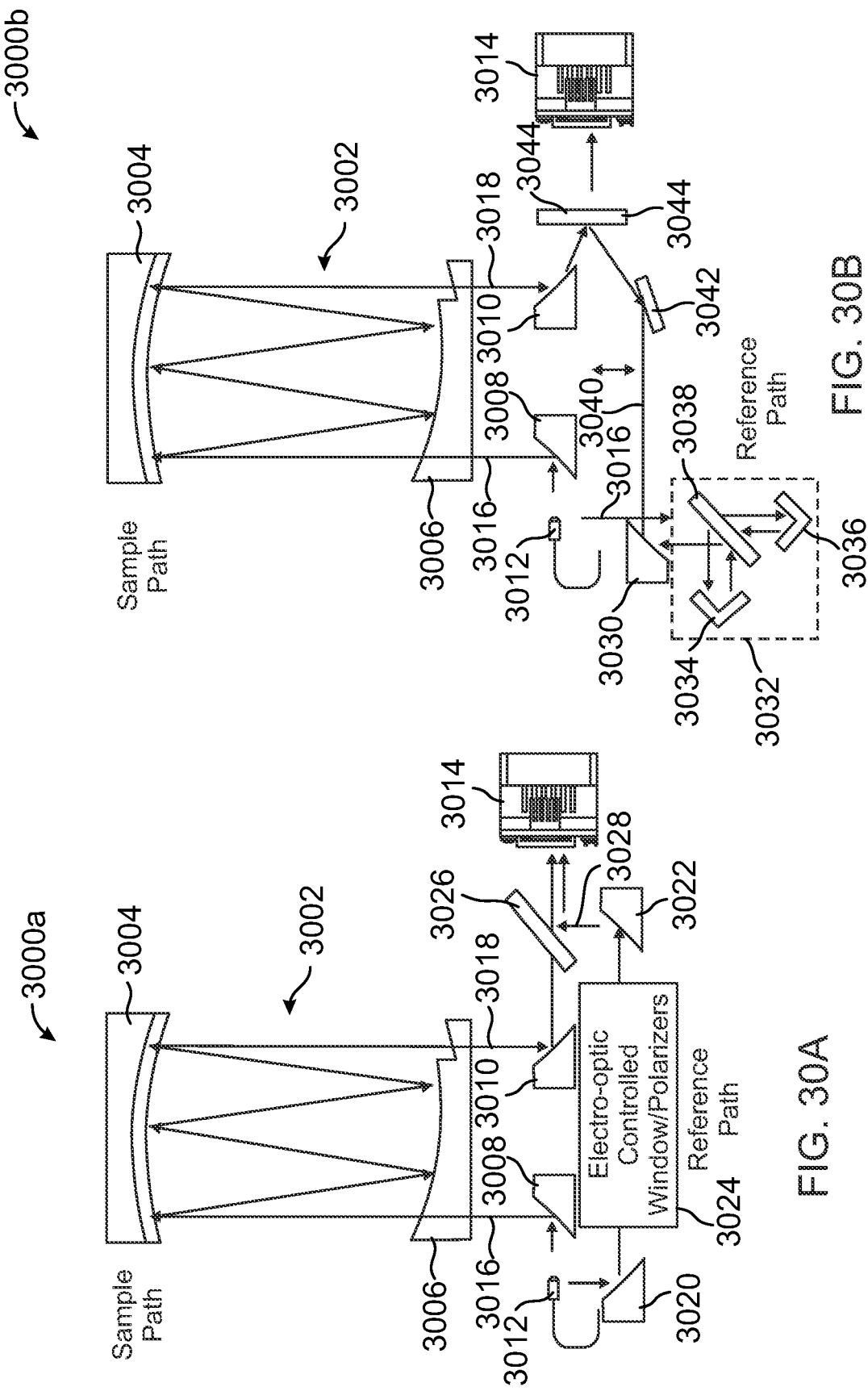
FIGS. 30A and 30B are diagrams illustrating other exemplary gas analyzer configurations including a self-calibration component external to the gas cell according to some aspects.

FIGS. 30A and 30B are diagrams illustrating other exemplary gas analyzer configurations including a self-calibration component external to the gas cell according to some aspects. The gas analyzers 3000a and 3000b shown in FIGS. 30A and 30B each include a gas cell 3002 (e.g., a Herriot gas cell or modified/asymmetric Herriot gas cell including reflectors 3004 and 3006, though other types of gas cells may be used), optical coupling elements 3008 and 3010, a light source 3012, and a spectral sensor 3014 (e.g., spectrometer and associated detector). In a measurement mode of the gas analyzer 3000, as shown in FIG. 30A, incident light 3016 produced by the light source 3012 may be coupled into the gas cell 3002 as input light via an input optical coupling element 3008 (e.g., an off-axis parabolic mirror). The input light 3016 may be reflected between the two reflectors 3004 and 3006 to cause light interaction with a sample (not shown) within the gas cell 3002. Output light 3018 from the gas cell 3002 may be directed towards the spectral sensor 3014 via an output optical coupling element 3010 (e.g., an off-axis parabolic mirror) to obtain a sample spectrum of the sample.

In the example shown in FIG. 30A, the self-calibration component includes external reflectors 3020 and 3022 outside of the gas cell 3002 configured to operate in a calibration mode to receive the incident light 3016 produced by the light source 3012 and to produce reference light 3028 reflected towards the spectral sensor 3014 to obtain a reference spectrum without the sample. The self-calibration component further includes an electro-optic controlled element 3024 configured to switch between the calibration mode and the measurement mode. For example, the electro-optic controlled element 3024 can be configured to block the reference light path during the measurement mode by blocking the incident light 3016 from reaching the second external reflector 3022. In some examples, the electro-optic controlled element 3024 may be an electro-optic controlled-transmittance window of special material or an electrically controlled polarizer.

The gas analyzer 3000 further includes a beam combiner 3026 configured to couple light from both the reference light path and the sample path (through the gas cell 3002) to the spectral sensor 3014. During sample measurement in measurement mode, the electro-optic controlled element 3024 may block the reference path (e.g., by blocking the incident light 3016 from reaching the second external reflector 3022) to be able to measure the sample spectrum. In calibration mode, the electro-optic controlled element 3024 may allow both paths to be coupled to the spectral sensor 3014, such that the summation of the two spectra is collected. To extract the reference spectrum, the sample spectrum may be subtracted from the sum.

In the example shown in FIG. 30B, the self-calibration component includes an interferometer 3032, which may include retro-reflectors 3034 and 3036 and a beam splitter 3038. One of the retro-reflectors 3034 and 3036 may be a moveable mirror configured to produce an optical path length difference between the two arms (e.g., the two light paths) of the interferometer 3032. The optical path length difference between the two arms (light paths) in the interferometer may be controlled to enable switching between the calibration mode and the measurement. For example, in a measurement mode, the optical path length difference may be controlled to produce an output interference pattern (e.g., reference light 3040) adjusted to near the interferogram null. In calibration mode, the optical path length may be controlled to produce the reference light 3040 for a background measurement. The reference light 3040 may be coupled to a transmission diffuser 3044 via a coupling mirror 3042, where the reference light 3040 of the reference path and the output light 3018 of the sample path are focused onto the transmission diffuser 3044. The output from the transmission diffuser 3044 may be directed towards the spectral sensor 3014.

Figure 31:
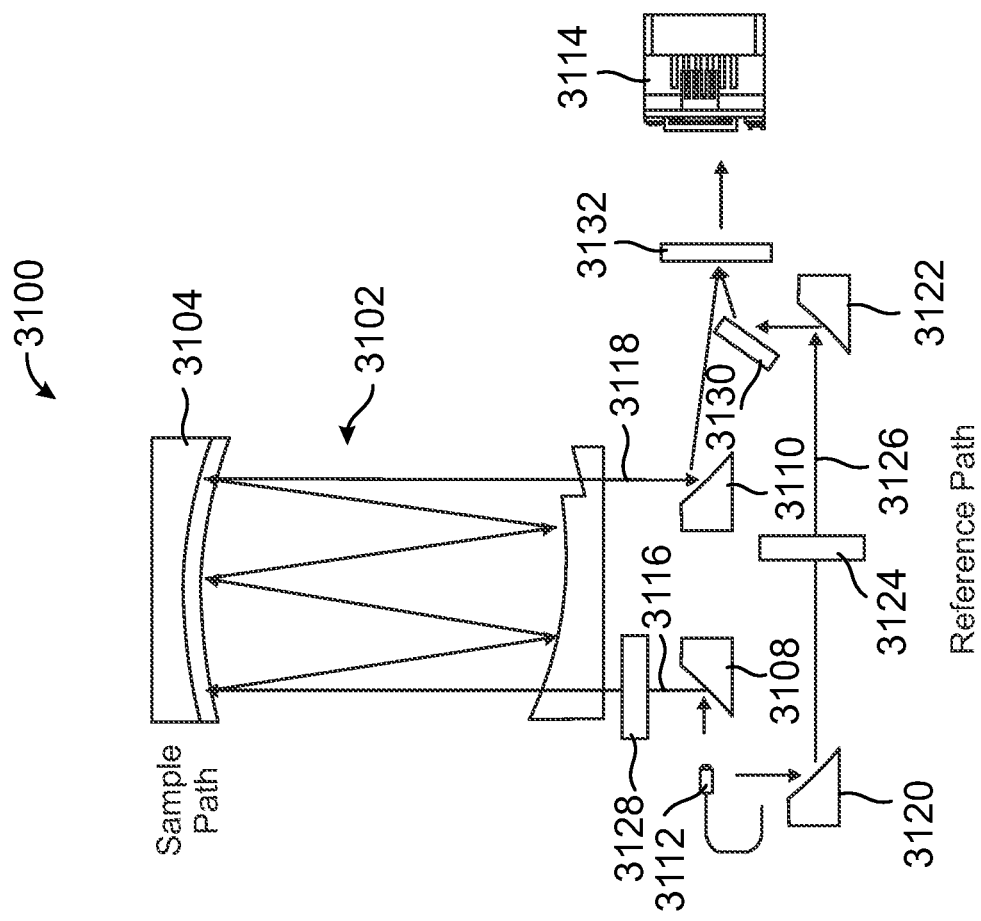
FIG. 31 is a diagram illustrating another exemplary gas analyzer configuration including a self-calibration component external to the gas cell according to some aspects.

FIG. 31 is a diagram illustrating another exemplary gas analyzer configuration including a self-calibration component external to the gas cell according to some aspects. The gas analyzer 3100 includes a gas cell 3102 (e.g., a Herriot gas cell or modified/asymmetric Herriot gas cell including reflectors 3104 and 3106, though other types of gas cells may be used), optical coupling elements 3108 and 3110, a light source 3112, and a spectral sensor 3114 (e.g., spectrometer and associated detector). In the measurement mode of the gas analyzer 3100, incident light 3116 produced by the light source 3112 may be coupled into the gas cell 3102 as input light via an input optical coupling element 3108 (e.g., an off-axis parabolic mirror). The input light 3116 may be reflected between the two reflectors 3104 and 3106 to cause light interaction with a sample (not shown) within the gas cell 3102. Output light 3118 from the gas cell 3102 may be directed towards the spectral sensor 3114 via an output optical coupling element 3110 (e.g., an off-axis parabolic mirror) to obtain a sample spectrum of the sample.

The self-calibration component includes external reflectors 3120 and 3122 outside of the gas cell 3102 configured to operate in a calibration mode to receive the incident light 3116 produced by the light source 3112 and to produce reference light 3126 reflected towards the spectral sensor 3114 to obtain a reference spectrum without the sample. The self-calibration component further includes an optical bandpass filter 3124 coupled between the external reflectors 3120 and 3122 and configured to produce the reference light 3126 including reference bands for input to the spectral sensor 3114. Thus, the bandpass filter 3124 is configured to pass certain bands from reference path to be detected and monitored for baseline drifts compensation. Another complementary bandstop filter 3128 can be added in the sample path to filter-out the bands passed by the bandpass filter 3124. The filter bands passed by the bandpass filter 3124 may be selected to be away from the important bands of the sample under test. In the example shown in FIG. 31, the reference light 3126 may be coupled to a transmission diffuser 3132 via a coupling mirror 3130, where the reference light 3126 of the reference path and the output light 3118 of the sample path are focused onto the transmission diffuser 3132. The output from the transmission diffuser 3142 may be directed towards the spectral sensor 3114.

Figures 32A, 32B:
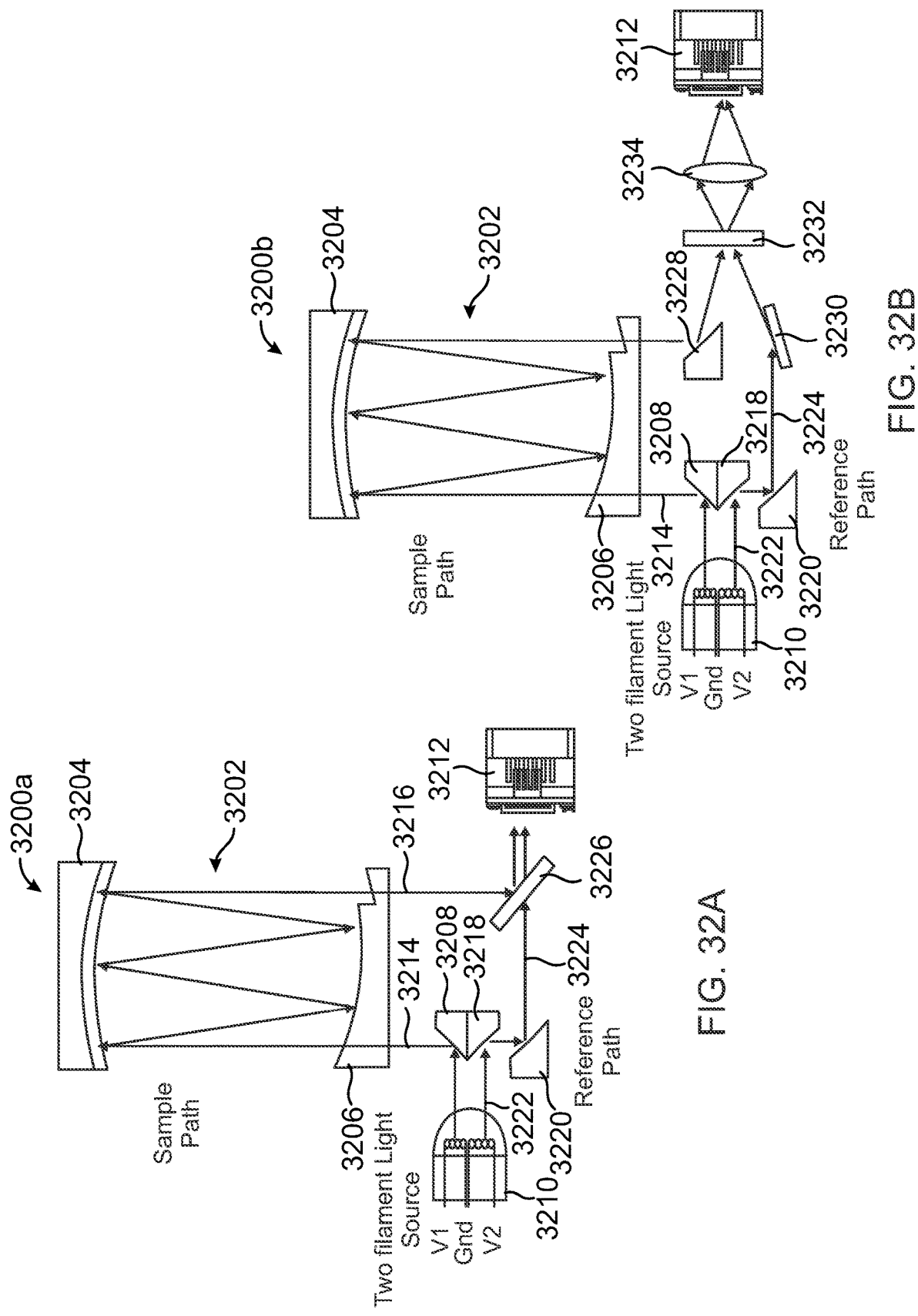
FIGS. 32A and 32B are diagrams illustrating other exemplary gas analyzer configurations including a self-calibration component external to the gas cell according to some aspects.

FIGS. 32A and 32B are diagrams illustrating other exemplary gas analyzer configurations including a self-calibration component external to the gas cell according to some aspects. The gas analyzers 3200*a* and 3200*b* shown in FIGS. 32A and 32B each include a gas cell 3202 (e.g., a Herriot gas cell or modified/asymmetric Herriot gas cell including reflectors 3204 and 3206, though other types of gas cells may be used), an optical coupling element 3208, a light source 3210, and a spectral sensor 3212 (e.g., spectrometer and associated detector). The light source 3210 is a dual filament light source including two adjacent filaments electrically separated with two different voltage terminals and a common ground terminal. Each filament is coupled to one of the sample path and the reference path. The two filaments can be switched in the time-domain, synchronized with the spectral sensor operation.

In the example shown in FIG. 32A, in the measurement mode, incident light 3214 (e.g., first input light) produced by one of the filaments of the light source 3210 may be coupled into the gas cell 3202 as input light via an input optical coupling element 3208 (e.g., an off-axis parabolic mirror). The input light 3214 may be reflected between the two reflectors 3204 and 3206 to cause light interaction with a sample (not shown) within the gas cell 3202. Output light 3216 from the gas cell 3202 may be directed towards the spectral sensor 3212 to obtain a sample spectrum of the sample.

The self-calibration component includes two external reflectors 3218 and 3220 (e.g., off-axis parabolic mirrors) outside of the gas cell 3202 and configured to operate in a calibration mode to receive incident light 3222 (e.g., second input light) produced by the other filament of the light source 3210 and to produce reference light 3224 reflected towards the spectral sensor 3212 to obtain a reference spectrum without the sample. A first external reflector 3218 is attached to the main reflector 3208 and aligned to receive the second input light 3222. A beam combiner 3226 may be used to couple light from both the reference light path and the sample path (through the gas cell 3202) to the spectral sensor 3212. In examples in which the dual filament light source 3210 is configured to switch between the first input light 3214 and the second input light 3222, the gas analyzer 3200 may be configured to separately operate in measurement mode and calibration mode to obtain separate sample spectra and reference spectra. In some examples, during calibration mode, the light source 3210 may be configured to simultaneously produce both the first input light 3214 via the first filament and the second input light 3222 via the second filament. In this example, both the sample and reference paths may be coupled to the spectral sensor 3212 via the combiner 3226, such that the summation of the two spectra is collected. To extract the reference spectrum, the sample spectrum may be subtracted from the sum.

In the example shown in FIG. 32B, the two beams of the two paths (sample and reference) are focused onto a transmission diffuser 3232. For example, the output light 3216 from the sample light path (e.g., from the gas cell 3202) may be directed towards the transmission diffuser 3232 via an additional optical coupling element 3228, while the reference light 3224 from the reference light path (e.g., from the external reflector 3220) may be directed towards the transmission diffuser 3232 via an additional reflector (mirror) 3230. The output transmitted beam (combining/mixing the output light 3216 and reference light 3224) from the transmission diffuser 3232 can be focused on spectral sensor 3214 via a lens 3234.

Figure 33:
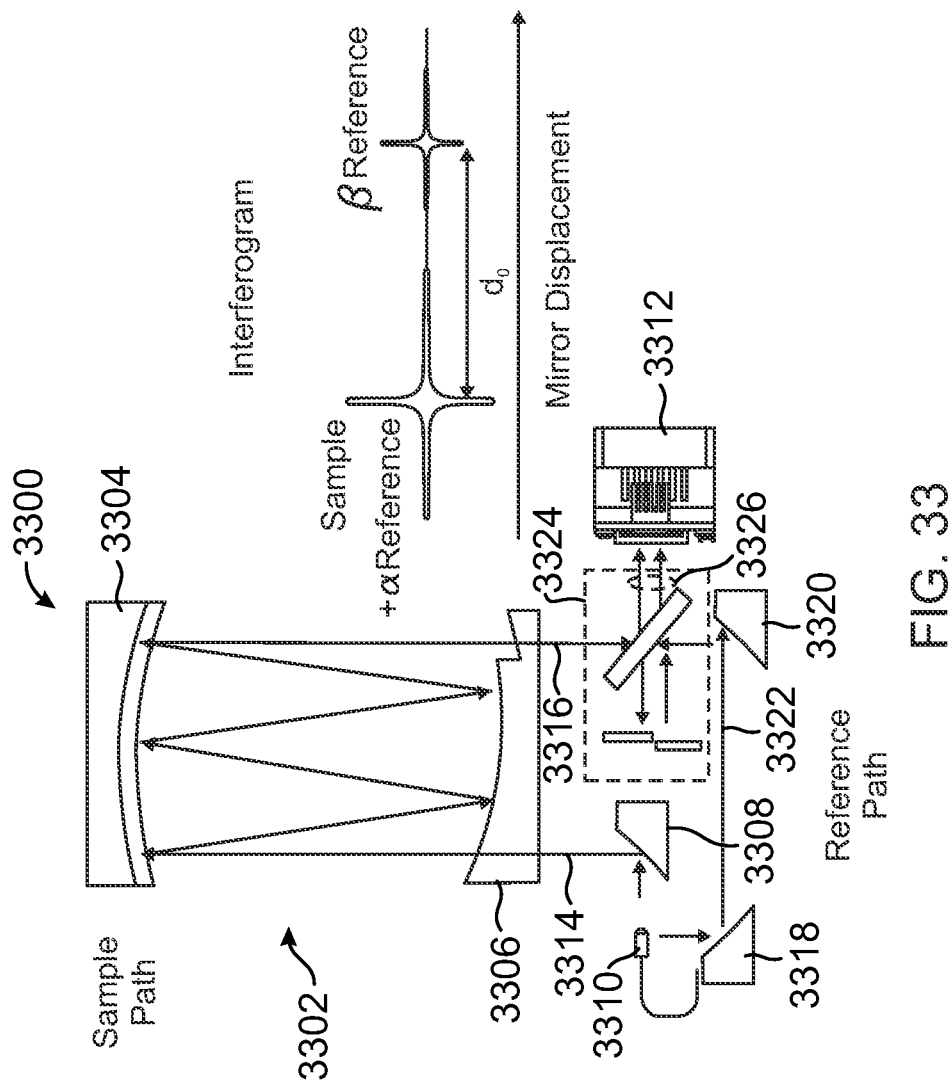
FIG. 33 is a diagram illustrating another exemplary gas analyzer configuration including a self-calibration component external to the gas cell according to some aspects.

FIG. 33 is a diagram illustrating another exemplary gas analyzer configuration including a self-calibration component external to the gas cell according to some aspects. The gas analyzer 3300 includes a gas cell 3302 (e.g., a Herriot gas cell or modified/asymmetric Herriot gas cell including reflectors 3304 and 3306, though other types of gas cells may be used), an optical coupling element 3308, a light source 3310, and a spectral sensor 3312 (e.g., spectrometer and associated detector). In the measurement mode of the gas analyzer 3300, incident light 3314 produced by the light source 3310 may be coupled into the gas cell 3302 as input light via an input optical coupling element 3308 (e.g., an off-axis parabolic mirror). The input light 3314 may be reflected between the two reflectors 3304 and 3306 to cause light interaction with a sample (not shown) within the gas cell 3302. Output light 3316 from the gas cell 3302 may be directed towards the spectral sensor 3312 to obtain a sample spectrum of the sample.

The self-calibration component includes external reflectors 3318 and 3320 outside of the gas cell 3302 configured to operate in a calibration mode to receive the incident light 3314 produced by the light source 3310 and to produce reference light 3322 reflected towards the spectral sensor 3312 to obtain a reference spectrum without the sample. In the example shown in FIG. 33, self-referencing of the gas analyzer 3300 is achieved using a Michelson interferometer 3324 with a two-level mirror M in one of its arms. The interferometer 3324 can be added before the spectral sensor 3312. The two levels of the mirror M lead to two reflected half-beams of an optical path difference $2d_o$ corresponding to double the mirror step. The output of the interferometer 3326 is a modulated light beam in spectral domain, with a relatively slow cosine function corresponding to the mirror step size, while another very fast sine function exists due to the interference between the sample path and the reference path as follows:

$$P=P_s(1+\cos(2kd_o))+P_{ref}-2\sqrt{P_s P_{ref}}\sin(k(L_{ref}-L_s-d_o))\quad\text{(Equation 4)}$$

where $P_s$ is the sample path power, $P_{ref}$ is the reference path coupled power to the output of the interferometer, $L_{ref}$ is the reference path length, and $L_s$ is the sample path length. Such fast variations are due to the very long optical path difference between the two paths, and as such, a high resolution spectrometer (e.g., of the spectral sensor 3212) is needed to capture the difference. Given that, the interferogram signal of the spectral sensor 3212 may include a secondary burst at a spectral sensor interferometer moveable mirror distance $d_o$. The mirror step $d_o$ may be adjusted to result in the secondary burst being outside the interferogram window corresponding to the target resolution. The reference spectrum can be extracted from the secondary burst, and then the main burst signal can be corrected to extract the sample spectrum.

The self-referencing example shown in FIG. 33 can be used for self-correction as well, where the secondary burst position with respect to the main burst position can be used as a reference optical path difference to correct for any wavenumber drifts that may be due to optical path difference drifts.

Figure 34:
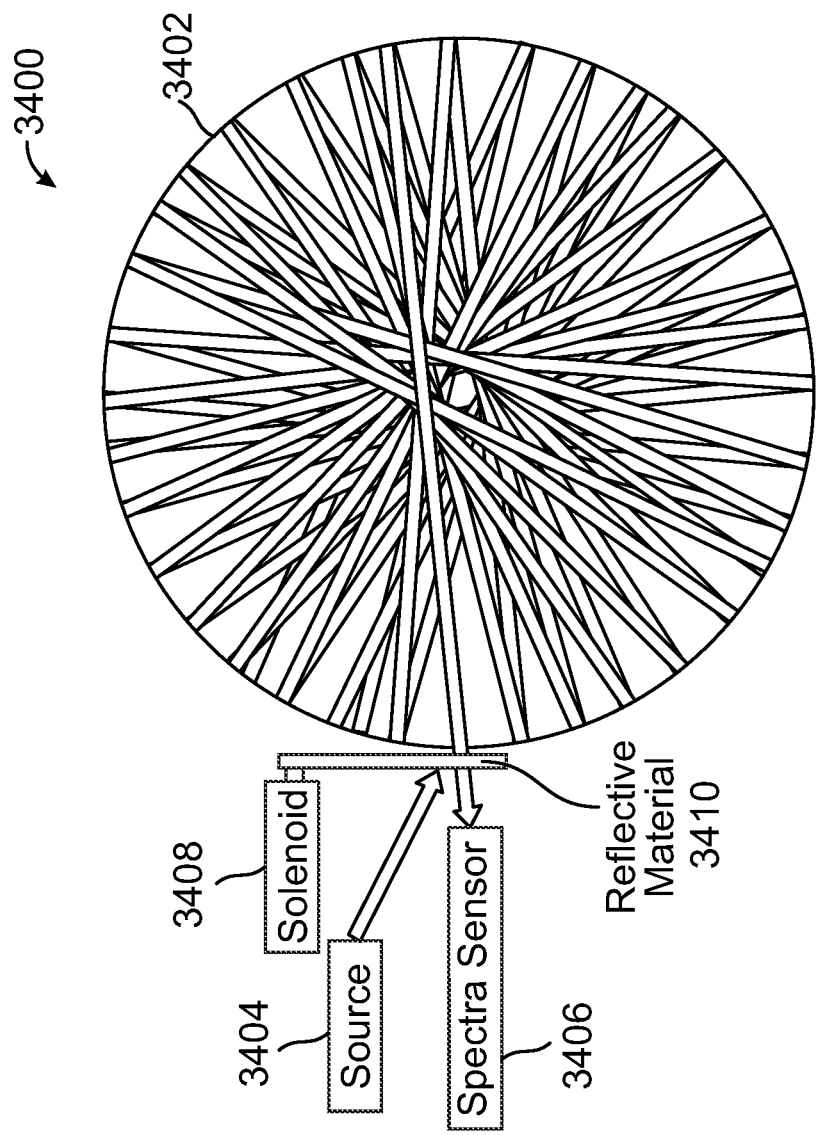
FIG. 34 illustrates an example of a gas analyzer including a self-calibration component external to a circular gas cell according to some aspects.

FIG. 34 illustrates an example of a gas analyzer including a self-calibration component external to a circular gas cell according to some aspects. As shown in FIG. 34, the gas analyzer 3400 includes a circular gas cell 3402, a light source 3404, and a spectral sensor 3406. The circular gas cell 3402 may be, for example, a single input/output toroidal gas cell, where the input is collimated light and the output light may be directed towards the spectral sensor 3406 to obtain a sample spectrum. In the example shown in FIG. 34, the self-calibration component may include a solenoid 3408 attached to a reflective material 3410 that enables the source/detector 3404/3406 to be internal reference corrected. In this example, the reflective material 3410 may further operate as a mirror for focusing the output light onto the spectral sensor 3406 during measurement mode to obtain a sample spectrum. In addition, the solenoid 3408 may be configured to move the reflective material 3410 into a light path of the incident light from the light source 3404 in a calibration mode to prevent the incident light from entering the toroidal gas cell 3202 and to couple the incident light to the spectral sensor 3406 to obtain a reference spectrum. Thus, the background measurement is acquired while the incident light is reflected directly from the reflective material 3410, and the solenoid 3408 is configured to move the reflective material 3410 away in order to allow the incident light to enter the gas cell 3402 to measure the sample under test. In some examples, the solenoid 3408 may be more robust to shock vibrations than moving mechanical mirrors, and may also be less sensitive.

Figure 35:
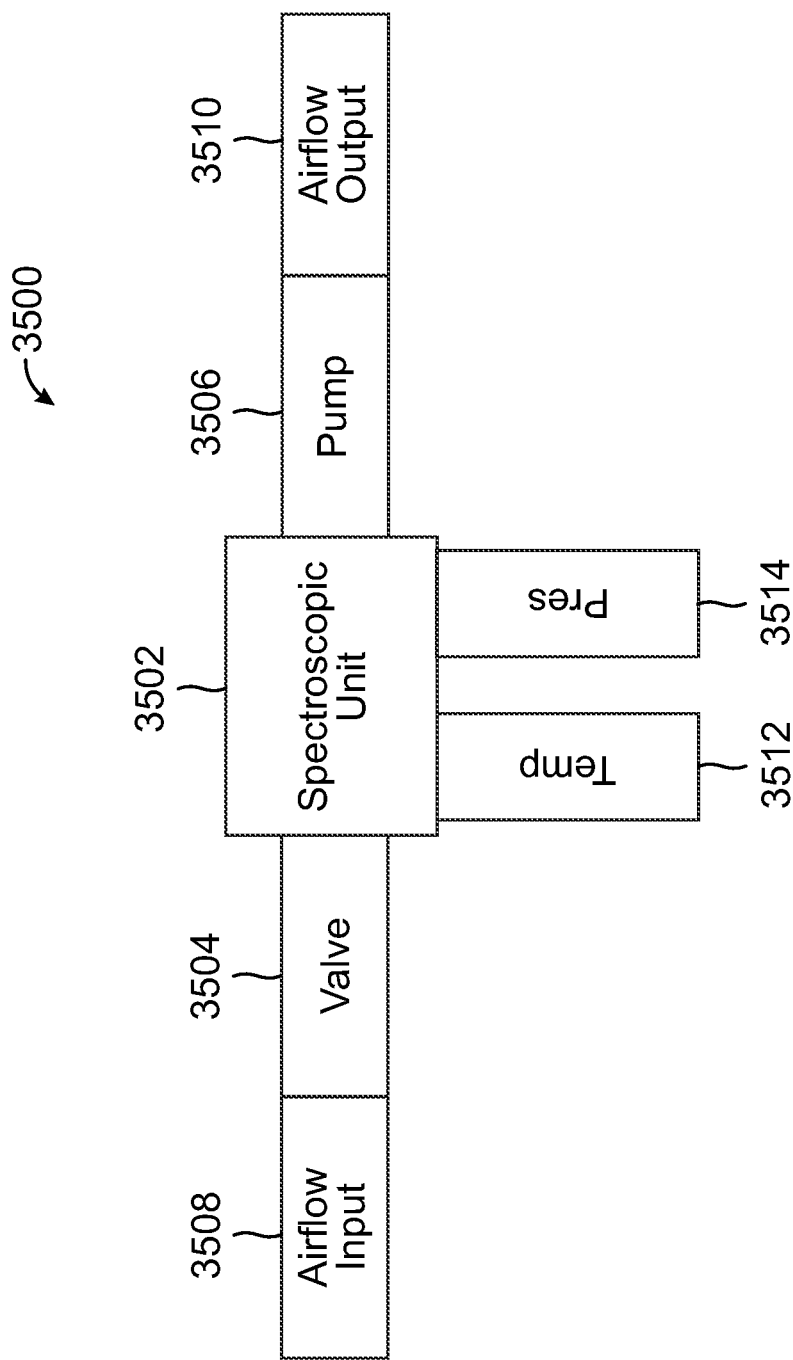
FIG. 35 is a diagram illustrating an example of a gas analyzer enabling a real-time reference background measurement according to some aspects.

FIG. 35 is a diagram illustrating an example of a gas analyzer enabling a real-time reference background measurement according to some aspects. The gas analyzer 3500 includes a spectroscopic unit 3502 (e.g., at least a light source, gas cell, and spectral sensor). The spectroscopic unit may be coupled to a valve 3504 configured to allow airflow from an airflow input 3508 to enter the spectroscopic unit 3502 for sample measurement. In addition, the valve 3504 is further configured to stop the airflow into the spectroscopic unit 3502. A downstream pump 3506, which may be located adjacent to or removed from the spectroscopic unit 3506 is configured to pump the air out of the spectroscopic unit 3502 towards an airflow output 3510. By closing the valve 3504 while the pump 3506 is on, a pseudo vacuum may be created in the spectroscopic unit 3502, thus enabling a background measurement (e.g., reference spectrum) to be obtained while no (or minimal) gas is present in the gas cell of the spectroscopic unit 3502. This enables an online/real-time reference background measurement. The gas analyzer 3500 may further include a temperature sensor 3512 and a pressure sensor 3514 configured to measure the temperature and pressure of the spectroscopic unit 3502. The temperature and pressure measurements (e.g., sensor data) may be fed into an AI engine (not shown) to enable offset correction based on the temperature and pressure values. In addition, pumping while partially closing the valve (or having a secondary valve) may change the pressure and increase the dynamic range of the measurement by decreasing the amount of gas in the spectroscopic unit 3502.

In some examples, as described above, the self-calibration component may be included in the AI engine (e.g., AI engine 312/412 shown in FIGS. 3 and 4). For example, the AI engine may be configured to perform self-referencing by using a special treatment of the measured spectra. In one example, a reference wavelength among the whole span of the measured wavelengths where the absorbance is independent of the sample under test concentration may be determined. Based on the reference wavelength, information regarding external fluctuations (drift, aging, etc.) can be measured according to the absorbance change at the reference wavelength and the spectrum can be corrected accordingly.

In another example, self-referencing may be performed by inserting a well-designed optical filter with specific transmission values at the different wavelengths ($t_1$ at $\lambda_1$, $t_2$ at $\lambda_2$, $t_3$ at $\lambda_3$ and so on) when re-calibration is needed. Taking advantage of the well-known relation between the different transmission values ($t_1$, $t_2$, $t_3$, etc. . . . ), the AI engine may correct the spectrum accordingly by removing the effect of any drift or aging with time of the different optical components in the system. In addition, this filter may be measured continuously without removal if it is designed with maximum transmission values at the wavelengths of interest where the sample absorption peaks exist to avoid any interference or loss in the signal to noise ratio. Light source drifts can be also compensated using dedicated photodetector(s) to monitor optical power drift of the light source within the band of interest or outside the band of interest.

Figure 36:
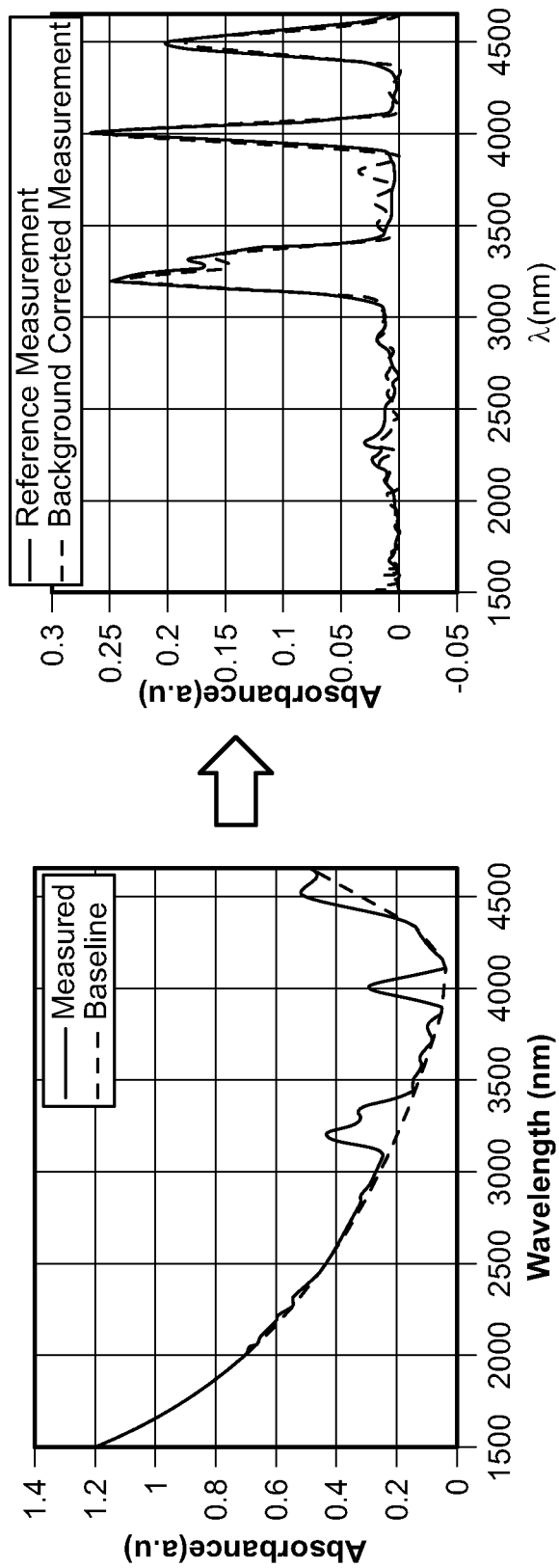
FIG. 36 is a diagram illustrating an example of self-calibration by the AI engine according to some aspects.

FIG. 36 is a diagram illustrating an example of self-calibration by the AI engine according to some aspects. To avoid measuring the background when it is not suitable for practical reasons, the background may be estimated using the AI engine by estimating the baseline for each sample measurement separately while considering it as the background and then subtracting the baseline to extract the superimposed peaks, which are the peaks of interest associated with the sample under test as shown by the sample measurement in FIG. 36.

In some examples, the gas sample under test may be pre-concentrated before introducing the sample into the gas cell. Pre-concentration of the sample may increase the capability of having a low limit of detection (LOD) and being able to measure very low concentrations of gases, such as in the case of measuring volatile organic compounds (VOCs). Different sorbent materials, such as Tenax, Carboxen, and other suitable materials may be used based on the gas under test in which the gas molecules are adsorbed by the sorbent materials. In this example, the gases may be released when the sorbent material is heated, leading to have a high concentration of the gas under test.

Figure 37:
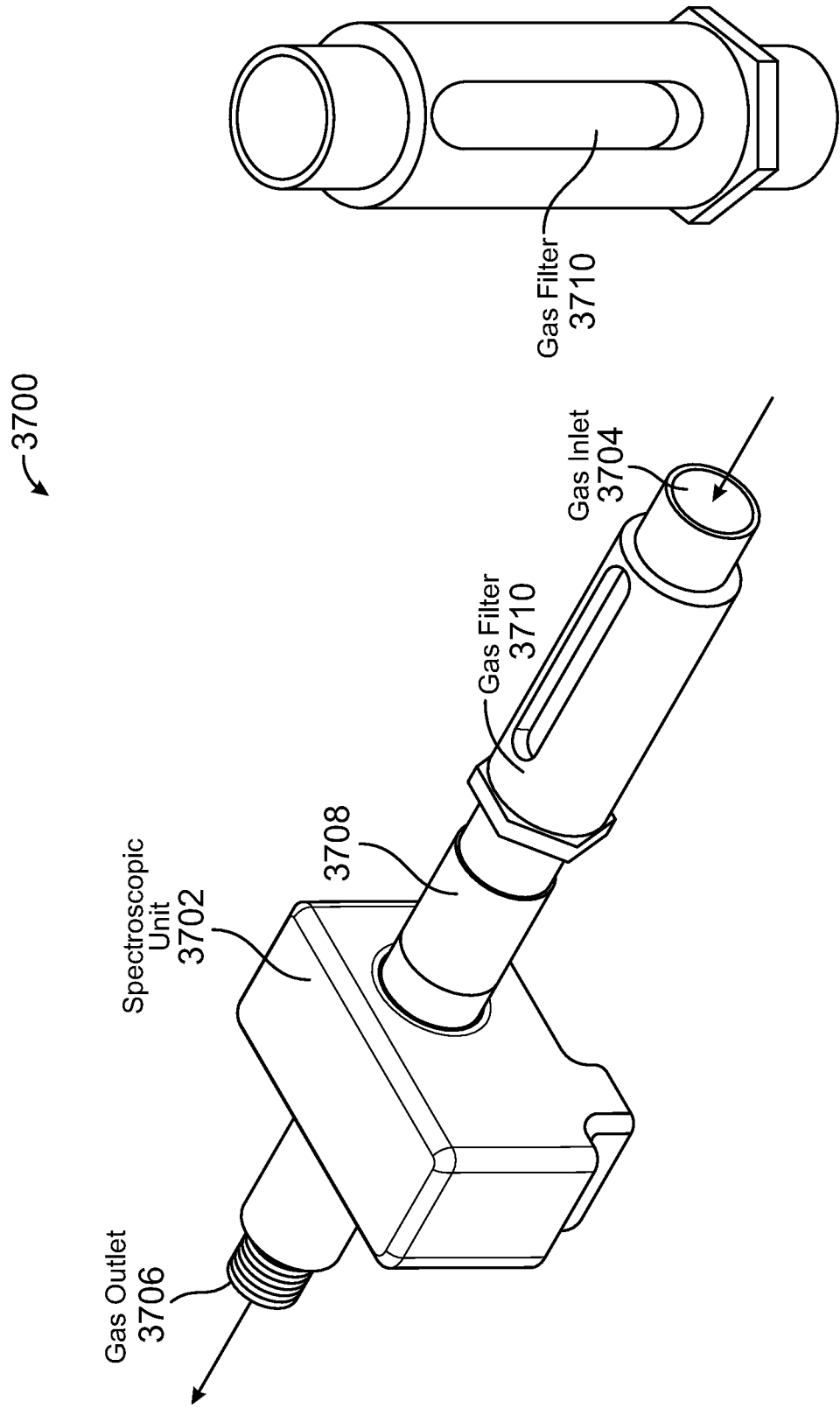
FIG. 37 is a diagram illustrating an example of a gas analyzer configuration for filtering the gas sample under test according to some aspects.

In other examples, the input gas sample to the gas cell may be filtered to remove specific gases (e.g., $H_2O$, $CO_2$, etc.) that could mask the peaks of the sample under test. FIG. 37 is a diagram illustrating an example of a gas analyzer configuration for filtering the gas sample under test according to some aspects. In the example shown in FIG. 37, the gas analyzer 3700 includes a spectroscopic unit 3702 (e.g., light source, spectral sensor, and gas cell). Gas (e.g., air) may be input to the spectroscopic unit 3702 via a gas inlet 3704 and exit the spectroscopic unit 3702 via a gas outlet 3706. The gas inlet and gas outlet may be coupled to a tube 3708 (e.g., a sample interface) configured to provide the flow of gas into and out of the spectroscopic unit 3702. In addition, a gas filter 3710 may be coupled between the tube 3708 and the gas inlet 3704 to filter the gas entering the spectroscopic unit 3702 (e.g., to remove specific gases from the gas sample under test).

In some examples, a wavenumber/wavelength (x-axis) drift may occur with aging or when environmental conditions change. To automatically compensate for wavelength shifts, various aspects provide different self-correction (e.g., self-calibration) techniques. In one technique, self-correction can be achieved by monitoring the position of $CO_2$ absorption peaks and comparing the position to the reference calibrated positions, such that the wavenumber correction factor $CF_v$ is given by:

$$CF_v = \frac{v_{ref}}{v_{meas}} \quad \text{(Equation 5)}$$

where $v_{ref}$ is the reference wavenumber and $v_{meas}$ is the measured drifted wavenumber. This can be based on the usual existence of $CO_2$ in the air with the amplified effect of the multi-pass gas cell.

Figure 38:
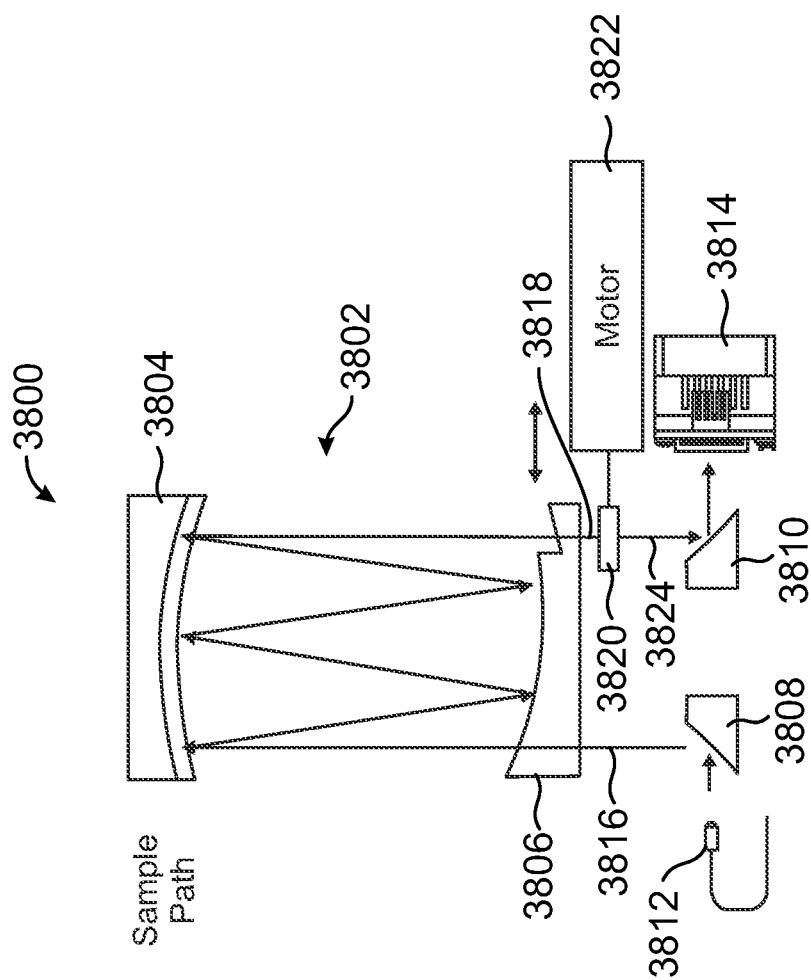
FIG. 38 is a diagram illustrating an example of a gas analyzer including a self-calibration component providing self-correction according to some aspects.

In another technique, a bandpass filter or a reference material can be inserted in the light path at a wavelength band away from the bands of interest. FIG. 38 is a diagram illustrating an example of a gas analyzer including a self-calibration component providing self-correction according to some aspects. The gas analyzer 3800 includes a gas cell 3802 (e.g., a Herriot gas cell or modified/asymmetric Herriot gas cell including reflectors 3804 and 3806, though other types of gas cells may be used), optical coupling elements 3808 and 3810, a light source 3812, and a spectral sensor 3814 (e.g., spectrometer and associated detector). In a measurement mode of the gas analyzer 3800, as shown in FIG. 38, incident light 3816 produced by the light source 3812 may be coupled into the gas cell 3802 as input light via an input optical coupling element 3808 (e.g., an off-axis parabolic mirror). The input light 3816 may be reflected between the two reflectors 3804 and 3806 to cause light interaction with a sample (not shown) within the gas cell 3802. Output light 3818 from the gas cell 3802 may be directed towards the spectral sensor 3814 via an output optical coupling element 3810 (e.g., an off-axis parabolic mirror) to obtain a sample spectrum of the sample.

In the example shown in FIG. 38, the self-calibration component includes bandpass filter 3820 (or reference material) configured to be inserted into a light path of the output light 3818. For example, the bandpass filter 3820 may be coupled to a motor 3822 to insert the bandpass filter into the light path of the output light in a calibration mode (e.g., during self-correction) to produce corrected output light 3824.

Figure 39:
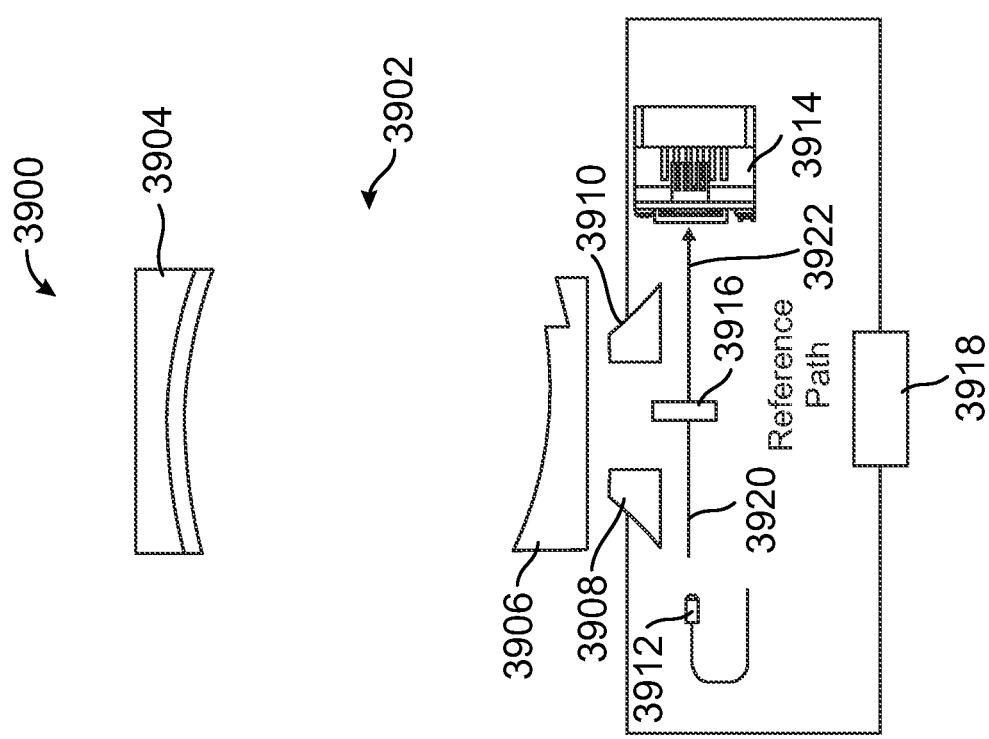
FIG. 39 is a diagram illustrating another example of a gas analyzer including a self-calibration component providing self-correction according to some aspects.

FIG. 39 is a diagram illustrating another example of a gas analyzer including a self-calibration component providing self-correction according to some aspects. As in the example shown in FIG. 38, the gas analyzer 3900 includes a gas cell 3902 (e.g., a Herriot gas cell or modified/asymmetric Herriot gas cell including reflectors 3904 and 3906, though other types of gas cells may be used), optical coupling elements 3908 and 3910, a light source 3912, and a spectral sensor 3914 (e.g., spectrometer and associated detector). In this example, the self-calibration component includes a bandpass filter or reference material 3916 that may be inserted into a reference path outside of the gas cell 3902. For example, during calibration mode, the main optical coupling elements 3908 and 3910 may be coupled to an actuator 3918. In this example, the actuator 3918 may be configured to move the main reflectors 3908 and 3910 away from the gas cell light path during calibration mode. In calibration mode, incident light 3920 produced by the light source 3912 may be directed through the filter/reference material 3916 to produce reference light 3922 coupled into the spectral sensor 3914. Thus, in the example shown in FIG. 39, self-correction can be integrated with a self-referencing architecture.

Figure 40:
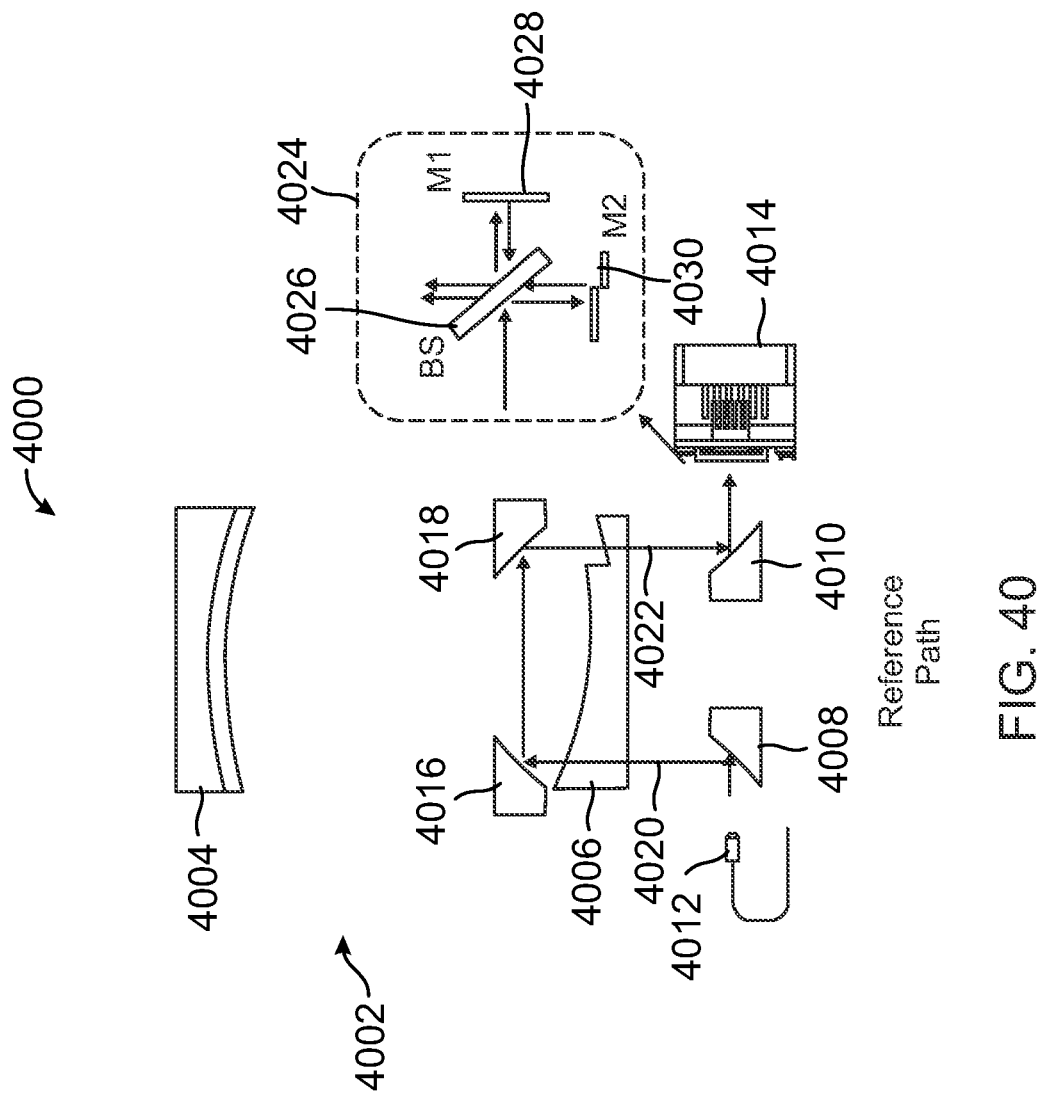
FIG. 40 is a diagram illustrating an example of a gas analyzer including a self-calibration component providing self-referencing and self-correction according to some aspects.

FIG. 40 is a diagram illustrating an example of a gas analyzer including a self-calibration component providing self-referencing and self-correction according to some aspects. The gas analyzer 4000 includes a gas cell 4002 (e.g., a Herriot gas cell or modified/asymmetric Herriot gas cell including reflectors 4004 and 4006, though other types of gas cells may be used), optical coupling elements 4008 and 4010, a light source 4012, and a spectral sensor 4014 (e.g., spectrometer and associated detector). Self-referencing may be provided by a self-calibration component that corresponds to redirecting optical elements (e.g., mirrors) 4016 and 4018 that may be inserted into a light path of the modified Herriot cell 4002 to produce a short optical path length. For example, the redirecting optical elements 4016 and 4018 may be inserted into the Herriot cell 4002 using a mechanical or electro-mechanical mechanism, similar to that described above in connection with FIGS. 20A and 20B. Thus, the redirecting optical elements 4016 and 4018 may be configured to operate in a calibration mode to receive incident light (input light) produced by the light source 4012 via an input optical coupling element 4008 and to redirect the input light through the Herriot gas cell 4002 without reflecting the light off either of the reflectors 4004 and 4006. The resulting output light (e.g., reference light) 4022 may be directed towards the spectral sensor 4014 via an output optical coupling element 4010, where a reference spectrum may be obtained.

In the example shown in FIG. 40, the reference measurement (reference spectrum) can be also used for self-correction measuring the reference bursts position. For example, the spectral sensor 4014 may include an interferometer 4024 that includes a beam splitter (BS) 4026, flat mirror (M1) 4028 in one arm, and another mirror (M2) 4030 with two-levels, leading to two bursts at two reference positions that can be used for correction of the optical path difference axis of the sensor interferometer 4024 and consequently correcting the wavelength drifts.

Figure 41:
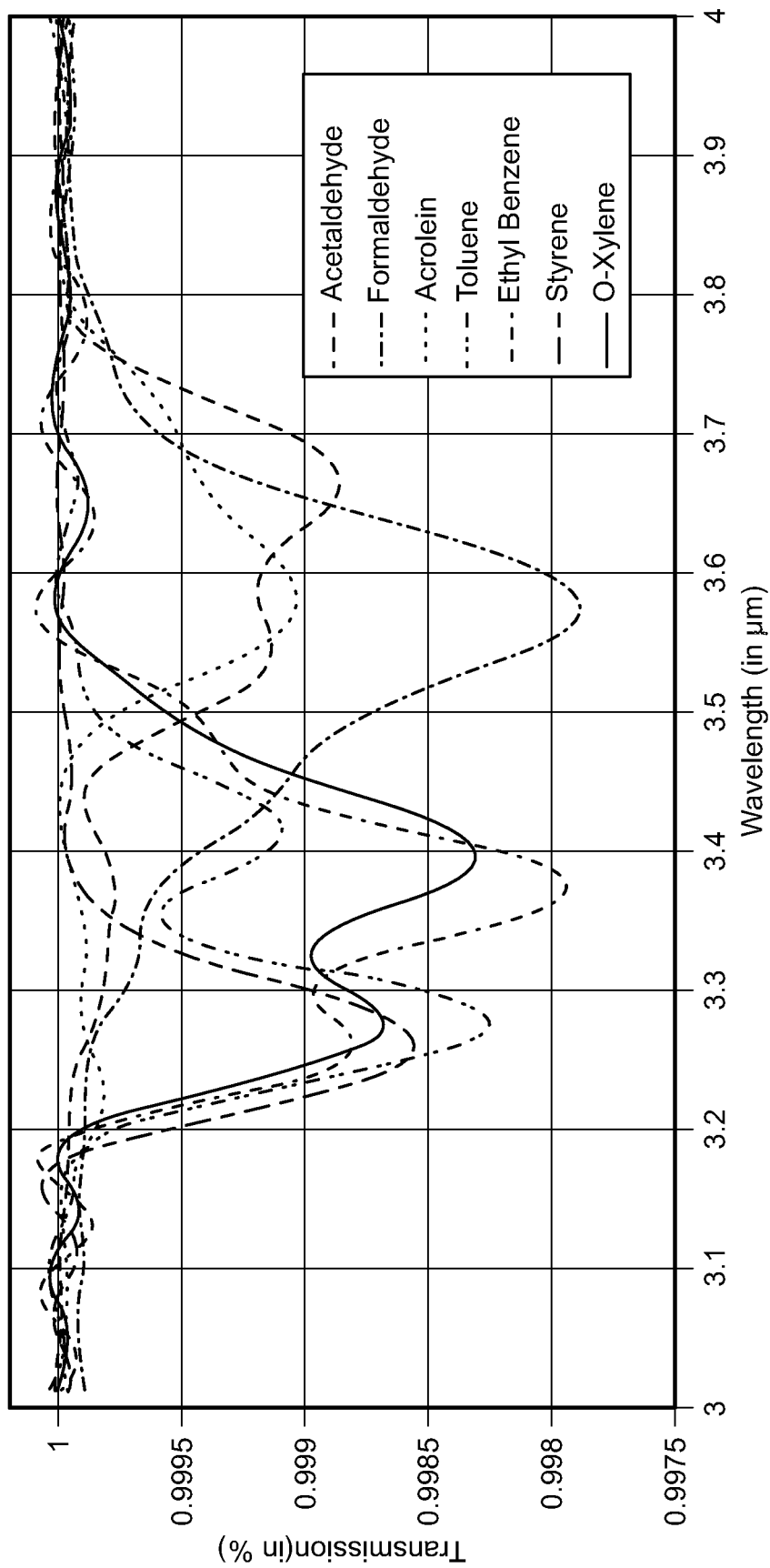
FIG. 41 is a diagram illustrating an example of spectra of volatile organic compounds.

FIG. 41 is a diagram illustrating an example of spectra of volatile organic compounds. For example, VOCs spectra with 60 cm$^{-1}$ resolution are shown in FIG. 41. Multivariate analysis techniques can be used to detect and quantify the concentration of each VOC even if there is spectral overlap between them. A database associated with the AI engine (e.g., AI engine 312/412 shown in FIGS. 3 and 4) can be a hybrid database built using both experimental and theoretical data. The theoretical data may be augmented by the synthesized spectral sensor characteristics. In some examples, partial least square (PLS) regression can be used as a linear model, while in other examples, a neural network can be used as a non-linear model.

PLS is a multivariate analysis technique that can be used in FTIR spectroscopy to predict the concentrations of gases using their spectra. For example, the following procedure may be used:

1. VOCs spectra are simulated by different concentrations using the database of PNNL (these spectra are called the training set).
2. The simulated spectrum are fed to the PLS algorithm to generate a calibration model which can predict the concentrations from the spectra.
3. VOCs spectra are simulated again but with different concentrations that is in the range of the training set (these spectra are called the testing set).
4. Noise is then added to the testing set with the amplitude that guarantees the targeted signal-to-noise ratio (SNR) for the spectrometer. Other artifacts, such as baseline drifts, wavelength errors, and self-apodization can be added.
5. Concentrations of the testing set are then calculated using the PLS calibration model and then compared to the actual concentrations.
6. Different errors (RMS error, peak error, . . . etc.) can be calculated to evaluate the PLS calibration model.

In an example, 35 gas spectra of VOCs were simulated (e.g., five simulations for every gas with different concentrations). No gas mixtures were required in preparing this calibration model. The simulation was made with signal-to-noise ratio (SNR) 20,000 and optical path length of 5 m and 15 m. Peak errors results from the PLS model are shown below in Table 1. The path length used (L1-L2) is 15 m and the SNR is 20000:1. A closer inspection of the values of the errors shows the following: 1) Formaldehyde error is the minimum because it has the strongest absorption among this group of VOCs, 2) The errors of aldehydes group is less than that of the BTEX group because the aldehydes have smaller overlapping compared to BTEX.

TABLE 1

| Gas | Peak Error ($\mu g/m^3$) |
| --- | --- |
| Formaldehyde | 5.3 |
| Acetaldehyde | 13.9 |
| Toulene | 79.5 |
| Ethyl benzene | 66.1 |
| Styrene | 60 |
| Acrolein | 35.2 |
| Xylene | 120.5 |

Since some VOCs and gases in air are overlapped in the spectrum, in various aspects, a spectral resolution enhancement algorithm can be applied before the prediction occurs. This can be inside the AI engine or in a preceding block in the system. Examples of algorithms used include autoregression, deep learning and neural network, compressive sensing FTIR, or any suitable super resolution algorithm.

Within the present disclosure, the word "exemplary" is used to mean "serving as an example, instance, or illustration." Any implementation or aspect described herein as "exemplary" is not necessarily to be construed as preferred or advantageous over other aspects of the disclosure. Likewise, the term "aspects" does not require that all aspects of the disclosure include the discussed feature, advantage or mode of operation. The term "coupled" is used herein to refer to the direct or indirect coupling between two objects. For example, if object A physically touches object B, and object B touches object C, then objects A and C may still be considered coupled to one another—even if they do not directly physically touch each other. For instance, a first object may be coupled to a second object even though the first object is never directly physically in contact with the second object. The terms "circuit" and "circuitry" are used broadly, and intended to include both hardware implementations of electrical devices and conductors that, when connected and configured, enable the performance of the functions described in the present disclosure, without limitation as to the type of electronic circuits, as well as software implementations of information and instructions that, when executed by a processor, enable the performance of the functions described in the present disclosure.

One or more of the components, steps, features and/or functions illustrated in FIGS. 1-41 may be rearranged and/or combined into a single component, step, feature or function or embodied in several components, steps, or functions. Additional elements, components, steps, and/or functions may also be added without departing from novel features disclosed herein. The apparatus, devices, and/or components illustrated in FIGS. 1-41 may be configured to perform one or more of the methods, features, or steps described herein. The novel algorithms described herein may also be efficiently implemented in software and/or embedded in hardware.

It is to be understood that the specific order or hierarchy of steps in the methods disclosed is an illustration of exemplary processes. Based upon design preferences, it is understood that the specific order or hierarchy of steps in the methods may be rearranged. The accompanying method claims present elements of the various steps in a sample order, and are not meant to be limited to the specific order or hierarchy presented unless specifically recited therein.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language of the claims, wherein reference to an element in the singular is not intended to mean "one and only one" unless specifically so stated, but rather "one or more." Unless specifically stated otherwise, the term "some" refers to one or more. A phrase referring to "at least one of" a list of items refers to any combination of those items, including single members. As an example, "at least one of: a, b, or c" is intended to cover: a; b; c; a and b; a and c; b and c; and a, b and c. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for."

What is claimed is:

1. A gas analyzer, comprising:
    a light source configured to produce incident light;
    a gas cell configured to receive a sample, the gas cell further configured to receive input light corresponding to the incident light or an interference beam produced based on the incident light, the gas cell further configured to produce output light based on light interaction with the sample within the gas cell in a measurement mode;
    a spectral sensor comprising a spectrometer configured to receive the incident light from the light source or the output light from the gas cell and further configured to produce the interference beam, the interference beam corresponding to the input light or being produced based on the output light, the spectral sensor further comprising a detector configured to obtain a sample spectrum of the sample based on the interference beam;
    an artificial intelligence engine configured to receive the sample spectrum and to generate a result indicative of at least one parameter associated with the sample based on the sample spectrum;
    control circuitry configured to control the light source and the spectral sensor; and
    a self-calibration component configured to enable background reference calibration of the sample spectrum using a background spectrum to compensate for spectral drift of the gas analyzer in a spectral domain, wherein the self-calibration component is configured to obtain the background spectrum using the gas cell and without evacuating the sample from the gas cell.

2. The gas analyzer of claim 1, wherein the spectrometer comprises a micro-electro-mechanical systems (MEMS) interference device.

3. The gas analyzer of claim 1, wherein the gas cell comprises an asymmetric Herriot cell comprising a first reflector and a second reflector opposite the first reflector configured to produce multiple reflections of the input light therebetween, the first reflector and the second reflector comprising different radius of curvature.

4. The gas analyzer of claim 3, wherein the self-calibration component comprises redirecting optical elements inserted into a light path of the asymmetric Herriot gas cell and configured to operate in a calibration mode to receive the input light and to redirect the input light through the asymmetric Herriot gas cell without reflecting off the first reflector or the second reflector to obtain a reference spectrum.

5. The gas analyzer of claim 1, wherein the gas cell comprises a White gas cell comprising a plurality of reflectors and the self-calibration component comprises redirecting optical elements inserted into a light path of the White gas cell and configured to operate in a calibration mode to receive the input light and to redirect the input light through the gas cell without reflecting off any of the plurality of reflectors to obtain a reference spectrum.

6. The gas analyzer of claim 5, wherein the redirecting optical elements are mounted on a holder coupled to a stepper motor for insertion and removal of the redirecting optical elements into and out of the light path.

7. The gas analyzer of claim 5, wherein the redirecting optical elements are coupled to a hinge for insertion and removal of the redirecting optical element into and out of the light path.

8. The gas analyzer of claim 1, wherein the gas cell comprises a circular gas cell comprising a circular reflecting element and the self-calibration component comprises a flat mirror inserted into a light path within the circular gas cell and configured to operate in a calibration mode to receive the input light and to redirect the input light through the gas cell without reflecting off the circular reflecting element to obtain a reference spectrum.

9. The gas analyzer of claim 1, wherein the self-calibration component comprises a first external reflector and a second external reflector, each of the first external reflector and the second external reflector being outside of the gas cell and configured to operate in a calibration mode to receive the incident light and to produce reference light reflected towards the spectral sensor to obtain a reference spectrum without the sample.

10. The gas analyzer of claim 9, wherein the first external reflector and the second external reflector are movable mirrors coupled to an actuator configured to insert the moveable mirrors into a light path of the incident light to reflect the incident light to produce the reference light directed towards the spectral sensor in the calibration mode.

11. The gas analyzer of claim 9, further comprising:
a reference cell configured to receive the incident light reflected from the first external reflector and to reflect the incident light towards the second external reflector to produce the reference light for reflection towards the spectral sensor.

12. The gas analyzer of claim 9, further comprising:
a shutter configured to switch between the calibration mode and the measurement mode.

13. The gas analyzer of claim 12, further comprising:
a beam combiner configured to combine the output light and the reference light for input to the spectral sensor to produce a combined spectrum in the calibration mode, the spectral sensor configured to extract the reference spectrum from the combined spectrum by subtracting the sample spectrum from the combined spectrum.

14. The gas analyzer of claim 9, further comprising:
an electro-optic controlled element configured to switch between the calibration mode and the measurement mode.

15. The gas analyzer of claim 9, further comprising:
an interferometer comprising an optical path difference between first and second light paths within the interferometer configured to switch between the calibration mode and the measurement mode.

16. The gas analyzer of claim 9, further comprising:
a bandpass filter coupled between the first external reflector and the second external reflector configured to produce the reference light comprising reference bands for input to the spectral sensor; and
a bandstop filter configured to filter the reference bands from the input light for input to the gas cell.

17. The gas analyzer of claim 9, wherein the light source is a dual filament light source and the incident light comprises first input light directed to the gas cell and second input light directed to the first external reflector, the dual filament light source being further configured to switch between the first input light and the second input light.

18. The gas analyzer of claim 9, further comprising:
an interferometer configured to receive the output light and the reference light and to produce a modulated light beam input to the spectral sensor, the interferometer comprising two arms and a two-level mirror in one of the two arms.

19. The gas analyzer of claim 1, wherein the self-calibration component comprises a moveable mirror within the gas cell configured to operate in the measurement mode at a first position of the moveable mirror and to operate in a calibration mode at a second position of the moveable mirror to receive the input light and to produce reference light reflected towards the spectral sensor to obtain a reference spectrum without the sample.

20. The gas analyzer of claim 1, wherein the gas cell comprises a toroidal gas cell comprising a single input/output and wherein the self-calibration component comprises:
a solenoid attached to a reflective material and coupled to the single input/output, the solenoid configured to move the reflective material into a light path of the incident light in a calibration mode to couple the incident light to the spectral sensor without entering the toroidal gas cell to obtain a reference spectrum.

21. The gas analyzer of claim 1, wherein the self-calibration component is included within the AI engine.

22. The gas analyzer of claim 1, wherein the self-calibration component comprises a bandpass filter configured to be inserted into a light path of the output light.

23. The gas analyzer of claim 1, wherein the spectrometer comprises an interferometer comprising two arms and the self-calibration component comprises a two-level mirror in one of the two arms.

24. The gas analyzer of claim 1, further comprising:
an atmospheric compensation unit configured to reduce an effect of the presence of one or more undesired substances in the gas cell.

25. The gas analyzer of claim 24, wherein the atmospheric compensation unit comprises one or more sensors configured to detect the one or more undesired substances and to produce sensor output fed into the AI engine, the AI engine configured to use the sensor output to produce the result.

26. The gas analyzer of claim 25, wherein the atmospheric compensation unit comprises an apodization function applied by the spectral sensor on an interferogram associated with the sample spectrum.

27. The gas analyzer 25, wherein the atmospheric compensation unit comprises a database of absorption spectra of the one or more undesired substances, and the AI engine is configured to is configured to access the database to generate processed spectra based on the absorption spectra and to provide the processed spectra to the spectrometer, the spectrometer using the processed spectra to produce the sample spectrum.

28. The gas analyzer of claim 1, further comprising:
a sample interface configured to input the sample into the gas cell.

29. The gas analyzer of claim 1, further comprising:
at least one sensor configured to generate sensor data related to the sample and to provide the sensor data to the AI engine.

30. The gas analyzer of claim 1, wherein the AI engine comprises a cloud-based AI engine.

31. The gas analyzer of claim 1, wherein the spectral sensor comprises a thermal control unit configured to stabilize a temperature at the detector.

* * * * *